(12) United States Patent
Clark et al.

(10) Patent No.: US 9,512,181 B2
(45) Date of Patent: Dec. 6, 2016

(54) FUSION PROTEINS OF CILIATE GRANULE LATTICE PROTEINS, GRANULAR PROTEIN PARTICLES THEREOF, AND USES THEREFOR

(75) Inventors: Theodore G. Clark, Ithaca, NY (US); Yelena Bisharyan, Arlington, MA (US); Ashot Papoyan, Arlington, MA (US); Kyle Anderson, Reading, MA (US); Paul Colussi, Gloucester, MA (US)

(73) Assignee: Tetragenetics, Inc., Arlington, MA (US)

( * ) Notice: Subject to any disclaimer, the term of this patent is extended or adjusted under 35 U.S.C. 154(b) by 0 days.

(21) Appl. No.: 14/122,850

(22) PCT Filed: May 29, 2012

(86) PCT No.: PCT/US2012/039882
§ 371 (c)(1),
(2), (4) Date: Aug. 1, 2014

(87) PCT Pub. No.: WO2012/166743
PCT Pub. Date: Dec. 6, 2012

(65) Prior Publication Data
US 2015/0125483 A1 May 7, 2015

Related U.S. Application Data

(60) Provisional application No. 61/491,065, filed on May 27, 2011.

(51) Int. Cl.
C07K 14/00 (2006.01)
C07K 14/435 (2006.01)
A61K 39/385 (2006.01)
C07K 14/44 (2006.01)
A61K 45/06 (2006.01)
A61K 39/00 (2006.01)

(52) U.S. Cl.
CPC ............. *C07K 14/00* (2013.01); *A61K 39/385* (2013.01); *A61K 45/06* (2013.01); *C07K 14/435* (2013.01); *C07K 14/44* (2013.01); *A61K 2039/6031* (2013.01); *A61K 2039/62* (2013.01); *C07K 2319/00* (2013.01); *C07K 2319/04* (2013.01); *C07K 2319/21* (2013.01); *C07K 2319/40* (2013.01); *C07K 2319/42* (2013.01); *C07K 2319/50* (2013.01)

(58) Field of Classification Search
CPC .... A61K 39/00; A61K 2039/53; A61K 39/12; A61K 39/145; A61K 39/002; A61K 2039/5256; A61K 2039/542; A61K 2039/552; A61K 2039/55516; A61K 2039/60; A61K 2039/6031; A61K 39/015; A61K 39/21; A61K 39/385
See application file for complete search history.

(56) References Cited

U.S. PATENT DOCUMENTS

| 8,664,374 B2 * | 3/2014 | Colussi | C12N 1/10 435/258.1 |
|---|---|---|---|
| 8,722,361 B2 * | 5/2014 | Clark | 435/69.1 |
| 2003/0166062 A1 | 9/2003 | Gonzalez-Villasenor | |
| 2008/0160137 A1 | 7/2008 | Kon et al. | |

FOREIGN PATENT DOCUMENTS

WO  WO 2010/108182 A2  9/2010

* cited by examiner

*Primary Examiner* — Padma V Baskar
(74) *Attorney, Agent, or Firm* — Wilmer Cutler Pickering Hale and Dorr LLP

(57) ABSTRACT

This invention is directed to methods for the production of immunogenic granular particles. In certain embodiments, the invention is directed to methods and products for the production of immunogenic granular particles produced in ciliates. In certain embodiments, the invention is directed to compositions comprising Granule lattice protein/Antigen (Grl/Ag) fusion polypeptides.

19 Claims, 15 Drawing Sheets

Figure 1:
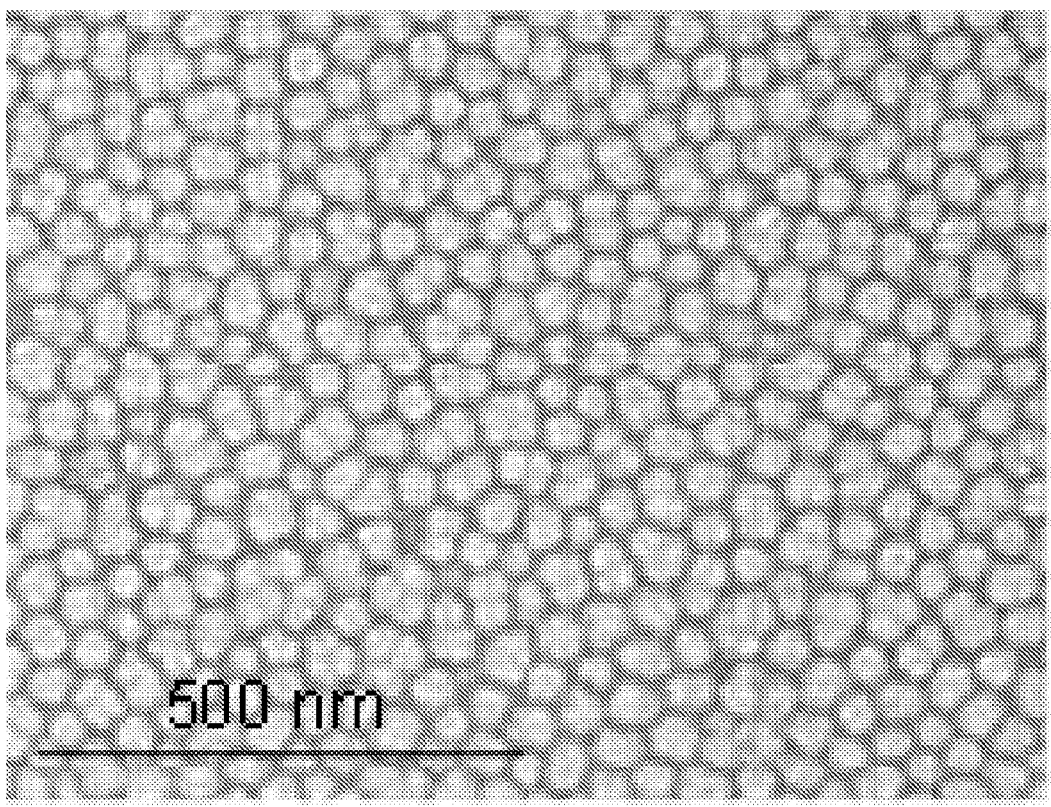

Non-assembled
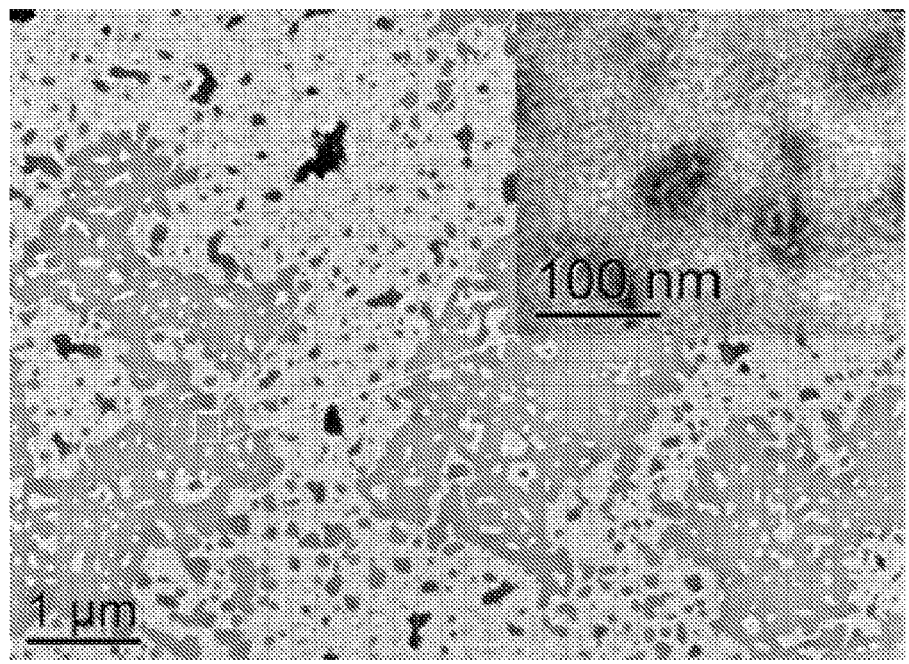
Reconstituted particles
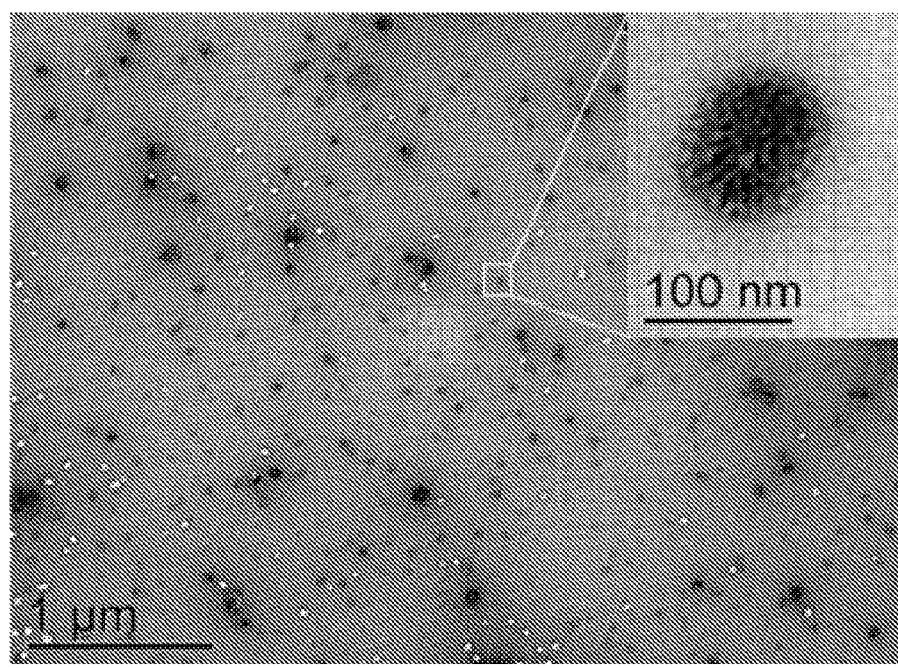
Figure 5 A-B

| H5N1 HA | Grl1 | $H_{10}$ |

Figure 9

FUSION PROTEINS OF CILIATE GRANULE LATTICE PROTEINS, GRANULAR PROTEIN PARTICLES THEREOF, AND USES THEREFOR

CROSS REFERENCE

This application claims the benefit of and priority to International Application No. PCT/US2012/039882, filed on May 29, 2012, which claims priority to U.S. Provisional Patent Application No. 61/491,065, filed May 27, 2011,the content of each of which is herein incorporated by reference in its entirety.

FIELD OF THE INVENTION

This invention is directed to methods for the production of fusion proteins comprising polypeptides derived from ciliate granule lattice proteins, the preparation of granular particles of such fusion proteins, and the use of such fusion proteins and granular particles.

BACKGROUND OF THE INVENTION

Historically, human and animal vaccines have been limited to formulations containing attenuated or killed pathogen. While effective for preventing a subset of diseases in both humans and animals, there are a number of drawbacks associated with the production of pathogen-based vaccines. For example, production can be limited due to difficulty in culturing the pathogen in question and, even if successful, the process can be slow and laborious (e.g., manufacturing flu vaccines in eggs). This can restrict mobilization of vaccine manufacturing in response to newly emerging pathogens. Further, safety is a consistent and major concern for pathogen-based vaccines as a result of the possibility that attenuated vaccines can undergo mutation or recombination in the host leading to restoration of virulence or, in the case of killed-pathogens, the possibility that not all pathogens in a given formulation have been inactivated. Alternative formulations in the form of recombinant sub-unit vaccines have also proven problematic because sub-unit based approaches commonly fail to elicit "danger signals" associated with whole killed or attenuated pathogens. This failure results in a reduced immune response and a minimization of antigen effectiveness.

Therefore, there remains a need in the art for improved methods for rapid, high-fidelity and cost-effective production and purification of recombinant polypeptides and recombinant sub-unit vaccines. This invention addresses this need.

SUMMARY OF THE INVENTION

In one aspect, the invention relates to a granular protein particle composition comprising a Grl/Ag fusion polypeptide. In certain embodiments, the composition comprises two or more different Grl/Ag fusion polypeptides. In certain embodiments, at least one of the two or more different Grl/Ag fusion polypeptides comprises a different Grl moiety from another Grl/Ag fusion polypeptide. In certain embodiments, at least one of the two or more different Grl/Ag fusion polypeptides comprises a different Ag moiety from another Grl/Ag fusion polypeptide.

In certain embodiments, the fusion polypeptide is present in a plurality of particles having a mean diameter of less than about 1 µm.

In certain embodiments, the fusion polypeptide is present in a plurality of particles having a mean diameter from about 20 to about 200 nm. In certain embodiments, the particles consist essentially of the Grl/Ag fusion polypeptide. In certain embodiments, the particles consist of at least about 10% to about 90% Grl/Ag fusion polypeptide by weight of the particle. In certain embodiments, particles further comprise one of more ciliate secretory granule proteins.

In certain embodiments, the particles can self assemble in a medium comprising a divalent cation when said divalent cation is present in the medium at a concentration of at least about 0.5 mM. In certain embodiments, the particles can self assemble in a medium comprising a divalent cation when said divalent cation is present in the medium at a concentration of at least about 2.0 mM.

In certain embodiments, the divalent cation is $Ca^{2-}$. In certain embodiments, the divalent cation is $Mg^{2+}$. In certain embodiments, the divalent cation is any of $Mn^{2+}$, $Co^{2-}$, $Cd^{2+}$, $Zn^{2+}$, $Cd^{2+}$, $Sr^{2+}$, $Ba^{2+}$, $Ni^{2+}$, $Fe^{2+}$, $Hg^{2+}$, $Pb^{2+}$, or $Cr^{2+}$.

In certain embodiments, the particles can self assemble in a medium having a pH of at least about 3.0, at least about 3.2, at least about 3.4, at least about 3.6, at least about 3.8, at least about 4.0, at least about 4.2, at least about 4.4, at least about 4.6, at least about 4.8, at least about 5.0, at least about 5.2, at least about 5.4, at least about 5.6, at least about 5.8, or at least about 6.0.

In certain embodiments, the antigenic polypeptide is selected from the group consisting of a pathogen polypeptide, a bacterial polypeptide, a viral polypeptide, protozoan polypeptide and a worm polypeptide. In certain embodiments, the antigenic polypeptide is selected from the group consisting of a fungal polypeptide, a plant polypeptide, a yeast polypeptide, an insect polypeptide or a vertebrate polypeptide. In certain embodiments, the antigenic polypeptide is selected from the group comprising a cytokine, an inflammatory molecule, a growth factor, a growth factor receptors, an oncogene, or any fragments thereof.

In certain embodiments, the Grl/Ag fusion polypeptide comprises a Grl moiety, wherein the Grl moiety is a complete pre-pro-protein, pro-protein, mature protein, or variant thereof derived from Grl 1, Grl 2, Grl 3, Grl 4, Grl5, Grl6, Grl7, Grl8 or Glr9.

In one aspect, the invention relates to a method producing an immunological response in an animal, the method comprising administering a granular protein particle composition comprising an antigenic polypeptide from a Grl/Ag fusion polypeptide to the animal.

In one aspect, the invention relates to a method for producing a granular protein particle composition comprising a Grl/Ag fusion polypeptide, the method comprising (a) expressing a Grl/Ag fusion polypeptide comprising a Grl moiety and an antigenic moiety in an expression system, wherein the antigenic moiety comprises an antigenic polypeptide or heterologous polypeptide, (b) collecting the Grl/Ag fusion polypeptide in a medium, and (c) inducing aggregation of the Grl/Ag fusion polypeptide to produce the granular protein particle composition.

In one aspect, the invention relates to a method for producing a granular protein particle composition comprising an antigenic polypeptide or heterologous polypeptide from a Grl/Ag fusion polypeptide, the method comprising (a) expressing a Grl/Ag fusion polypeptide comprising a Grl moiety and an antigenic moiety in an expression system, wherein the antigenic moiety comprises an antigenic polypeptide or heterologous polypeptide, (b) collecting the Grl/Ag fusion polypeptide in a medium, and (c) increasing divalent cation concentration of the medium so as to induce aggregation of the Grl/Ag fusion polypeptide to produce the granular protein particle composition.

In one aspect, the invention relates to a granular protein composition obtained by (a) expressing a Grl/Ag fusion polypeptide comprising a Grl moiety and an antigenic moiety in an expression system, wherein the antigenic moiety comprises an antigenic polypeptide or heterologous polypeptide, (b) collecting the Grl/Ag fusion polypeptide in a medium, and (c) increasing divalent cation concentration of the medium so as to induce aggregation of the Grl/Ag fusion polypeptide to produce the granular protein particle composition.

In certain embodiments, the concentration of divalent cations of the medium is increased to at least about 0.5 mM. In certain embodiments, the concentration of divalent cations of the medium is increased to at least about 2.0 mM. In certain embodiments, the concentration of divalent cations of the medium is increased to at least about 5.0 mM.

In one aspect, the invention relates to a method for producing a granular protein particle composition comprising an antigenic moiety from a Grl/Ag fusion polypeptide, the method comprising (a) expressing a Grl/Ag fusion polypeptide comprising a Grl moiety and an antigenic moiety in an expression system, wherein the antigenic moiety comprises an antigenic polypeptide or heterologous polypeptide, (b) collecting the Grl/Ag fusion polypeptide in a medium, and (c) adjusting the pH of the medium so as to induce aggregation of the Grl/Ag fusion polypeptide to produce a granular protein particle.

In one aspect, the invention relates to a granular protein particle composition obtained by (a) expressing a Grl/Ag fusion polypeptide comprising a Grl moiety and an antigenic moiety in an expression system, wherein the antigenic moiety comprises an antigenic polypeptide or a heterologous polypeptide, (b) collecting the Grl/Ag fusion polypeptide in a medium, and (c) adjusting the pH of the medium so as to induce aggregation of the Grl/Ag fusion polypeptide to produce a granular protein particle.

In certain embodiments of the foregoing methods, the pH in step (c) is adjusted to at least about 3.0, at least about 3.2, at least about 3.4, at least about 3.6, at least about 3.8, at least about 4.0, at least about 4.2, at least about 4.4, at least about 4.6, at least about 4.8, at least about 5.0, at least about 5.2, at least about 5.4, at least about 5.6, at least about 5.8, or at least about 6.0.

In certain embodiments, the expression system is a recombinant ciliate cell. In certain embodiments, the expression system is a recombinant *Tetrahymena* cell. In certain embodiments of the foregoing methods, the expression system is a cellular expression system, and the method further comprises a step between steps (a) and (b) of cell lysis. In certain embodiments of the foregoing methods, the expression system is a cellular expression system, and the method further comprises a step between steps (a) and (b) of inducing secretion of the Grl/Ag fusion polypeptide.

These and other aspects of the invention will be apparent to those of ordinary skill in the art in view of the following detailed description and examples.

BRIEF DESCRIPTION OF THE FIGURES

FIG. 1. Negative stain electron microscopy of discharged mucocyst contents. Shown are repeating units of approximately 50 nm diameter in a non-processed sample of a *Tetrahymena* secreted gel matrix.

FIG. 2. Pfs48/45-Grl1 construct design. HA, hemagglutinin epitope tag; $H_{10}$, 10× Histidine tag.

FIG. 3. Western analysis of pfs48/45-Grl1-expressing *Tetrahymena* whole cell lysates. The left panel is a western analysis using an anti-HA primary antibody that recognizes the engineered linear HA epitope at the C-terminus of pfs48/45. The right panel shows that a conformation specific antibody, 3E12, recognizes the pfs48/45 component of the fusion molecule. Note that the HA and 3E12 western analysis are carried out under reducing and non-reducing conditions, respectively and that this accounts for the apparent difference in mass associated with pfs48/45-Grl1 resolution by SDS-PAGE. This result both confirms expression of pfs48/45-Grl1 in *Tetrahymena* and also that the pfs48/45 component of the fusion adopts the correct conformation.

FIG. 4. Analysis of purified pfs48/45-Grl1. Left panel shows purified pfs48/45-Grl1 resolved by SDS-PAGE and detected following Coomassie blue-staining. The middle and right panels identify purified pfs48/45-Grl1 by anti-HA and anti-3E12 western analysis, respectively. Note that pfs48/45-Grl1 maintains the correct conformation of the pfs48/45 component following purification.

FIG. 5. Self-assembly of pfs48/45-Grl1 particles. FIG. 5A shows a low magnification field of negative stained non-treated purified pfs48/45-Grl1. Note lack of discernible particles >10 nm. The inset shows a higher magnification of a non-assembled soluble protein with a linear range of approximately 10 nm (double-ended arrow). FIG. 5B shows a low magnification field of negative stained purified pfs48/45-Grl1 treated with $Ca^{11}$. Note the presence of particulate forms (>10 nm) throughout the field. The inset shows a higher magnification of an assembled particle with dimensions of approximately 80-100 nm. A double-ended arrow corresponding to the inset in the left panel is included for direct comparisons of dimensions.

FIG. 6. Induced self-assembly of purified pfs48/45-Grl1. Purified pfs48/45-Grl1 was incubated at 4° C. for 48 hours in storage buffer (20 mM Tris-Cl, 50 mM NaCl, 10% glycerol, 5 mM EGTA, 0.01% Tween 80, pH 8) containing no additives (C; control sample), 2 mM $CaCl_2$ (sample 1), 5 mM $CaCl_2$, 5 mM $MgCl_2$ pH 5 (sample 2). Following incubations, samples were resolved by SDS-PAGE and fusion protein detected by blue stain (left panel) and Western Blot (right panel). Note that in sample 2, a majority of pfs48/45-Grl1 resolves at a higher apparent mass compared to control (C) and sample 1.

FIG. 7. Electron micrograph of discharged mucocyst contents. FIG. 7A shows a negative stain of mucocyst contents discharged directly on an EM grid. FIG. 7B shows a negative stain of discharged mucocyst contents treated by high-pressure (25 KPsi) microfluidization. Scale bars are shown in each panel.

FIG. 8. Electron microscopy and immunogold labeling of assembled pfs48/45-Grl1 granules. A. Negative stain images of assembled particles following incubation of purified pfs48/45-Grl1 with 5 mM $Ca^{2+}$ and $Mg^{2+}$ at pH 5. Inset shows higher magnification of an individual particle. B. anti-HA immunogold labeling of assembled particles. An individual particle is highlighted by a box and is shown at higher magnification in inset. C. Negative stain image of purified pfs48/45-Grl1 incubated with 2 mM $Ca^{2+}$. Note the absence of assembled particles. Scale bars are shown in Panels A, B and C as well as in insets.

FIG. 9. HA-Grl1 construct design. $H_{10}$, 10× Histidine tag.

FIG. 10. SDS-PAGE and Western analysis of HA-Grl1. Left panel shows purified HA-Grl1 resolved by SDS-PAGE and detected by Coomassie blue staining Right panel shows Western blot analysis of purified HA-Grl1 using a conformation dependant anti-H5N1 hemagglutinin antibody. Note detection with the conformation specific antibody indicates maintenance of correct fold of the hemagglutinin moiety.

Figure 11:
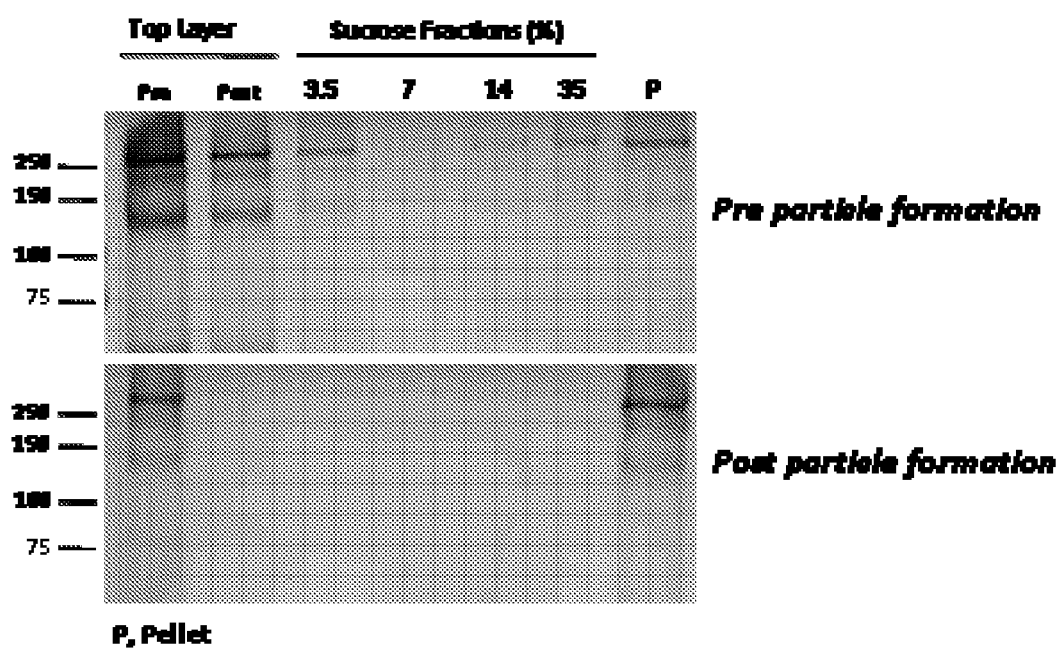

FIG. 11. Sucrose density gradient analysis of HA-Grl1 before and after induction of particle formation. Samples were collected following centrifugation through a sucrose density gradient and analyzed by SDS-PAGE. Pre, represents the top layer of the gradient prior to centrifugation; Post, represents the top layer of the gradient following centrifugation; Sucrose fractions are given in percentages of sucrose (w/v); P, pellet. Note that protein present in various fractions prior to particle formation is only detected in the pellet fraction following particle formation indicating the formation of higher density particles.

Figure 12:
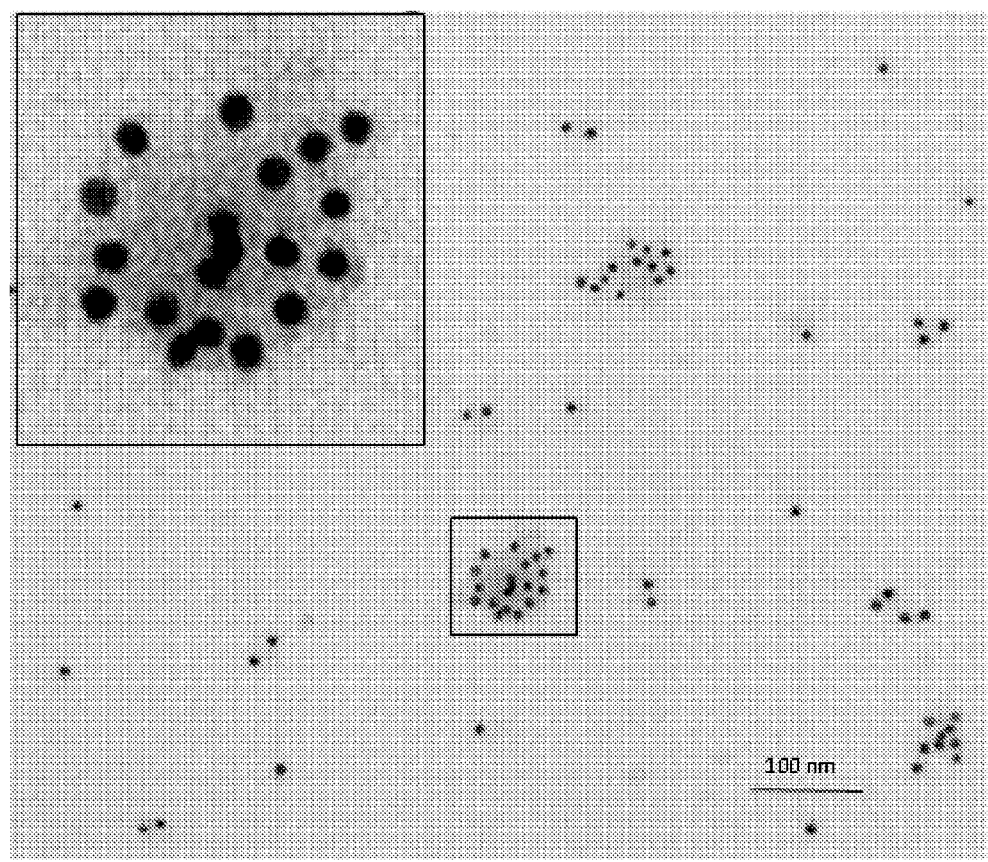

FIG. 12. Electron microscopy and immunogold labeling of assembled HA-Grl1 particles. Shown are anti-hemagglutinin immunogold labeled particles. An individual particle is highlighted by a box and is shown at higher magnification in inset.

Figure 13:
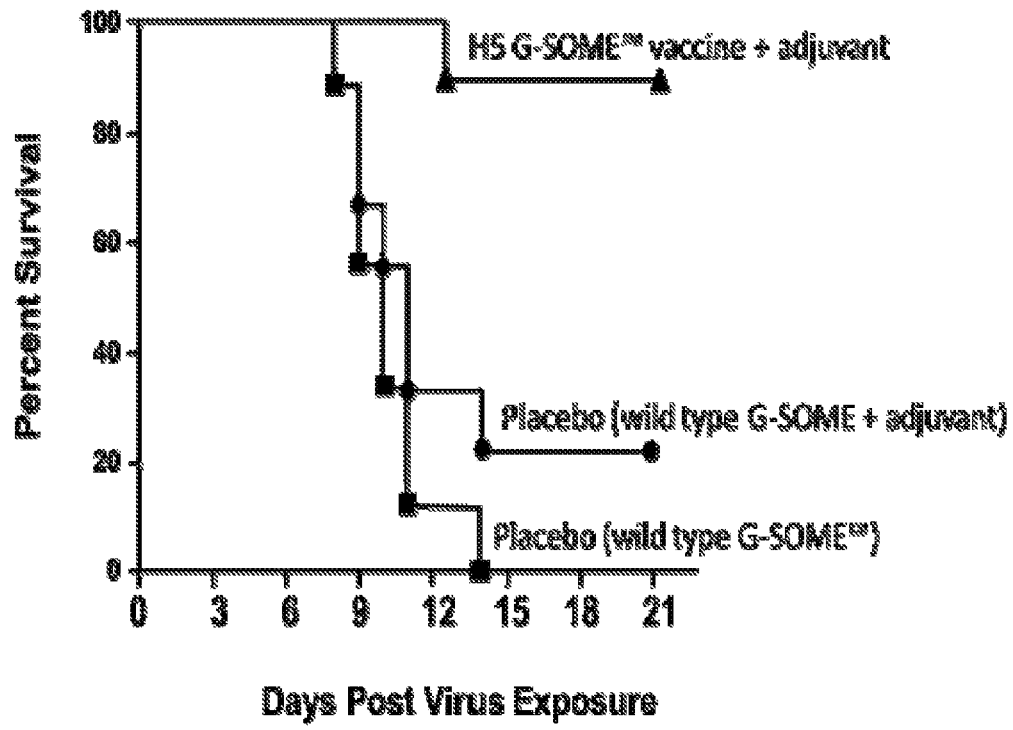

FIG. 13. Survival of mice following vaccination with either an experimental or control G-SOME formulation, and challenge with influenza A/Vietnam/1203/2004 (H5N1). Mice were immunized with a control non-related (wild type) G-SOME with and without adjuvant and an HA-G-SOME with adjuvant as described in Example 3. The HA-G-SOME showed significant improvement in survival compared to the controls (p<0.001).

Figure 14:
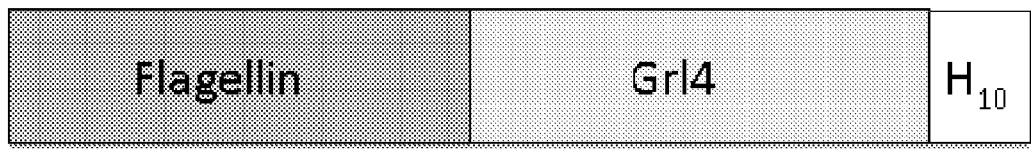

FIG. 14. Flagellin-Grl4 construct design. $H_{10}$, 10× Histidine tag.

Figure 15:
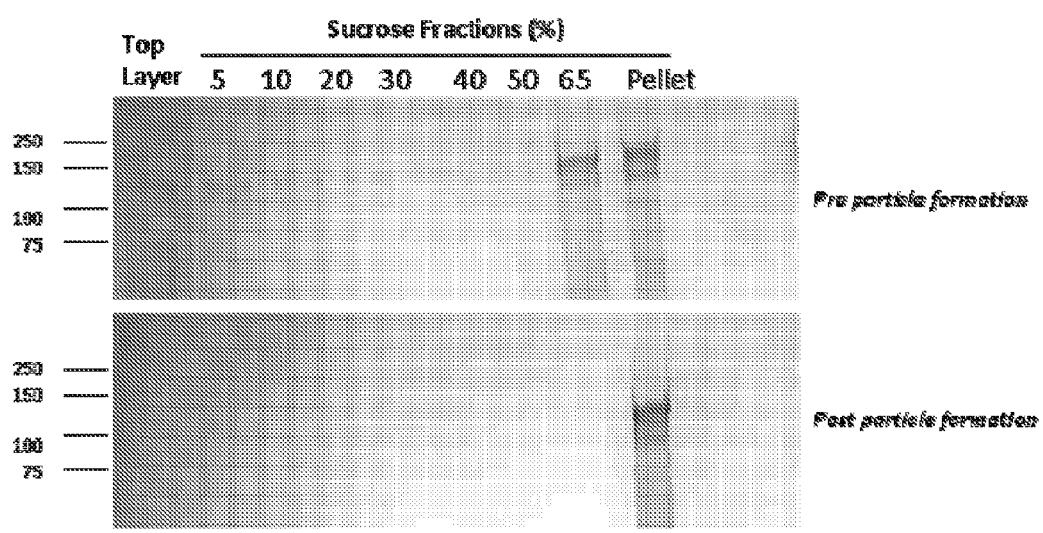

FIG. 15. Sucrose density gradient analysis of a HA-Grl1 and Falgellin-Grl4 mixture before and after induction of particle formation. Samples were collected following centrifugation through a sucrose density gradient and analyzed by SDS-PAGE. Top Layer, represents the top layer of the gradient following centrifugation. Sucrose fractions are given in percentages of sucrose (w/v). Note that protein is present in various fractions prior to particle formation (identified in each fraction including the highest sucrose density band [65%]) but is only detected in the highest sucrose density band [65%] fraction following particle formation indicating less dense proteins have assembled into higher density particles.

DETAILED DESCRIPTION OF THE INVENTION

DEFINITIONS AND REFERENCES

The patent, scientific and technical literature referred to herein establish knowledge that was available to those skilled in the art at the time of filing. The entire disclosures of the issued U.S. patents, published and pending patent applications, and other publications that are cited herein are hereby incorporated by reference to the same extent as if each was specifically and individually indicated to be incorporated by reference. In the case of any inconsistencies, the present disclosure will prevail.

All scientific and technical terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

As used herein, the term "ciliates" means eukaryotes belonging to the kingdom Chromalveolata, the superphylum Alveolata, and the phylum Ciliophora. Ciliates are complex protozoa characterized by the presence of cilia on their cell surfaces and dimorphic nuclei consisting of a macronucleus and one or more micronuclei. Exemplary genera of ciliates are the *Tetrahymena* spp. and the *Paramecium* spp.

As used herein, "*Tetrahymena* spp." refers to ciliated protozoa in the family of Tetrahymenidae. Exemplary *Tetrahymena* spp. include, but are not limited to, *T. thermophile* and *T. pyriformis*.

As used herein, the term "dense core granule" refers to a subset of the secretory organelles in ciliates that have electron dense cores and discharge in a stimulus-dependent fashion. Exemplary dense core granules include, but are not limited to, mucocysts in *Tetrahymena* spp. and trichocysts in *Paramecium* spp.

As used herein, the term "mucocyst" refers to secretory organelles in ciliates, also referred to as "cortical granules," that secrete or discharge proteinaceous mucus in response to a secretory stimulus.

As used herein, the term "Grl" refers to one of the granule lattice proteins found in the dense core granules of ciliates such as *Tetrahymena* spp., including any naturally-occurring allelic variants of the Grl1, Grl 2, Grl 3, Grl 4, Grl5, Grl6, Grl7, Grl8, Glr9 proteins.

As used herein, the term "Grl/Ag fusion protein" refers to a fusion protein comprising a Grl moiety and an antigen (Ag) moiety, in which the Grl moiety comprises a polypeptide sequence derived from a Grl protein and the antigen moiety comprises a polypeptide derived from an antigen, and in which the Grl moiety is capable of directing trafficking of the Grl/Ag fusion protein to a mucocyst and/or is sufficient to cause aggregation of the Grl/Ag fusion protein into the granular protein particles described herein, and the Ag moiety is sufficient to cause an immunogenic response against the antigen from which it is derived. As used herein, the term "Grl/Ag fusion protein" includes fusion proteins in which the Grl moiety is N-terminal (or C-terminal) to the Ag moiety or in which the Ag moiety is N-terminal (or C-terminal) to the Grl moiety. In addition, as used herein, the term Grl/Ag fusion protein includes proteins in which additional polypeptide sequences (e.g., epitope tags, purification tags, protease cleavage sites, leader or signal sequences, or cloning artifacts) are present at the N-terminus or C-terminus, or interposed between the Grl moiety and the Ag moiety. Because almost any polypeptide can serve as an antigen in at least one host, the antigenic moiety can also be described as comprising a heterologous polypeptide, which may or may not have any known antigenic properties.

As used herein, a "secretory stimulus" refers to a condition or treatment that directly or indirectly stimulates or increases the release of a protein from a dense core granule (e.g., a mucocyst). Exemplary secretory stimuli suitable for use with the methods disclosed herein include, but are no limited to, treatment with a secretagogue, mechanical shock, cross-linking of surface antigens and electroshock (e.g., electroporation).

As used herein, the term "secretagogue" refers to a compound or agent that directly or indirectly stimulates or increases the release of a protein from a dense core granule (e.g., a mucocyst). Exemplary secretagogues suitable for use with the methods disclosed herein include, but are no limited to, dibucaine, NaCl, Alcian blue, ~0.25M sucrose and compounds that increase intracellular $Ca^{2+}$ levels (e.g., calcium ionophores such as A23187; Sigma-Aldrich, St. Louis, Mo.).

The term "targeting polypeptide" means a polypeptide (a "secretory peptide") that, as a component of a larger polypeptide, directs the larger polypeptide through a secretory pathway of a cell in which it is synthesized. The larger polypeptide can be cleaved to remove the secretory peptide during transit through the secretory pathway.

As used herein, the term "endoplasmic reticulum-targeting polypeptide" means a sequence of amino acids, present at the N-terminus of a polypeptide, that causes the polypeptide to be inserted into the endoplasmic reticulum (ER) upon synthesis. Endoplasmic reticulum-targeting polypeptides typically comprise 5-20 hydrophobic amino acids that bind to a signal recognition particle (SRP) which facilitates transport into the ER. Some endoplasmic reticulum-targeting polypeptides are cleaved from the polypeptide by a signal peptidase present within the ER. Endoplasmic reticulum-targeting polypeptides are a subset of the class of polypeptides variously known as leader sequences, signal sequences, targeting signals, transit peptides, or localization signals, which target polypeptides to organelles such as the nucleus, mitochondria, chloroplasts, secretory granules and ER. For some proteins, including ciliate Grl proteins, the endoplasmic reticulum-targeting polypeptide may be referred to as a "pre-domain."

As used herein, the term "mucocyst-targeting polypeptide" means a sequence of amino acids that causes the polypeptide to be trafficked into the cortical secretory granules (i.e., mucocysts) of ciliates as the granules are formed. Mucocyst-targeting polypeptides can be N- or C-terminal to the polypeptide being targeted. Some mucocyst-targeting polypeptides are cleaved from the polypeptide by a site-specific protease present within the granules. For some proteins, including ciliate Grl proteins, the mucocyst-targeting polypeptide may be referred to as a "pro-domain."

As used herein, the term "heterologous" means, with respect to two or more genetic or protein sequences, that the sequences do not occur in the same physical relation to each other in nature and/or do not naturally occur within the same genome or protein. For example, a genetic construct may include a coding sequence which is operably joined to one or more regulatory sequences, or to one or more other coding sequences, and these sequences are considered heterologous to each other if they are not operably joined in nature and/or they are not found in the same relation in a genome in nature. Similarly, a protein may include a first polypeptide sequence which is joined by a standard peptide bond to a second polypeptide sequence, and these sequences are considered heterologous to each other if they are not found in the same relation in any protein or proteome in nature.

As used herein, the term "endogenous" means, with respect to a genetic or protein sequence, that the sequence occurs naturally in the same physical relation to a specified sequence, or occurs naturally in a specified cell or genome. For example, a genetic construct may include a coding sequence which is operably joined to one or more regulatory sequences, and the regulatory sequences are considered endogenous if they are operably joined to the coding sequence in nature, and/or they are found in the same relation in a genome in nature. Similarly, a protein that occurs naturally in a specified cell type or species is considered endogenous to that cell or species.

As used herein, the term "homolog" means a protein which is evolutionarily-related to and shares substantial structural and functional similarity with a reference protein in a different species (e.g., *Tetrahymena* spp. Grl proteins).

As used herein, the term "sequence identity" means the percentage of identical nucleotide or amino acid residues at corresponding positions in two or more sequences when the sequences are aligned to maximize sequence matching, i.e., taking into account gaps and insertions. The comparison of sequences and determination of percent identity between two sequences can be accomplished using a mathematical algorithm. Techniques for determining sequence identity are well known to one skilled in the art. For purposes of this definition, percentage sequence identity can be determined using the sequence comparison algorithm FASTA, version 3.0t78, using default parameters (Pearson and Lipman (1988), *Proc Natl. Acad. Sci. USA* 85(8):2444-8).

As used herein, the term "promoter" means a nucleotide sequence which is capable of binding RNA polymerase and initiating transcription of a downstream or 3' coding sequence.

As used herein, the term "selectable marker" means any genetic sequence which, when expressed, has a biochemical or phenotypic effect which is dominant and selectable by the presence or absence of a selection agent.

As used herein with respect to protein preparations, the term "substantially pure" means a preparation which contains at least 60% (by dry weight) the protein of interest, exclusive of the weight of other intentionally included compounds. In some embodiments, the preparation is at least 75%, at least 90%, or at least 99%, by dry weight the protein of interest, exclusive of the weight of other intentionally included compounds. Purity can be measured by any appropriate method, e.g., column chromatography, gel electrophoresis, or HPLC analysis. If a preparation intentionally includes two or more different proteins of the invention, a "substantially pure" preparation means a preparation in which the total dry weight of the proteins of the invention is at least 60% of the total dry weight, exclusive of the weight of other intentionally included compounds. For such preparations containing two or more proteins of the invention, the total weight of the proteins of the invention can be at least 75%, at least 90%, or at least 99%, of the total dry weight of the preparation, exclusive of the weight of other intentionally included compounds. Thus, if the proteins of the invention are intentionally mixed with one or more other proteins (e.g., serum albumin) or compounds (e.g., diluents, detergents, excipients, salts, polysaccharides, sugars, lipids) for purposes of administration, stability, storage, and the like, the weight of such other proteins or compounds is ignored in the calculation of the purity of the preparation.

As used herein, the term "transform" means to introduce into a cell an exogenous nucleic acid or nucleic acid analog which replicates within that cell, that encodes a polypeptide sequence which is expressed in that cell (with or without integration into the genome of the cell), and/or that is integrated into the genome of that cell so as to affect the expression of a genetic locus within the genome. The term "transform" is used to embrace all of the various methods of introducing such nucleic acids or nucleic acid analogs, including, but not limited to the methods referred to in the art as transformation, transfection, transduction, or gene transfer, and including techniques such as microinjection, DEAE-dextran-mediated endocytosis, calcium phosphate coprecipitation, electroporation, liposome-mediated transfection, biolistic bombardment, viral-mediated transfection, and the like.

As used herein, the term "vector" means any genetic construct, such as a plasmid, phage, transposon, cosmid, chromosome, virus, virion, etc., which is capable of transferring nucleic acids between cells. Vectors may be capable of one or more of replication, expression, insertion or integration, but need not possess each of these capabilities. Thus, the term includes cloning, expression, homologous recombination, and knock-out vectors.

As used herein, the terms "increase" and "decrease" mean, respectively, to cause an increase or decrease of at least 5%, as determined by a method and sample size that achieves statistical significance (i.e., $p<0.1$).

As used herein, the term "statistically significant" means having a probability of less than 10% under the relevant null hypothesis (i.e., $p<0.1$).

As used herein, the recitation of a numerical range for a variable is intended to convey that the invention may be practiced with the variable equal to any of the values within that range. Thus, for a variable that is inherently discrete, the variable can be equal to any integer value within the numerical range, including the end-points of the range. Similarly, for a variable that is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, . . . , 0.9, 0.99, 0.999, or any other real values >0 and 2, if the variable is inherently continuous.

As used herein, unless specifically indicated otherwise, the word "or" is used in the inclusive sense of "and/or" and not the exclusive sense of "either/or."

As used herein and in the appended claims, the use of singular forms of words, and the use of the singular articles "a," "an" and "the," are intended to include and not exclude the use of a plurality of the referenced term unless the context clearly dictates otherwise.

General Considerations

The present invention depends, in part, upon the surprising discovery that fusion proteins comprising a Grl moiety and a heterologous polypeptide, which in some embodiments comprises an antigenic polypeptide moiety, can be expressed in ciliates and that the fusion proteins can be recovered from whole cell lysates or regulated secretion from dense core granules, and can self-assemble to form virus-like particles. These results are surprising in view of the fact that naturally-occurring dense core granule particles comprise a complex mixture of proteins, that changes in a Grl structure have been shown to eliminate proper trafficking of the protein to mucocysts, that changes in a Grl structure have been shown to eliminate the competence of dense core granules for regulated secretion, and that the presence of heterologous polypeptide moieties would have been expected to disrupt the associations between Grls necessary for particle formation.

Moreover, without being bound by any particular theory, the methods and compositions described herein are based, in part, on the surprising finding that pro-protein processing of Grl/Ag fusion proteins (regardless of whether the Ag moiety in the Grl/Ag fusion protein is linked N- or C-terminal to the Grl moiety) either does not occur, or occurs to only a limited extent prior to secretion. Again, without being bound by any particular theory, the compositions and methods describe herein are based in part on the surprising finding that unprocessed Grl/Ag fusion proteins, such as certain embodiments of the Grl/Ag fusion proteins described herein, do not fail to be secreted and/or discharged as would have been expected from the prior art, and that they can be secreted and/or assembled in a particulate (non-soluble) state. In certain aspects, the compositions and methods described herein are based on the surprising findings that (a) the Grl/Ag fusion proteins described herein are capable of being secreted even if they comprise an unprocessed Grl moiety, and (b) the Grl/Ag fusion proteins comprising an unprocessed Grl moiety can associate with the insoluble matrix initially following secretion.

In addition, the invention depends, in part, on the finding that the Grl fusion proteins described herein can be used in an antigen delivery system suitable for the production and delivery of granular protein particles that induce a potent humoral and cellular immune response upon administration to a mammal. In certain embodiments, the humoral and cellular immune responses produced by the compositions described herein are comparable to responses induced by traditional virus-like particle (VLP) technology. Therefore, the methods and compositions described herein are useful for producing particulate antigen compositions which, upon administration to a mammal (e.g., a human) induce a greater humoral and cellular immune response than would otherwise be observed by administration of the antigen in non-particulate form.

Thus, in some embodiments, the present invention relates to methods and compositions for producing particulate antigens and to antigen delivery systems. In certain embodiments, the invention relates to immunogenic granular particles assembled from fusion proteins derived from ciliate (e.g., *Tetrahymena* spp.) cortical granule proteins that are similar to virus-like particles.

In one aspect, the invention relates to the finding that purified or partially purified preparations of Grl/Ag fusion proteins can be induced to undergo aggregation upon addition of a sufficient concentration of divalent cations (e.g., 0.5 mM $Ca^{2+}$) to a medium comprising Grl/Ag fusion proteins and/or upon adjusting the pH of a medium comprising Grl/Ag fusion proteins to a pH less than 6.0.

In another aspect, the methods and compositions described herein are directed to an antigen delivery system suitable for the production and delivery of recombinant antigens from a pathogen, including but not limited to viral, bacterial, protozoan, fungal and worm antigens. In certain embodiments, the antigenic moiety is a known antigen, or comprises a known antigen. In other embodiments, the antigenic moiety is a candidate or potential antigen to be tested for immunogenic effect, or is merely a heterologous polypeptide.

In certain embodiments, the methods and compositions described herein are directed to an antigen delivery system suitable for the production and delivery of recombinant antigens from non-pathogenic sources, including, but not limited to self-antigens, tumor rejection antigens and other cancer antigens.

In another aspect, the invention provides a general method for producing a desired heterologous fusion protein in a ciliate (e.g., *T. thermophile* or *T. pyriformis*), the method comprising linking a heterologous polypeptide of interest (e.g., a peptide hormone, growth factor) with a granule lattice protein partner.

In certain embodiments, the invention employs fusion proteins comprising a heterologous polypeptide of interest and a mucocyst-targeting moiety to direct the trafficking of the polypeptide to the mucocysts of a ciliate. In nature, polypeptides are trafficked to and between the membrane-bound compartments (e.g., the endoplasmic reticulum, the Golgi apparatus, lysosomes, vacuoles, secretory vesicles or granules, etc.) based, in part, upon the presence of N-terminal "leader sequences" or "signal sequences." As described herein, these same targeting sequences can be employed to target heterologous proteins to desired compartments.

In another aspect, the methods and compositions described herein relate to the finding that fusion proteins comprising a Grl moiety and a heterologous polypeptide of interest (e.g., an antigenic moiety) can be caused to undergo aggregation to form a granular composition of virus-like particles upon exposure to sufficient concentrations of divalent cations (e.g., 0.5 mM of $Ca^{2+}$ or $Mg^{2+}$) or a pH below 6.0.

In certain embodiments, the methods and compositions described herein further related to the finding that such particulate aggregates can be used as immunogenic compositions suitable for eliciting a potent immune response against the antigen moiety of the fusion protein upon administration to a mammal.

Granule Lattice Proteins and Grl Moieties

The Grl/Ag fusion proteins described herein are a class of designed proteins which, due to the presence of a Grl moiety, possess the ability to aggregate in vitro into immunogenic granular particles similar to virus-like particles in response to divalent cations and/or acidic pH, and/or to aggregate in vivo in ciliate dense core granules (e.g., mucocysts).

The Grl/Ag fusion polypeptide comprises a Grl moiety and, in certain embodiments, the Grl moiety is derived from any one of the naturally-occurring Grl1, Grl 2, Grl 3, Grl 4, Grl5, Grl6, Grl7, Grl8, Glr9 proteins of ciliates.

At least twelve proteins localize to mucocysts in *Tetrahymena* spp. (Chilcoat et al. (1996); Haddad et al. (2002); Bradshaw et al. (2003); Cowan et al. (2005); Bowman et al. (2005a)). The most abundant of these, known as granule lattice proteins (Grls), form a crystalline array that fills the granule space. The genome of *Tetrahymena* spp. contains at least ten predicted Grl genes, and the granule cores in *Tetrahymena* spp. comprise a cargo of polypeptide-based lattices of proteins derived from proteolytically processed Grl precursors (Collins and Wilhelm (1981); Bradshaw et al. (2003)).

In some embodiments, the Grl fusion proteins comprise a Grl1 protein, a Grl2 protein, a Grl3 protein, a Grl4 protein, a Grl5 protein, a Grl6 protein, a Grl7 protein, a Grl8 protein, or a Grl9 protein.

*T. thermophile* Grl sequences include, but are not limited to, the Granule Lattice Protein 1 Precursor (SEQ ID NO: 1), Granule Lattice Protein 2 Precursor (SEQ ID NO: 2), Granule Lattice Protein 3 Precursor (SEQ ID NO: 3), Granule Lattice Protein 4 Precursor (SEQ ID NO: 4), Granule Lattice Protein 5 Precursor (SEQ ID NO: 5), Granule Lattice Protein 6 Precursor (SEQ ID NO: 6), Granule Lattice Protein 7 Precursor (SEQ ID NO: 7), Granule Lattice Protein 8 Precursor (SEQ ID NO: 8), and Granule Lattice Protein 9 Precursor (SEQ ID NO: 9). The sequences of allelic variants or homologs from other *Tetrahymena* spp. and other ciliate species are known in the art or can be determined, and these variants and homologs can be used in the inventions described herein provided that they do not disrupt particle formation.

It is not necessary that a Grl moiety comprise the entire Grl sequence or the exact Grl sequence. For example, the pre-domain or both the pre- and pro-domains of a Grl protein need not be included in the fusion construct, and the mature protein sequence can be mutated or truncated. Thus, Grl moiety can comprise a complete Grl pre-pro-protein; a Grl pro-protein polypeptide; a truncation product of a Grl pre-pro-protein, pro-protein or mature protein; or a polypeptide that has at least 99%, 97%, 95%, 90%, 85%, 80%, 75% or 70% amino acid sequence identity to one of the foregoing. In certain embodiments, a Grl moiety variant comprises an amino acid sequence having at least about 99%, 97%, 95%, 90%, 85%, 80%, 75% or 70% identity with an amino acid sequence of mature Grl of any one of SEQ ID NO: 1-9.

When the Grl moiety is at the N-terminus of the Grl/Ag fusion protein, the pre- and pro-domains may be included to ensure proper trafficking to the ER and dense core granules. Alternatively, however, the pre-domain may be omitted and a heterologous ER signal sequence can be substituted. In addition, if the Grl/Ag fusion protein is to be isolated from cell lysate rather than by regulated secretion from dense core granules, then the pro-domain can optionally be omitted.

When the Grl moiety is at the C-terminus of the Grl/Ag fusion protein, the pre-domain can optionally be omitted. In addition the pro-domain may be included to aid in localization to the dense core granules and/or in granule formation, or can optionally be omitted.

The amino acid sequences of the Grl moieties can be modified relative to the corresponding wild-type Grl sequences without altering the relevant functional activity of a Grl (i.e., the ability to localize to the dense core granules and/or cause aggregation into granular particles in vivo or in vitro). Such modifications can be determined by routine experimentation by those of skill in the art. For example, modifications can be introduced randomly along all or part of a nucleic acid sequence encoding a Grl protein, using standard techniques (e.g., error-prone PCR, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis, gene reassembly or shuffling, and any combination thereof) and the resultant mutants can be screened by, for example, their ability to undergo aggregation in the presence of a sufficient concentration of divalent cations or acidic pH.

Variant Grls falling within the scope of this invention, can, in general, be accomplished by selecting substitutions that do not differ significantly in their effect on maintaining (a) the structure of the polypeptide backbone in the area of the substitution, (b) the charge or hydrophobicity of the molecule at the target site, or (c) the bulk of the side chain.

In certain embodiments, a variant Grl can comprise a conservative amino acid substitution in which an amino acid residue is replaced with an amino acid residue having a similar side chain configuration. Amino acid residues having similar side chain configurations have been defined in the art within in accordance with the following categories: basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine), aromatic side chains (e.g., tyrosine, phenylalanine, tryptophan, histidine), aliphatic side chains (e.g., glycine, alanine, valine, leucine, isoleucine), and sulfur-containing side chains (methionine, cysteine). Substitutions can also be made between acidic amino acids and their respective amides (e.g., asparagine and aspartic acid, or glutamine and glutamic acid).

In certain embodiments, a variant Grl can comprise a conservative amino acid substitution in which an amino acid residue is replaced with an amino acid residue having a similar side chain group. Amino acid residues having similar side chain groups have been defined in the art within in accordance with the following categories: a no side chain group (glycine), an aliphatic side chain group (alanine, valine, leucine, isoleucine, proline), a hydroxyl side chain group (serine, threonine), an acidic side chain group (aspartic acid, glutamic acid), an amide side chain group (asparagine, glutamine), a basic side chain group (lysine, arginine), an imidazole side chain group (histidine), an aromatic side chain group (phenylalanine, tyrosine, tryptophan), and a sulfur containing side chain group (methionine, cysteine) (see Sambrook et al. (2001), *Molecular Cloning: A Laboratory Manual*, Volume 3, Table A7-4).

In certain embodiments, a variant Grl can comprise a conservative amino acid substitution in which an amino acid residue is replaced an amino acid having evolutionarily positive relatedness. Amino acids having evolutionarily positive relatedness have been defined in the art as follows (wherein the amino acid(s) having evolutionarily positive relatedness are indicated in parentheses): Alanine (serine, threonine, proline, glycine); Arginine (glutamine, histidine, lysine, tryptophan); Asparagine (serine, threonine, aspartic acid, glutamic acid, glutamine, histidine, lysine); Aspartic acid (threonine, glycine, asparagine, glutamine, glutamic acid, histidine); Glutamic acid (threonine, asparagine, aspartic acid, glutamine, histidine); Glutamine (asparagine, aspartic acid, glutamic acid, histidine, arginine, lysine); Glycine (serine, threonine, alanine, aspartic acid); Histidine (asparagine, aspartic acid, glutamine, arginine); Isoleucine (threonine, methionine, leucine, valine, phenylalanine); Leucine (methionine, isoleucine, valine, phenylalanine); Lysine (threonine, asparagine, glutamine, arginine); Methionine (isoleucine, leucine, valine); Phenylalanine (isoleucine, leucine, tyrosine); Proline (serine, threonine, alanine); Serine (threonine, proline, alanine, glycine, asparagine); Threonine (serine, proline, alanine, glycine, asparagine, aspartic acid, glutamic acid, lysine, isoleucine, valine); Tryptophan (arginine, tyrosine); Tyrosine (phenylalanine, tryptophan); Valine (threonine, methionine, isoleucine, leucine) (see Dayhoff et al. (1978), in *Atlas of Protein Sequence and Structure*, ed. Dayhoff, M., Natl. Biomed. Res. Found., Silver Spring, Md.), Vol. 5, Suppl. 3, pp. 345-352).

In certain embodiments, variant of a variant Grl can comprise a conservative amino acid substitution in which an amino acid residue is replaced an amino acid having evolutionarily positive relatedness. Amino acids having evolutionarily neutral relatedness have been defined in the art as follows (wherein the amino acid(s) having evolutionarily neutral relatedness are indicated in parentheses): Alanine (asparagine, aspartic acid, glutamine, glutamic acid, valine); Arginine (serine, proline, asparagine, methionine); Asparagine (alanine, glycine, arginine); Aspartic acid (serine, alanine, lysine); Cysteine (serine, tyrosine); Glutamic acid (serine, alanine, glycine, lysine); Glutamine (proline, alanine); Glycine (asparagine, glutamic acid); Histidine (proline, lysine, tyrosine); Lysine (serine, asparagine, glutamic acid, histidine, methionine); Methionine (arginine, lysine, phenylalanine); Phenylalanine (methionine, tryptophan); Proline (glutamine, histidine, arginine); Serine (cysteine, aspartic acid, glutamic acid, arginine, lysine); Threonine (none); Tryptophan (phenylalanine); Tyrosine (cysteine, histidine); Valine (alanine) (see Dayhoff et al. (1978), in *Atlas of Protein Sequence and Structure*, ed. Dayhoff, M., Natl. Biomed. Res. Found., Silver Spring, Md.), Vol. 5, Suppl. 3, pp. 345-352).

In another embodiment, the Grl variants described herein can comprise a non-natural amino acid. As used herein, a non-natural amino acid can be, but is not limited to, an amino acid comprising a moiety where a chemical moiety is attached, such as an aldehyde- or keto-derivatized amino acid, or a non-natural amino acid that includes a chemical moiety. A non-natural amino acid can also be an amino acid comprising a moiety where a saccharide moiety can be attached, or an amino acid that includes a saccharide moiety. Examples of non-classical amino acids suitable for use with the methods and compositions described herein include, but are not limited to, D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, C α-methyl amino acids, N α-methyl amino acids, and amino acid analogs in general.

The Grls described herein can also comprise one or more amino acid analog substitutions, e.g., unnatural amino acids such as α,α-disubstituted amino acids, N-alkyl amino acids, lactic acid, and the like. These analogs include phosphoserine, phosphothreonine, phosphotyrosine, hydroxyproline, γ-carboxyglutamate; hippuric acid, octahydroindole-2-carboxylic acid, statine, 1,2,3,4,-tetrahydroisoquinoline-3-carboxylic acid, penicillamine, ornithine, citruline, α-methylalanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, ω-N-methylarginine, and other similar amino acids and imino acids and tert-butylglycine.

The variant Grls described herein can further comprise polypeptide analogs, such as peptide mimetics (Fauchere (1986), *Adv. Drug Res.* 15:29; Veber and Freidinger (1985), *Trends Neurosci.* 8:392-96; Evans et al. (1987), *J. Med. Chem.* 30:1229-39). Generally, peptidomimetics are structurally similar to a template polypeptide (i.e., a polypeptide that has a biological or pharmacological activity), such as the Grls described herein, but have one or more peptide linkages replaced by a linkage selected from the group consisting of: —CH$_2$NH—, —CH$_2$S—, —CH$_2$—CH$_2$—, —CH=CH—(cis and trans), —COCH$_2$—, —CH(OH)CH$_2$—, and —CH$_2$SO—, by methods known in the art and further described in the following references: Spatola in *Chemistry and Biochemistry of Amino Acids, Peptides, and Proteins*, Weinstein, ed., Marcel Dekker, New York, p. 267 (1983); Spatola (1983), *Vega Data*, Vol. 1, Issue 3, *Peptide Backbone Modifications*; Morley (1980), *Trends Pharmcol. Sci.* 1:463-68; Hudson et al. (1979), *Int. J. Pept. Prot. Res.* 14:177-85; Spatola et al. (1986), *Life Sci.* 38:1243-49; Hann (1982), *J. Chem. Soc. Perkin Trans.* 1, 307-314; Almquist R G et al., J. Med. Chem. 23:1392-98 (1980); Jennings-White et al. (1982), *Tetrahedron Lett.* 23:2533-34; EP 0 045 665; Holladay et al. (1983), *Tetrahedron Lett.* 24:4401-04; Hruby (1982), *Life Sci.* 31:189-99.

Chemically modified derivatives of the Grls described herein can also be prepared. For example, amides of the Grls described herein can be prepared by techniques well known in the art for converting a carboxylic acid group or precursor, to an amide. One method for amide formation at the C-terminal carboxyl group is to cleave the polypeptide, or fusion thereof from a solid support with an appropriate amine, or to cleave in the presence of an alcohol, yielding an ester, followed by aminolysis with the desired amine.

Salts of carboxyl groups of the Grls described herein can be prepared by contacting the polypeptide, or fusion thereof with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the Grls described herein can be prepared by utilizing an N-acyl protected amino acid for the final condensation, or by acylating a protected or unprotected polypeptide, or fusion thereof O-acyl derivatives can be prepared, for example, by acylation of a free hydroxy polypeptide or polypeptide resin. Either acylation can be carried out using standard acylating reagents such as acyl halides, anhydrides, acyl imidazoles, and the like. Both N- and O-acylation can be carried out together, if desired.

Formyl-methionine, pyroglutamine and trimethyl-alanine can be substituted at the N-terminal residue of certain Grl moieties described herein. Other amino-terminal modifications include aminooxypentane modifications.

Antigenic Moieties, Antigenic Polypeptides and Heterologous Polypeptides

The Grl/Ag fusion proteins described herein can comprise any antigenic moiety that does not disrupt the ability of the Grl moiety to cause aggregation of the Grl/Ag fusion polypeptide to produce a granular protein particle composition. In certain embodiments, the antigenic moiety comprises a known antigen. Alternatively, the antigenic moiety comprised in a Grl/Ag fusion protein can be any heterologous polypeptide, including, in certain embodiments, biologically active proteins, that does not disrupt the ability of the Grl moiety to cause aggregation of the Grl/Ag fusion polypeptide to produce a granular protein particle composition. As a general matter, the antigenic moiety should not include any transmembrane domains as these may prevent the fusion protein from trafficking properly through the ER. Therefore, in some embodiments, the antigenic moiety is substantially free of a transmembrane domain sequence.

Heterologous polypeptides suitable for use in connection with the methods and compositions described herein include, but are not limited to, biomolecules useful in medicine, agriculture and other scientific and industrial fields.

Antigenic polypeptides can be derived from any source or origin and can include polypeptides found in prokaryotes, viruses, and eukaryotes, including fungi, plants, yeasts, insects, and animals, including mammals (e.g., humans). Such polypeptides can be known antigens or hypothetical antigens, and can be identified using common sequence repositories. Examples of such sequence repositories, include, but are not limited to, GenBank EMBL, DDBJ and the NCBI. Antigenic polypeptides can also include polypeptides that have at least about 60%, 70%, 75%, 80%,90%, 95%, or at least about 99% or more identity to any known or available polypeptide (e.g., a therapeutic polypeptide, a diagnostic polypeptide, an industrial enzyme, or portion thereof, and the like).

Accordingly, heterologous polypeptides and antigenic polypeptides suitable for use in the invention include, but are not limited to, cytokines, inflammatory molecules, growth factors, their receptors, and oncogene products or portions thereof. Examples of cytokines, inflammatory molecules, growth factors, their receptors, and oncogene products include, but are not limited to, e.g., α-1 antitrypsin, Angiostatin, Antihemolytic factor, antibodies (including an antibody or a functional fragment or derivative thereof selected from: Fab, Fab', F(ab)2, Fd, Fv, ScFv, diabody, tribody, tetrabody, dimer, trimer or minibody), angiogenic molecules, angiostatic molecules, Apolipopolypeptide, Apopolypeptide, Asparaginase, Adenosine deaminase, Atrial natriuretic factor, Atrial natriuretic polypeptide, Atrial peptides, Angiotensin family members, Bone Morphogenic Polypeptides (BMP-1, BMP-2, BMP-3, BMP-4, BMP-5, BMP-6, BMP-7, BMP-8a, BMP-8b, BMP-10, BMP-15, etc.); C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant polypeptide-1, Monocyte chemoattractant polypeptide-2, Monocyte chemoattractant polypeptide-3, Monocyte inflammatory polypeptide-1α, Monocyte inflammatory polypeptide-1β, RANTES, 1309, R83915, R91733, HCC1, T58847, D31065, T64262), CD40 ligand, C-kit Ligand, Ciliary Neurotrophic Factor, Collagen, Colony stimulating factor (CSF), Complement factor 5a, Complement inhibitor, Complement receptor 1, cytokines, (e.g., epithelial Neutrophil Activating Peptide-78, GRO α/MGSA, GRO β, GRO γ, MIP-1 α, MIP-1 δ, MCP-1), deoxyribonucleic acids, Epidermal Growth Factor (EGF), Erythropoietin, Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog polypeptides (e.g., Sonic, Indian, Desert), Hemoglobin, Hepatocyte Growth Factor (HGF), Hepatitis viruses, Hirudin, Human serum albumin, Hyalurin-CD44, Insulin, Insulin-like Growth Factor (IGF-I, IGF-II), interferons (e.g., interferon-α, interferon-β, interferon-γ, interferon-ϵ, interferon-ζ, interferon-η, interferon-ϵ, interferon-λ, interferon-τ, interferon-ζ, interferon-ω), glucagon-like peptide (GLP-1), GLP-2, GLP receptors, glucagon, other agonists of the GLP-1R, natriuretic peptides (ANP, BNP, and CNP), Fuzeon and other inhibitors of HIV fusion, Hirudin and related anticoagulant peptides, Prokineticins and related agonists including analogs of black mamba snake venom, TRAIL, RANK ligand and its antagonists, calcitonin, amylin and other glucoregulatory peptide hormones, and Fc fragments, exendins (including exendin-4), exendin receptors, interleukins (e.g., IL-1, IL-2, IL-3, IL-4, IL-5, IL-6, IL-7, IL-8, IL-9, IL-10, IL-11, IL-12, etc.), I-CAM-1/LFA-1, Keratinocyte Growth Factor (KGF), Lactoferrin, leukemia inhibitory factor, Luciferase, Neurturin, Neutrophil inhibitory factor (NIF), oncostatin M, Osteogenic polypeptide, Parathyroid hormone, PD-ECSF, PDGF, peptide hormones (e.g., Human Growth Hormone), Oncogene products (Mos, Rel, Ras, Raf, Met, etc.), Pleiotropin, Polypeptide A, Polypeptide G, Pyrogenic exotoxins A, B, and C, Relaxin, Renin, ribonucleic acids, SCF/c-kit, Signal transcriptional activators and suppressors (p53, Tat, Fos, Myc, Jun, Myb, etc.), Soluble complement receptor 1, Soluble I-CAM 1, Soluble interleukin receptors (IL-1, 2, 3, 4, 5, 6, 7, 9, 10, 11, 12, 13, 14, 15), soluble adhesion molecules, Soluble TNF receptor, Somatomedin, Somatostatin, Somatotropin, Streptokinase, Superantigens, i.e., *Staphylococcal* enterotoxins (SEA, SEB, SEC1, SEC2, SEC3, SED, SEE), Steroid hormone receptors (such as those for estrogen, progesterone, testosterone, aldosterone, LDL receptor ligand and corticosterone), Superoxide dismutase (SOD), Toll-like receptors (such as Flagellin), Toxic shock syndrome toxin (TSST-1), Thymosin a 1, Tissue plasminogen activator, transforming growth factor (TGF-α, TGF-β), Tumor necrosis factor β (TNF β), Tumor necrosis factor receptor (TNFR), Tumor necrosis factor-α(TNF α), transcriptional modulators (for example, genes and transcriptional modular polypeptides that regulate cell growth, differentiation and/or cell regulation), Vascular Endothelial Growth Factor (VEGF), virus-like particles, VLA-4NCAM-1, Urokinase, and signal transduction molecules.

Additional antigenic moieties suitable for use with the methods described herein include, but are not limited to, enzymes (e.g., industrial enzymes) or portions thereof. Examples of enzymes include, but are not limited to amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Further antigenic moieties for use with the methods described herein include, but are not limited to, agriculturally related polypeptides such as insect resistance polypeptides (e.g., Cry polypeptides), starch and lipid production enzymes, plant and insect toxins, toxin-resistance polypeptides, Mycotoxin detoxification polypeptides, plant growth enzymes (e.g., Ribulose 1,5-Bisphosphate Carboxylase/Oxygenase), lipoxygenase, and Phosphoenolpyruvate carboxylase.

Antigenic moieties suitable for use with the methods described herein include, but are not limited to, prophylactic vaccine or therapeutic vaccine polypeptides. Vaccine polypeptides include polypeptides, or polypeptide fragments from infectious fungi (e.g., *Aspergillus, Candida* species), bacteria (e.g., *Escherichia* spp., *Staphylococci* spp., *Streptococci* spp.); protozoa such as sporozoa (e.g., *Plasmodia*), rhizopods (e.g., *Entamoeba*) and flagellates (*Trypanosoma, Leishmania, Trichomonas, Giardia,* etc.); viruses such as (+) RNA viruses (examples include Poxviruses (e.g., vaccinia); Picornaviruses (e.g., polio); Togaviruses (e.g., rubella); Flaviviruses (e.g., HCV); and Coronaviruses), (−) RNA viruses (e.g., Rhabdoviruses (e.g., VSV); Paramyxovimses (e.g., RSV); Orthomyxovimses (e.g., influenza); Bunyaviruses; and Arenaviruses), dsDNA viruses (e.g., Reoviruses), RNA to DNA viruses (i.e., retroviruses); HIV; HTLV; and certain DNA to RNA viruses such as Hepatitis B.

Other suitable heterologous polypeptides for use in the invention include, but are not limited to, antibodies, antibody fragments, cytokines, growth factors, protein kinases, proteases, protein hormones or any fragment thereof. Similarly, the methods described herein are suitable for the production of specialty proteins. The use of such specialty proteins can include, but is not limited to, prototype vaccines for animal model studies, structural studies, or as therapeutic proteins. For example, quantities of antigens can be produced according to the methods described herein.

Expression of Grl/Ag Fusion Proteins

In some embodiments, the methods described herein can comprise expressing a Grl/Ag fusion protein in a cellular expression system and inducing secretion of the Grl/Ag fusion protein into the cellular medium, for example by regulated secretion. In other embodiments, the methods described herein can comprise expressing a Grl/Ag fusion protein in a cellular expression system and releasing the Grl/Ag fusion protein into a medium by cell lysis.

Although, in certain embodiments, the methods and compositions of the invention relate to the Grls of the ciliated protist *T. thermophile,* the expression of Grl fusion molecules according to the methods described herein need not be restricted to *Tetrahymena* spp. or even ciliates. Rather, the Grl/Ag fusion proteins can be expressed in any host cell that (a) maintains the self-assembly properties of the Grl component of the fusion molecule and (b) produces the antigen component of the molecule in a suitably immunogenic form. Accordingly, the methods and compositions described herein can be useful to provide increased flexibility in the manufacture of potent and effective vaccines where production of a particular antigen is better suited to one cell type over another due, for example, to particular post-translational modification requirements (e.g., production in mammalian cells as opposed to insect cells). In particular, because some embodiments of the invention do not require that the Grl/Ag fusion proteins must be assembled into particles in the dense core granules or discharged by regulated secretion from a ciliate, but that the Grl/Ag fusion proteins can be purified from cell lysate and assembled in the form of immunogenic particles, the Grl/Ag fusion proteins can be expressed in any convenient cell (e.g., bacteria, fungi, insects, mammals).

Conveniently, however, for regulated secretion of Grl/Ag fusion proteins, the *Tetrahymena* regulated secretion pathway can be used as described in WO 2010/108182 (PCT/US10/028165), the entire disclosure of which is incorporated by reference herein. WO 2010/108182 discloses targeting recombinant proteins to *Tetrahymena* mucocysts via fusion to native Grl proteins and harvesting recombinant fusion proteins from the discharged mucocyst material following induced secretion. WO 2010/108182 does not teach, however, the production of self-assembled granular protein particles comprising Grl/Ag fusion proteins as described herein.

In certain embodiments, the Grl/Ag fusion proteins described herein can comprise an endoplasmic reticulum-targeting polypeptide N-terminal to the mucocyst-targeting moiety. The endoplasmic reticulum-targeting polypeptide, when present, can be from the same protein as the mucocyst-targeting polypeptide, or it can be heterologous. Indeed, the endoplasmic reticulum-targeting polypeptide can be from any ER-targeted polypeptide, even from different species, as long as it is effective as an ER signal sequence. In some embodiments, the endoplasmic reticulum-targeting polypeptide is the ER signal sequence or pre-domain of a Grl protein or other granule-associated protein. In other embodiments, it can be a heterologous or exogenous sequence, such as the 22 amino acid signal peptide derived from the immobilization antigen variant B protein of *Ichthyophthirius multifiliis,* which has been shown to be functional in *Tetrahymena.*

The Grl/Ag fusion proteins described herein can also be produced using any in vitro expression system known in the art or can be synthesized by chemical methods. Methods for expression of heterologous proteins in recombinant hosts, chemical synthesis of polypeptides, and in vitro translation are well known in the art and are described further in Sambrook et al. (2001), *Molecular Cloning: A Laboratory Manual,* (Cold Spring Harbor Press, Cold Spring Harbor, N.Y.); Berger and Kimmel (1987), *Methods in Enzymology,* Volume 152, Guide to Molecular Cloning Techniques, (Academic Press, Inc., San Diego, Calif.); Gutte and Merrifield (1969), *J. Am. Chem. Soc.* 91:501-02; Chaiken (1981), *CRC Crit. Rev. Biochem.* 11:255-301; Kaiser et al. (1989), *Science* 243:187-92; Merrifield (1986), *Science* 232:341-47; Kent (1988), *Ann. Rev. Biochem.* 57:957-89; Offord (1980), *Semisynthetic Proteins* (Wiley Publishing). Exemplary peptide synthesis methods known in the art include, but are not limited to those described in Stewart et al. (1984), *Solid Phase Peptide Synthesis* (Pierce Biotechnology, Inc., Rockford, Ill.); Bodanszky (1984), *Principles of Peptide Synthesis* (Springer-Verlag, New York); and Pennington et al.

(1994), *Peptide Synthesis Protocols* (Humana Press, Totowa, N.J.). Additionally, many companies offer custom peptide synthesis services.

The Grl/Ag fusion proteins described herein can also be produced by direct chemical synthesis. For example, the Grl/Ag fusion proteins described herein can be produced as modified polypeptides, with nonpeptide moieties attached by covalent linkage to the N-terminus and/or C-terminus. In certain embodiments, either the carboxy-terminus or the amino-terminus, or both, are chemically modified. Common modifications of the terminal amino and carboxyl groups, include, but are not limited to acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments. Certain amino-terminal and/or carboxy-terminal modifications and/or polypeptide extensions to the core sequence can provide advantageous physical, chemical, biochemical, and pharmacological properties, such as: enhanced stability, increased potency and/or efficacy, resistance to serum proteases, desirable pharmacokinetic properties, and others.

The Grl/Ag fusion proteins can also include a known epitope tag or other fusion polypeptide. Exemplary fusion polypeptides suitable for use with the methods described herein include, but are not limited to glutathione S-transferase (GST), maltose E binding protein (MBP), Green Fluorescent Protein (GFP), and variants thereof. Exemplary epitope tags suitable for use with the methods described herein include, but are not limited to FLAG, HA, Myc, Histidine and T7 epitope tags In certain aspects of the invention, granular immunogenic particle compositions are produced according to a method comprising steps of expressing a Grl/Ag fusion polypeptide comprising a Grl moiety and an antigenic moiety in an expression system, collecting the polypeptide in a medium, and inducing aggregation of the polypeptide to produce the granular immunogenic particle composition. Thus, the Grl/Ag fusion proteins described herein can be secreted and isolated from a mixture of cells and medium containing the protein or polypeptide.

Alternatively, the protein or polypeptide can be retained cytoplasmically and the cells harvested, lysed, and the protein isolated. Any method of cell lysis known in the art can be used in conjunction with the methods described herein, including, but not limited to chemical lysis (e.g., detergents), enzymatic lysis, or physical or mechanical methods (e.g., sonication or French press).

The Grl/Ag fusion proteins described herein can be isolated, purified or partially purified according to any method of protein purification or isolation known in the art. For example, Grl/Ag fusion proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, the Grl/Ag fusion proteins can be produced in a recombinant system in which the protein contains an additional sequence tag that facilitates purification, such as, but not limited to, a polyhistidine sequence, or a sequence that specifically binds to an antibody, such as FLAG and GST. In certain embodiments, the Grl/Ag fusion proteins can be purified from a crude lysate of the host cell by chromatography on an appropriate solid-phase matrix.

*T. thermophila* is a free-living ciliated protist. The free-living ciliate protists are a large and diverse phylum (Ciliata) whose members display a structural and functional complexity comparable to that of higher metazoa (Fankel (2000); Turkewitz et al. (2002)), and include over 7,000 species with 11 major subdivisions. Like most other eukaryotic cells *T. thermophila* can traffic proteins to the constitutive pathway and eventually out of the cell in the surrounding environs.

*Tetrahymena* spp. are amenable to genetic manipulation, can be grown on a large scale and have a doubling time of 1.5-3 hrs. Unlike *T. thermophila,* which has an optimal growth temperature of 35° C., the optimal growth temperature for *T. pyriformis* is lower (maximal growth temperature of 34° C.). Cells reach high-density in a short time on a variety of inexpensive media and can be expanded for growth in bioreactors up to several thousand liters in size (Hellenbroich et al. (1999); de Coninck et al. (2000)). Methods for transformation, along with robust, inducible promoters for driving high-level gene expression have recently been described for this system (Bruns and Cassidy-Hanley (2000); Gaertig and Kapler (2000); Shang et al. (2002); Boldrin et al. (2006)).

Unicellular eukaryotes (e.g., *Saccharomyces cerevisiae* and *Pichia pastoris*) grow rapidly in inexpensive media and share some common pathways of protein folding, post-translational modification and protein targeting with more advanced organisms such as mammalian cells. Although the use of such unicellular eukaryotes for heterologous protein expression systems is known in the art, their rigid cell walls are an impediment to downstream protein purification.

Most eukaryotic cells are capable of constitutive secretion. Constitutive secretion is a process in which proteins can be delivered to the extracellular space via cargo vesicles that traffic to the cell surface by way of the endoplasmic reticulum (ER) and Golgi (Burgess and Kelly (1987)). This pathway has been harnessed for the production of recombinant gene products in a variety of systems and has significant advantages for protein purification because the process of secretion separates proteins of interest from the bulk of contaminating cellular material, thereby obviating the need for cell lysis.

While most cells (including eukaryotic microbes) secrete proteins constitutively, some specialized cells also store proteins in cortical secretory organelles (granules). These secretory organelles can be discharged in a stimulus-dependent or regulated fashion (Burgess and Kelly (1987); Miller and Moore (1990); Gundelfinger et al. (2003)). Stimulus-dependent secretion occurs in a variety of cells including specialized mammalian cells such as neurons, β-cells of the pancreas, and mast cells, and methods for the production of recombinant proteins that rely on regulated secretion are known (e.g., U.S. Pat. No. 6,087,129; U.S. Pat. No. 6,110,707; U.S. Pat. No. 6,194,176; Grampp et al. (1992); Chen et al. (1995); Yang and Hsieh (2001)). These methods are drawn to the use of mammalian cells, and require that the gene for a protein that normally occupies the secretory granules (for example, insulin) be deleted and replaced by a gene for the recombinant protein (for example, prolactin) engineered to traffic to the same organelles.

Like some specialized metazoan cells *T. thermophila* also possesses a regulated secretion pathway in which targeted proteins form dense core granules, called mucocysts, that become docked to the plasma membrane. Ciliates engage in regulated secretion of proteins stored in cortical secretory organelles (granules), which are discharged in a stimulus-dependent or regulated fashion (Turkewitz et al. (2000);

Turkewitz (2004)). In *Tetrahymena* spp., these dense core granules are termed mucocysts. Each *Tetrahymena* spp. cell contains numerous mucocysts docked at the plasma membrane. Upon stimulation, the discharge of the mucocyst contents occurs in a rapid and synchronous manner (Satin (1977)). The signal sequences that target proteins to the dense core granules are not yet well-characterized, but small stable loops appear to be important determinants in several systems (Chanat et al. (1993); Cool et al. (1995); Cool et al. (1997); Glombik et al. (1999); Roy et al. (1991); Zhang et al. (1999)), and the sequences are readily identified by deletion analysis.

In contrast with constitutive secretion, regulated secretion can be triggered by the presence of chemical mediators known as secretagogues. Such mediators can cause increased levels of intracellular calcium ($Ca^{2+}$), which, in turn, triggers fusion of cortical granules with the plasma membrane and release of the granules contents into the surrounding extracellular space. Exposure of competent *T. thermophila* to secretagogues, thereby inducing an increase in cytosolic calcium, results in a rapid discharge of mucocyst contents to the extracellular space. Depending on the level of the stimulus, regulated secretion can be an all or none phenomenon. In some cases, relatively large amounts of protein can be released within a period on the order of milliseconds.

The endogenous proteins stored by ciliates are distinctive in terms of their structures and ability to self-associate upon granule discharge. Whereas the proteins released naturally by mammalian cells are typically soluble following exocytosis, the majority of proteins discharged from storage granules of ciliates self-associate, forming large macromolecular aggregates in the form of a proteinaceous gel.

Tetrahymenids and *Paramecium* belong to the Oligohymenophoreans. Ciliates that include mucocysts useful in the invention include *Tetrahymena* species such as *T. thermophila* and *T. pyriformis*. *Paramecium* has dense core granules but does not secrete a proteinaceous gel. Both *T. thermophila* and *T. pyriformis* produce mucocysts, and both secrete a proteinaceous gel.

The invention may be practiced with a variety of different ciliates that have secretory granules. Heterologous polypeptides can be targeted to these secretory granules by encoding fusion proteins of the desired heterologous polypeptide and an appropriate targeting sequence. After exposing the ciliate to a secretory stimulus that causes the mucocysts to discharge their contents to the extracellular environment, the heterologous polypeptide can be recovered from the resulting matrix and medium.

Genetic constructs encoding the fusion proteins described herein can readily be prepared by one of skill in the art based upon the universal genetic code, and optionally employing the codon preferences characteristic of the ciliate host. See, Larsen et al. (1999); Wuitschick and Karrer (1999); Wuitschick and Karrer (2000); and Eisen et al. (2006).

The nucleic acid sequences can be cloned using standard cloning procedures in the art, as described by Sambrook et al., Molecular Cloning: A Laboratory Manual, Second Edition, Cold Springs Laboratory, Cold Springs Harbor, N.Y. (1989). For example, chimeric genes encoding the fusion proteins can be generated by linking coding regions of genes for the heterologous polypeptides to endogenous mucocyst targeting sequences (or mucocyst protein fragments or entire mucocyst proteins) either synthetically (Lin et al. (2002)), or by PCR using serial overlap extension. The resulting constructs can then introduced into standard plasmid DNA vectors (e.g., TOPO, BlueScript, etc.) for amplification in *E. coli* by chemical transformation, electroporation or any other method known in the art.

Heterologous nucleic acids can be introduced into the ciliate host on an expression vector that is capable of integrating into the host's genome. For example, expression vectors capable of homologous recombination with a highly expressed gene that is endogenous to the protozoan host, such as a β-tubulin gene are known in the art. Alternatively, a heterologous nucleic acid transformed into a ciliate can be maintained extrachromosomally on an autonomous plasmid or chromosome.

Expression vectors useful for transforming ciliates in accordance with the methods described herein include but are not limited to replacement vectors, ribosomal DNA vectors, and ribosomal DNA-based vectors. Replacement vectors accomplish DNA-mediated transformation by replacing or altering endogenous genes using homologous recombination. Integration of the heterologous nucleic acid into the host's genome at the targeted site is accomplished via homologous recombination involving a double crossover event with the vector containing the heterologous nucleic acid. An example of an expression vector useful for genomic incorporation of a heterologous nucleic acid by replacement is one that includes a heterologous coding sequence flanked by portions of the endogenous BTU1 gene of *T. thermophile*.

A replacement vector can include a 5' region, followed by a heterologous coding region, followed by a 3' region, wherein at least a portion of each of the 5' and 3' regions is complementary to 5' and 3' regions on an endogenous gene of the host, to allow for genomic integration of the heterologous coding region via homologous recombination. The 5' and 3' regions of the vector can also comprise regulatory elements, such as a promoter and a terminator. The necessary regulatory elements can also be supplied by the endogenous gene into which the heterologous coding region integrates. Suitable regulatory regions include, but are not limited to promoters, termination sequences, signal peptides and proprotein domains involved in the expression and secretion of proteins. For example, such regulatory elements can provide efficient heterologous expression of proteins in *Tetrahymena* spp. under control of promoters and/or terminators which are derived from genes in *Tetrahymena* ssp. Such vectors can comprise naturally occurring promoters and/or terminators from proteins secreted at a high level in *Tetrahymena* ssp. The expression of recombinant polypeptides in *Tetrahymena* spp. can be driven by strong promoters, pre/pro sequences and terminators. In certain embodiments, the promoters and/or terminators can be selected from proteins secreted at a high level independent of the cell-cycle in *Tetrahymena* spp. (US Patent Application 2006/0127973; WO2003/078566). Inducible promoters from *Tetrahymena* spp. genes have also been described that allow robust expression of foreign genes. For example, heat-inducible promoters of the heat shock protein family of the ciliate *Tetrahymena* spp. are also suitable for use with the methods described herein. Suitable heat shock promoters from *Tetrahymena* spp. are known in the art (see for example, WO2007/006812).

Methods for creating mitotically stable *Tetrahymena* spp. transformants, for example, by integration of a heterologous gene by homologous DNA recombination, are known in the art. Methods for generating *Tetrahymena* spp. having targeted gene knockouts by homologous DNA recombination are also known in the art (Bruns and Cassidy-Hanley (2000); Hai et al. (2000) 514-531; Gaertig et al. (1999); Cassidy-Hanley et al. (1997)). The somatic macronucleus or the generative micronucleus can be transformed in alternation.

For example, sterile transformants, which may provide improved safety parameters, can be obtained with macronucleus transformation.

Expression vectors can also be maintained extrachromosomally in the ciliates. An expression vector maintained as an extrachromosomal element can be a ribosomal DNA-based vector containing an on from *Tetrahymena* spp. ribosomal DNA, which is known to support extrachromosomal replication. Such a vector can further comprise a 5' regulatory region from an endogenous *Tetrahymena* spp. gene containing a promoter region operably linked to the heterologous coding region and, optionally, a 3' regulatory region from the same or a different *Tetrahymena* spp. gene. For example, regulatory regions from ciliate genes in such vectors can include, but are not limited to, regulatory regions from genes such as HHFI, rp129, BTU1, BTU2, SerH3, and actin.

There are a number of suitable vectors suitable for transformation of ciliates known in the art. For example, *Tetrahymena* spp. can be transformed with an ribosomal DNA vector (Tondravi and Yao (1986); Yu and Blackburn (1989)). The shuttle vector pXS76 allows insertion of transgenes downstream of a cadmium-inducible promoter from the MTT1 metallothionein gene of *T. thermophile* via homologous recombination and selection in paromomycin. Alternatively, inserts can be introduced into high copy number ribosomal DNA vectors (such as pD5H8) under control of the cadmium-inducible MTT1 promoter. The pD5H8 vector takes advantage of a biological feature of *Tetrahymena* spp. in which the ribosomal cistrons become amplified to extraordinarily high copy numbers following conjugation. A ribosomal DNA-based vector can be a circular vector that contains a 5' non-translated sequence comprising two or more ori sequences from *Tetrahymena* spp. ribosomal DNA. A nucleic acid fragment containing a heterologous coding region, for example a selectable marker or transgene, can also be added to the vector. The vector can further comprise a 5' untranslated region of a *Tetrahymena* spp. gene and a 3' untranslated region of a *Tetrahymena* spp. gene, inserted upstream and downstream of the selectable marker and/or the transgene. Methods for transformation, along with robust, inducible promoters for driving high-level gene expression have recently been described for this system (Bruns and Cassidy-Hanley (2000); Gaertig and Kapler (2000); Shang et al. (2002); Boldrin et al. (2006)).

The sequences encoding the fusion protein can be introduced into the cells on expression plasmids, or can be stably integrated into the protist genome (e.g., by homologous recombination, retroviral insertion). When integrated into the genome, the fusion protein sequences can replace (in whole or in part) the endogenous sequences encoding the corresponding mucocyst protein, or can be inserted at a separate genomic location. Targeting sequences useful for secretion of foreign proteins in *Tetrahymena* spp. are described in (Clark et al. (2001)).

Genes can be introduced into ciliates using established protocols or any method known to one skilled in the art. Transformation of ciliates can be achieved by microinjection (Tondravi and Yao (1986)), electroporation (Gaertig and Gorovsky (1992)), or biolistically (Cassidy-Hanley et al. (1997)).

Thus, in some embodiments, ciliate cells can be transformed with a chimeric gene by particle bombardment (also known as biolistic transformation) (Cassidy-Hanley et al. (1997)). Particle bombardment transformation can be achieved by several ways. For example, inert or biologically active particles can be propelled at cells under conditions effective to penetrate the outer surface of the cell and to be incorporated within the interior thereof. When inert particles are utilized, the vector can be introduced into the cell by coating the particles with the vector containing the chimeric gene. Alternatively, the target cell can be surrounded by the vector so that the vector is carried into the cell by the wake of the particle. Other variations of particle bombardment, now known or hereafter developed, can also be used.

Microcarrier bombardment can also be used to transform ciliate cells by means of DNA-loaded gold particles (U.S. Pat. No. 6,087,124; European Pat. EP 847 444; WO 1998/001572; Cassidy-Hanley et al. (1997), Genetics 146:135-147). In this approach, microcarrier bombardment with DNA-coated gold is used as a means of introducing foreign genes into ciliates. In certain embodiments, microcarrier bombardment can be used to transform ciliates and introduce genes into the (germline) micronucleus Methods for selection of transformed cells harboring foreign genes are known in the art. For example, the vector can further comprise a selectable cassette marker to permit selection for transformed cells (e.g., a neo 2 cassette) (Gaertig et al. (1994)). Selection of transformants can be achieved by growing the cultured ciliates in a medium which allows only the transformants to survive. Suitable selection agents include antibiotics which will kill most all non-transformants but allow transformants (which also possess an antibiotic resistance gene) to survive. A number of antibiotic-resistance markers are known in the art. Any known antibiotic-resistance marker can be used to transform and select transformed host cells in accordance with the present invention. For example, selection of the transformants can be performed by means of a resistance marker such as a point mutation in the 17s rDNA, which confers resistance to paromomycin, can allow for selection of rDNA transformants (Spangler and Blackburn (1985); Bruns et al. (1985)). Other methods include the use of a mutant cell line that allows targeting of genes to the β tubulin-1 locus of *T. thermophila* by homologous recombination, and allows efficient selection of transformed cell lines by growth in the microtubule-stabilizing agent (taxol) (U.S. Pat. No. 6,846,481). Another method for selection of transformed cells harboring foreign genes is to insert full length coding regions into the pD5H8 vector (Cowan et al. (2005)). In this method, transcription is driven by the inducible MTT1 promoter. Once cells have been transformed with the pD5H8 vector selection of positive transformants is determined by paromomycin resistance (i.e., cell growth in media containing the drug). Presence of the transgene is then verified by PCR and then induced with cadmium chloride to overexpress the recombinant gene product.

Many other selectable marker systems are known in the art. Selectable marker genes that confer resistance or tolerance to a normally toxic selection agent allow only successfully transfected cells to survive in the presence of the selection agent, and are referred to as positive selectable markers. Examples of positive selectable marker genes and their corresponding selection agents are: aminoglycoside phosphotransferase (APH) and G418; dihydrofolate reductase (DHFR) and methotrexate (Mtx); hygromycin-B-phosphotransferase (HPH) and hygromycin-B; xanthine-guanine phosphoribosyltransferase (XGPRT) and mycophenolic acid; and adenosine deaminase (ADA) and 9-β-D-xylofuranosyl adenine (Xyl-A). In another example of a positive selectable marker system, thymidine kinase (TK) and aminopterin (included, e.g., in hypoxanthine-aminopterin-thymidine (HAT) medium) can be used in cells that are initially thymidine kinase deficient (tk⁻). The aminopterin will normally kill tk⁻ cells and, therefore, only successful TK transfectants will survive. Selectable marker genes that confer sensitivity or susceptibility to a normally non-toxic selection agent cause only successfully transfected cells to die in the presence of the selection agent, and are referred to as negative selectable markers. An example of a negative selectable marker system is thymidine kinase (TK) and gancyclovir. Phenotypic selectable marker genes permit selection based upon morphological or biochemical traits rather than cell death or survival. In some cases, the phenotypic marker is detectable only in the presence of an additional selection agent. An example of a phenotypic selectable marker system is β-galactosidase (lacZ) and X-gal.

Assembly of Granular Protein Particles of Grl/Ag Fusion Proteins

Although the crystalline arrays formed by Grls in dense core granules may comprise as many as nine different Grls, as well as additional protein and non-protein components, and are formed by a multistep process that involves trafficking and processing of the Grls (and presumably other dense core granule components) to multiple cell compartments (i.e., endoplasmic reticulum, trans-Golgi, dense core granule), it has surprisingly been found that a purified or partially purified preparation of Grl/Ag fusion proteins, obtained from cell lysates or regulated secretion, can be induced to self-assemble into granular protein particles upon addition of a sufficient concentration of divalent cations to the medium or by reduction of the pH to acidic levels (e.g., below 6.0).

It has also been found that the Grl/Ag fusion proteins described herein can undergo aggregation in a medium either (a) in the form of an isolated and purified or partially purified preparation of a single Grl/Ag fusion protein or (b) in a homogenous mixture comprising one or more additional Grl/Ag proteins and/or Grl proteins The concentration of divalent cation required to induce aggregation of a Grl/Ag fusion protein can be readily determined by increasing the concentration of divalent cations in a medium comprising the Grl/Ag fusion protein until aggregation of the Grl/Ag fusion protein and/or the formation of particles comprising the Grl/Ag fusion protein occurs. One can readily determine the extent of aggregation by determining or visualizing the formation of particulate matter in the medium. In certain embodiments, the divalent cation is a $Ca^{2+}$. In certain embodiments, the divalent cation is $Mg^{2+}$. In certain embodiments, the divalent cation is selected from the group comprising $Mn^{2+}$, $Co^{2+}$, $Cd^{2+}$, $Zn^{2+}$, $Cu^{2+}$, $Cd^{2+}$, $Sr^{2+}$, $Ba^{2+}$, $Ni^{2+}$, $Fe^{2+}$, $Hg^{2+}$, $Pb^{2+}$, and $Cr^{2+}$. In certain embodiments, the divalent cation concentration in a medium sufficient to induce aggregation of a Grl/Ag fusion protein will be at least about 0.01 mM, at least about 0.05 mM, at least about 0.2 mM, at least about 0.5 mM, at least about 1 mM, at least about 2 mM, at least about 5 mM, at least about 10 mM, at least about 20 mM, at least about 30 mM, at least about 50 mM, at least about 75 mM, at least about 100 mM, at least about 150 mM, at least about 200 mM, or at least about 500 mM. In certain embodiments, one or more divalent cations can be combined to achieve a divalent cation medium concentration sufficient to induce aggregation of a Grl/Ag fusion protein.

It has also been found that the rate of aggregation of the Grl/Ag fusion proteins can be controlled with the addition of chelators (e.g., EGTA) to the medium so as to reduce the divalent cation concentration. Similarly, in embodiments where chelators have been added to the medium, additional divalent cations can be added to the medium to further control the rate of aggregation.

The concentration of chelator (e.g., EGTA) required to inhibit assembly of Grl/Ag fusion proteins can be readily determined by adding chelator to a medium comprising the Grl/Ag fusion protein. In certain embodiments, in the absence of added divalent cations (i.e., including only divalent cation concentrations present in a cell, cell lysate or standard growth medium), the concentration of chelator (e.g., EGTA) required to inhibit assembly of Grl/Ag fusion proteins can be less than about 0.01 mM, less than about 0.05 mM, less than about 0.2 mM, less than about 0.5 mM, less than about 1 mM, less than about 2 mM, less than about 5 mM, less than about 10 mM, less than about 20 mM, less than about 30 mM, less than about 50 mM, less than about 75 mM, less than about 100 mM, less than about 150 mM, less than about 200 mM, or less than about 500 mM.

Any method known in the art to reduce the concentration of a free divalent cation can be used in connection with the methods and compositions described herein. For example, reduction of free divalent cation concentration in a medium can be achieved with divalent cation chelators (e.g., EDTA, EGTA, and BAPTA). In certain embodiments, the amount of a divalent cation chelator required to solubilize an aggregated Grl/Ag fusion protein will be at least about 0.01 mM, at least about 0.05 mM, at least about 0.1 mM, 0.2 mM, at least about 0.5 mM, at least about 1 mM, at least about 2 mM, at least about 5 mM, at least about 10 mM, at least about 20 mM, at least about 30 mM, at least about 50 mM, at least about 75 mM, at least about 100 mM, at least about 150 mM, at least about 200 mM, or at least about 500 mM. Other methods known in the art can also be used to reduce the concentration of free divalent cations in a medium, including, but not limited to dialysis, chromatography, gel filtration and the like.

It has also been found that self-assembly of Grl/Ag proteins into granular protein particles can be induced by decreasing the pH to acidic levels, and that aggregated forms of the Grl/Ag fusion protein can be induced to deaggregate upon increase of the pH to less acidic, neutral or basic levels.

In certain embodiments, the pH of a medium sufficient to induce aggregation of a Grl/Ag fusion protein will be at least about 3.0, at least about 3.2, at least about 3.4, at least about 3.6, at least about 3.8, at least about 4.0, at least about 4.2, at least about 4.4, at least about 4.6, at least about 4.8, at least about 5.0, at least about 5.2, at least about 5.4, at least about 5.6, at least about 5.8, or at least about 6.0. In certain embodiments, the pH of a medium can be adjusted in combination with the addition of one or more divalent cations to induce aggregation of a Grl/Ag fusion protein.

Immunogenic Granular Protein Particles and Uses Thereof

In certain aspects, the invention relates to granular protein particle compositions comprising Grl/Ag fusion proteins in which the Ag moiety includes an immunogenic polypeptide. In certain embodiments, the invention relates to such compositions comprising Grl/Ag fusion proteins produced according to the methods described herein. The compositions comprising Grl/Ag fusion proteins can be used to induce or increase an immune response against at least one epitope of the immunogenic polypeptide in an animal.

Once obtained, the particulate compositions described herein can be incorporated into immunogenic or vaccine compositions. In certain embodiments, the particulate compositions comprising Grl/Ag fusion proteins are the sole active components of the vaccine compositions. In other embodiments, the particulate compositions comprising Grl/Ag fusion proteins can further comprise additional proteins or biomolecules, including but not limited to endogenous secreted proteins (e.g., Grl proteins), endogenous cytoplasmic proteins or other cellular components that leak into the medium, or exogenously produced proteins or biomolecules that are intentionally added to the composition for various purposes (e.g., adjuvants).

In certain embodiments, the granular protein particle compositions, as described herein, can comprise two or more different Grl/Ag fusion proteins. In such embodiments, the purified fusion proteins can be mixed together at specific molar ratios prior to inducing particle formation. In embodiments where a particulate composition comprises two or more different Grl/Ag fusion proteins, the Grl moieties of the two or more different Grl/Ag fusion proteins can be derived from the same Grl protein or they can be derived from different Grl proteins. Alternatively, or in addition, in embodiments where a particulate composition comprises two or more different Grl/Ag fusion proteins, the Ag moieties of the two or more different Grl/Ag fusion proteins can be derived from the same heterologous polypeptide or from different heterologous polypeptides. In some embodiments where a particulate composition comprises two or more different Grl/Ag fusion proteins, the Ag moieties of the two or more different Grl/Ag fusion proteins can be from the same organism or from different organisms or pathogens (e.g., viruses or bacteria). For example, in one embodiment, a particulate composition made according to the methods described herein can be a particulate composition comprising HA-Grl1 and Flagellin-Grl4.

Without being bound by any particular theory, in embodiments where a particulate composition comprises two or more different Grl/Ag fusion proteins, the composition can be suitable for use as a multivalent immunogen because it will comprise two or more different antigens. For example, in certain embodiments where a particulate composition comprises two or more different Grl/Ag fusion proteins, the Ag moieties of the two or more different Grl/Ag fusion proteins can be from the same protein of a pathogen (e.g., a viral envelope protein). Alternatively, in embodiments where a particulate composition comprises two or more different Grl/Ag fusion protein, the Ag moieties of the two or more different Grl/Ag fusion proteins can be from different proteins of a pathogen pathogen (e.g., a viral envelope protein and a polymerase protein from the same virus). Similarly, in embodiments where a particulate composition comprises two or more different Grl/Ag fusion proteins, the Ag moieties of the two or more different Grl/Ag fusion proteins can be from different proteins from different pathogens (e.g., viral envelope proteins from different viruses).

Without being bound be any particular theory, in certain embodiments where a granular protein particle composition comprises two or more different Grl/Ag fusion proteins, the Ag moieties of the two or more different Grl/Ag fusion proteins can be proteins that have different functions when in a particulate composition. For example, in certain embodiments, at least one Ag moiety from the two or more different Grl/Ag fusion proteins can be an antigen whereas another Ag moiety from the two or more different Grl/Ag fusion proteins can be an be an immunomodulatory protein (e.g., interferon-$\gamma$, or a biologically active fragment thereof, or Flagellin, or a biologically active fragment thereof).

In embodiments where a particulate composition comprises two different Grl/Ag fusion proteins, the molar ratios of the two Grl/Ag proteins in the particulate composition can be, about 22:1 or greater, about 20:1, about 18:1, about 16:1, about 14:1, about 12:1, about 10:1, about 8:1, about 6:1, about 4:1, about, 2:1, about 1:1, about 1:2, about 1:4, about 1:6, about 1:8, about 1:10, about 1:12, about 1:14, about 1:16, about 1:18, about 1:20, or about 1:22 or less. In embodiments where a particulate composition comprises more than two different Grl/Ag fusion proteins, the molar ratio of each of the different Grl/Ag fusion proteins in the particulate composition can be adjusted according to any ratio suitable for inducing particle formation. In some embodiments, the ratio of two or more Grl/Ag fusion proteins can be the same and the ratio of one or more other Grl/Ag fusion proteins can be higher than other Grl/Ag fusion proteins having the same molar ratio. In some embodiments, the ratio of two or more Grl/Ag fusion proteins can be the same and the ratio of one or more other Grl/Ag fusion proteins can be lower than other Grl/Ag fusion proteins having the same molar ratio.

The methods described herein enable a practitioner to produce the particulate compositions described herein for a variety of treatment purposes or prophylactic purposes including, but not limited to immunization against pathogens, the treatment of cancers and the production of antigen specific antibodies.

In certain embodiments, the particulate compositions comprising Grl/Ag fusion proteins described herein are aggregated particles that resemble and in certain embodiments comprise the immunogenic properties of virus like-particles. For example, the particulate compositions described herein need not be pathogenic or infectious and can be produced according to the methods described herein, and can be purified and/or administered in a form lacking genomic material. Further, like VLPs, in some embodiments, the particulate compositions described herein can be produced in large amounts and readily purified for use as immunogenic particles.

In certain aspects, the particulate compositions described herein can be used as immunostimulatory substances and can be useful for inducing or increasing an immune response in an animal. Further, the particulate compositions described herein can also be combined with a variety of pharmaceutically acceptable materials or carriers, including but not limited to diluents, encapsulating materials, solid fillers, liquid fillers, or adjuvants suitable for administration in an animal. The pharmaceutically acceptable materials or carriers can be from any source and can be from organic, inorganic, natural or synthetic sources.

In certain aspects, the invention provides methods for vaccination mediated prevention or attenuation of disease conditions or viral infections in animals. In certain embodiment, the invention provides vaccines for the prevention or attenuation of disease conditions or viral infections in a variety of mammals, including, but not limited to humans, monkeys, cows, dogs, cats, horses, pigs and the like.

When used as immunogenic compositions, the particulate compositions described herein can be used for the prevention or attenuation of diseases or infectious conditions. In certain embodiments, the invention provides for a vaccine composition comprising a particulate composition comprising a Grl/Ag fusion protein. The vaccine compositions of the invention can comprise an immunologically effective amount of the particulate compositions described herein and can optionally further comprise diluents, carriers, excipients or carriers. Examples of materials suitable for use in preparing pharmaceutical compositions are provided in numerous sources including *Remington's Pharmaceutical Sciences* (Osol, A, ed., Mack Publishing Co., (1990)). Thus, in certain embodiments, the invention provides a vaccine comprising an immunologically effective amount of a particulate composition comprising a Grl/Ag fusion protein, optionally in combination with a pharmaceutically acceptable diluent, adjuvant, carrier or excipient.

Any adjuvant known in the art can be used to increase the immunological response of compositions comprising the Grl/Ag fusion proteins described herein, including, but not limited to Freund's adjuvant, mineral gels (e.g., aluminum hydroxide), surface active substances (e.g., lysolecithins), pluronic polyols, polyanions, peptides, oil emulsions, keyhole limpet hemocyanins, dinitrophenol. Other adjuvants suitable for use with the methods and compositions described herein include, human adjuvants such as BCG (Bacille Calmette Guerin) and *Corynebacterium parvum*. Other suitable adjuvants include, but are not limited to, Monophosphoryl lipid immunomodulator, AdjuVax 100a, QS 21, QS 18, CRL1005, Aluminum salts, MF 59, and Virosomal adjuvant technology. The adjuvants can also comprise a mixture of these substances.

Administration of the compositions described herein can be achieved by any method known in the art, however in some circumstances, the method of administration may depend on the desired effect, the nature of the composition (e.g., the identity of the Grl/Ag fusion proteins comprised within the particulate compositions), the condition or infection being treated, and the desired dosage. Suitable modes of administration include, but are not limited to oral, rectal, parenteral, intracisternal, intravaginal, intraperitoneal, topical or bucal administration. In certain embodiments, the particulate compositions described herein can also be administered in the form of an oral or nasal spray. As used herein, the term "parenteral" can refer to intraperitoneal, intramuscular, subcutaneous, intra-articular, intravenous or intrasternal infusion or injection.

The particulate compositions described herein can also be prepared in unit dosage forms according to any method known in the art. In certain embodiments, the particulate compositions described herein can be in the form of discrete units (capsules or tablets) wherein each unit comprises a determined amount of one or more particulate composition comprising a Grl/Ag fusion protein. Alternatively, the particulate compositions described herein can be provided in the form of a liquid suspension such as an aqueous liquid or non-aqueous liquid (e.g., an emulsion, an elixir, or a syrup). Many other types of dosage forms are known in the art, and one of skill in the art will be readily capable of determine suitable methods of administering the particulate compositions described herein.

Sub-unit vaccines can comprise a defined antigen (e.g., a recombinant protein) and can be produced in any of a number of expression host cells including mammalian, yeast, insect and bacterial cells. Sub-unit vaccines have advantages over traditional attenuated or killed pathogen based vaccines. For example, because many expression host cells can be grown at scale, recombinant proteins can be produced at high yield. This feature of expression host systems can circumvent production difficulties associated with traditional attenuated or killed pathogen based vaccines. Further, advances in recombinant DNA technology enable recombinant expression systems that are better suited to be rapidly mobilized in response to pandemic threats. Additionally, because the pathogen itself is not utilized in actual production of the vaccine, sub-unit antigens are considerably safer than live or killed vaccines.

Lack of potency has been a major hurdle with the use of subunit vaccines. For example, because sub-unit vaccines do not always elicit the "danger signals" associated with whole killed or attenuated pathogens, sub-unit vaccines are often formulated in combination with chemical adjuvants. These adjuvants stimulate the immune system to respond to the recombinant antigen component of the formulation.

One approach to attempt to increase the potency of subunit vaccines is Virus-like particle (VLP) technology. Certain VLP approaches are based on expression of virus capsid genes to promote the spontaneous assembly of virus-like particles. Despite the fact that they lack genetic material (either DNA or RNA) and are therefore not capable of replication, VLPs nevertheless adopt an overall virus-like structure. Without wishing to be bound by theory, it is believed that this virus-like structure of VLPs render them capable of eliciting strong humoral and cell mediated responses characterized by CD4+ T-helper and CD8+ cytotoxic T lymphocyte responses. The ability of VLPs to induce strong responses reduces the need to administer large amounts of antigen on order to produce a protective effect. Further, because they are recombinant entities and because VLPs can be formed following expression in currently available host-cell systems such as yeast, mammalian and insect cells, VLPs can maintain the productivity and safety advantages associated with sub-unit vaccines. A number of VLP based vaccines are currently under development for the prevention of a range of human and animal disease including HIV, SARS, Influenza and Bluetongue virus and a few have been approved for use in humans. For example, Gardasil (Merck & Co.) prevents infection of certain types of human papillomavirus (HPV), a major cause of cervical cancers. Although VLP technology has been applied to the development of vaccine candidates for a broad range of viruses, use of the technology is restricted to the development of vaccines against viral borne disease.

In certain aspects, the invention described herein relates to the finding that Grl fusion technology can be applied to the production of immunogenic granular protein particles by expression of mucocyst-targeted fusion proteins comprising a polypeptide of interest and a mucocyst-targeting moiety (e.g., Grl1). In certain embodiments, mucocyst-targeting moiety directs the trafficking of the fusion protein to the mucocysts of a ciliate.

Ciliate Grl proteins are distinctive in their ability to self-associate upon granule discharge. Whereas the proteins released naturally by mammalian cells are soluble following exocytosis, the majority of proteins discharged from storage granules of ciliates self-associate, forming large macromolecular aggregates. Upon secretion, the Grl fusion proteins become incorporated into the crystalline lattice of the secreted gel in the form of a particulate material. The self-association properties of the Grl fusion proteins described herein enables their isolation and processing to form self-assembled immunogenic particles independent of the natural mechanisms involved in maturation of *Tetrahymena* spp. dense core granules.

Due to the particulate nature of the lattice and the repetitive presentation of antigen, the particulate compositions described herein are highly immunogenic and induce powerful humoral and cellular immune responses. Electron microscopy shows that the secreted gel is composed of repeating units (FIG. 1). The granular particles described herein have very similar dimensions to VLPs and range in diameter from about 20 to about 200 nm. In some embodiments, the invention provides a compositions of granular protein particles in which 50%, 60%, 70, 80% or 90% of the particles are between 20 to about 200 nm. This particulate material can be utilized directly as a vaccine delivery system. In certain embodiments, the method comprises a step of induces self-assembly of the insoluble particles from purified fusion proteins.

The following examples illustrate some preferred modes of practicing the present invention, but are not intended to limit the scope of the claimed invention. Alternative materials and methods may be utilized to obtain similar results.

EXAMPLES

Example 1

Figure 2:

Assembly of Immunogenic Particles from a Purified Source of *P. Falciparum* 48/45-Grl1 Fusion Protein Gene Construct Design, Synthesis and Cloning: A synthetic gene was designed wherein the coding region of the *Plasmodium falciparum* gametocyte specific cell surface transmission blocking antigen pfs48/45 containing a HA epitope tag was fused proximal to the *T. thermophila* Grl1 gene lacking the native amino terminal Pre domain but additionally containing a carboxy-terminal 10× His tag (FIG. 2). The chimeric gene was synthesized and cloned into a somatic expression vector, pTIEV4, via BamHI and SacI restriction sites engineered into the 5' and 3' ends of the synthetic gene, respectively. Transcription of the transgene was under the control of a cadmium-inducible promoter from the metallothionein-5 (MTT5) gene of *T. thermophila*. The expression construct comprising MTT5 promoter, chimeric transgene, MTT1 terminator and a neomycin resistance cassette were transferred, en masse, as a NotI fragment into a high-copy rDNA vector, pD5H8 and introduced into conjugating *T. thermophila* strains by biolistic transformation.

The complete amino acid sequence of the pfs48/45 protein is shown in SEQ ID NO: 10. The complete amino acid sequence of the pfs48/45-Grl1 fusion protein is shown in SEQ ID NO: 11. The portion of pfs48/45 used in the Grl fusion is residues 159-426 of SEQ ID NO: 10, and residues 23-290 of SEQ ID NO: 11. This represents a truncated version of pfs48/45 (the "10C construct") that is based on the number of cysteine residues present in this part of the sequence. When expressed as a Grl fusion, this polypeptide can be detected by conformational specific antibodies, suggesting that it is folded correctly. A pfs 48/45-Grl1 fusion comprising the full-length version (the "16C construct") has been expressed but, to date, has not been detected by the same conformational specific antibodies. The sequence at residues 1-22 of SEQ ID NO: 11 is the signal peptide from the immobilization antigen variant B protein of *Ichthyophthirius multifiliis*, but includes a GS at positions 2-3 which is an artifact of a BamHI restriction site. At positions 291-296 there is an internal His 6× tag followed at positions 297-367 an immobilization antigen. These sequences were initially included as they may enhance protein stability, but this has not been confirmed, and they are not regarded as necessary to the construct. Residues 368-751 is the Grl moiety, which corresponds to residues 19-402 of SEQ ID NO: 1. Finally, at positions 752-761 there is a C-terminal His 10× tag for protein purification.

Generation of expression strains: B2086 and CU428 *T. thermophila* strains were grown in modified NEFF medium (0.25% proteose peptone, 0.25% yeast extract, 0.55% glucose, 33 mM $FeCl_3$) at 30° C. One hundred ml of each logarithmically growing culture was centrifuged at 1,100×g for 2 minutes in oil centrifuge tubes, washed in 10 mM Tris pH 7.4 and resuspended in fresh 10 mM Tris pH 7.4 (starvation medium) at a concentration of 200,000-250,000 cells/ml. Cells were incubated for 9-18 hours at 30° C. After starvation, B2086 and CU428 cell cultures were counted and cell concentration was readjusted to 200,000 cells/ml. To induce conjugation, 100 ml of each strain were mixed together in a 4 L flask. Four transformations were performed between 9.5 and 10.5 hours post-mixing using a Biolistic PDS-1000/He Particle Delivery System (BIO-RAD). For each transformation, 20 μl of M17 (BioRad) tungsten bead suspension in sterile water (60 mg/ml) were coated with 4 μg of DNA construct. Fifty ml of conjugating cells were concentrated to ~1 ml by centrifugation at 1,100×g in oil centrifuge tubes for 2 minutes. Cells were spread on a round 90 mm hardened paper filter (Whatman, Cat. #1450-090) pre-wet with 1.5 ml 10 mM Tris pH 7.4 inside a Petri dish. After the bombardment, the filter with the cells was transferred into a 500 ml flask containing 50 ml NEFF medium. The flasks were incubated on a slow shaker for ~20 hours at 30° C. At 30 hours post-mixing, 25 ml NEFF medium containing 300 μg/ml paromomycin was added to the 50 ml of cell culture (final paromomycin concentration, 100 mg/ml). Cells were aliquoted into 96 well microplates (150 μl per well). After 3-4 days, the microplates were examined and 5 μl from each of the wells containing paromomycin-resistant cells were transferred into 150 μl NEFF medium containing 100 μg/ml paromomycin on a master 96 well microplate.

Figure 3:
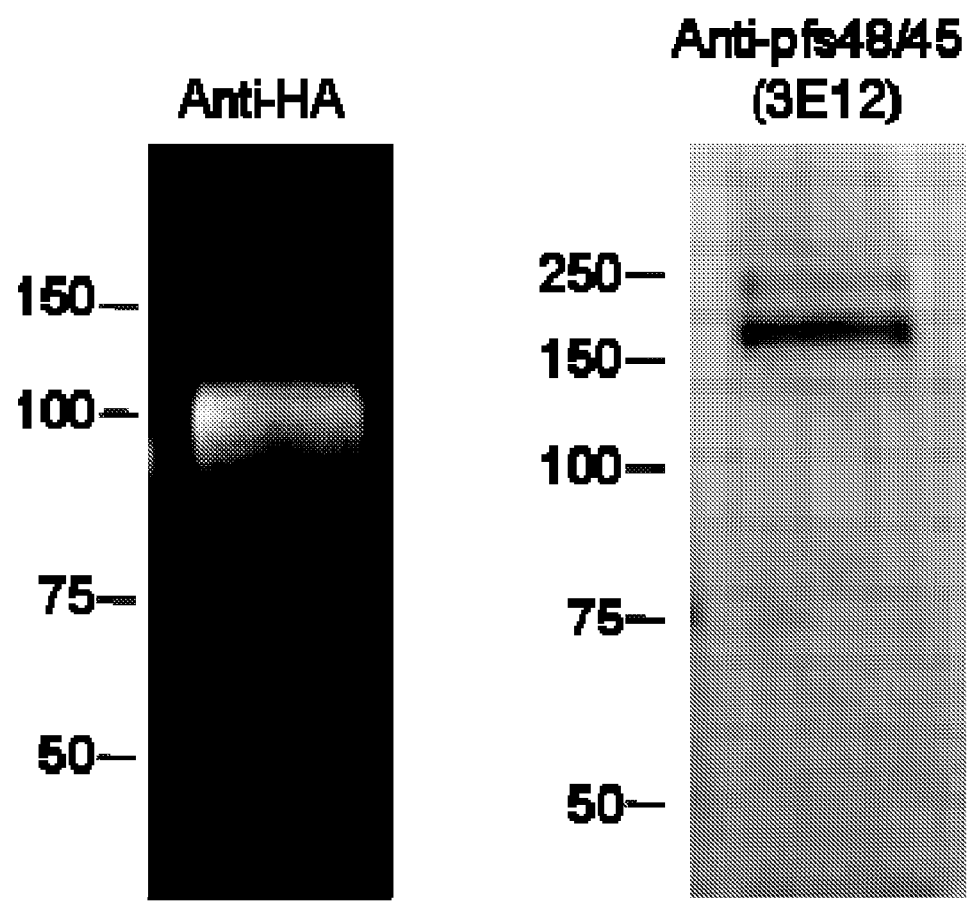

Western analysis: To evaluate 48/45-Grl1 expression, cultures were grown to ~5×10$^5$ cells/ml and induced for 12 hr with 1 μg/ml of $CdCl_2$. Cells were then harvested and lysed in SDS sample buffer in the absence of reducing agents. Proteins were resolved by SDS-PAGE and transferred to nitrocellulose membranes before Western blotting. Blots were probed with an anti-HA antibody that recognizes the linear HA epitope engineered into pfs48/45 and a transmission blocking antibody, 3E12. The 3E12 antibody recognizes conformational epitopes on pfs48/45 that are destroyed by treatment with disulfide reducing agents. Following incubation in primary antibody, blots were probed with secondary goat anti-mouse IgG coupled to HRP for visualization (FIG. 3).

Figure 4:
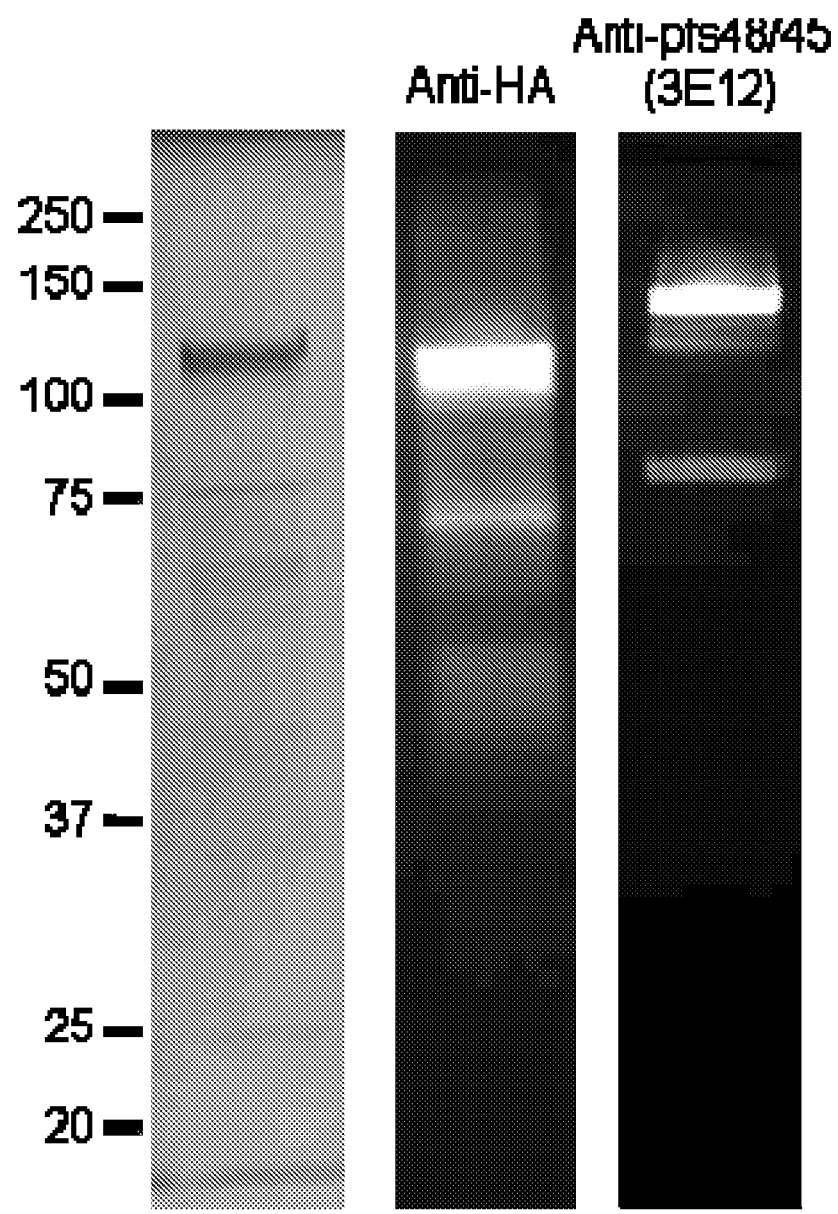

Purification of pfs48/45-Grl1: 1 ml of *Tetrahymena* stock culture transformed with Pfs48/45-GRL1 fusion protein was grown in 10 ml NEFF medium in a 30° C. shaking incubator until the culture reached mid-log phase (5×10$^5$ cell/ml). The next day the 10 ml culture was expanded to 500 ml and grown to stationary phase (1-1.5×10$^6$ cells/ml) at which point the cultures were diluted with fresh NEFF 1:1 and immediately induced with 1.5 ug/ml $CdCl_2$. Cells expressing recombinant Pfs48/45-GRL1 were harvested by centrifugation and cell pellets were frozen in the presence of protease inhibitors. Cell pellet containing 7.5×10$^8$ cells was diluted in TGN buffer (40 mM Tris, 50 mM NaCl, 10% Glycerol) containing 0.5% Tween 80 and brought up to final volume 350 ml. The lysate was incubated at 4° C. for 10-50 min after which it was centrifuged 50K×g for 30 min. Resulting pellets were kept and diluted in 500 ml final volume TGN Buffer containing 0.5% N-Lauryl-Sarcosine. The mixture was stirred at 4° C. for 1 hr and filtered using Milipore OpticapXL filter. 450 ml of post filter protein solution was loaded onto the Ni column pre-equilibrated with TGN buffer containing 0.5% Sarcosyl. After loading the column was washed with 5 column volume TGN 0.5% Sarcosyl, 5 column volume TGN 0.01% Tween80. The protein was eluted with 25-500 mM Imidazole gradient. Fractions containing protein of interest were dialyzed immediately in TGN 0.01% Tween80, 5 mM EGTA. Analysis of purified pfs48/45-Grl1 was carried out by SDS-PAGE and western analysis as shown in FIG. 4.

Assembly of pfs48/45-Grl1 particles and characterization by electron microscopy: For self-assembly experiments, 500 µl of concentrated purified protein was supplied with or without CaCl$_2$ to final concentration of 2 mM and incubated at 4° C. for 48 hrs. 10 µl of sample was put on a formvar and carbon coated Ni grid and left for 2 min. Following incubation the sample was withdrawn from the grid with a filter wick. The grids were stained with 10 µl of 2% Uranyl acetate for 1min, dried and examined with Technai 12 electron microscope (FIG. 5).

Figure 8:
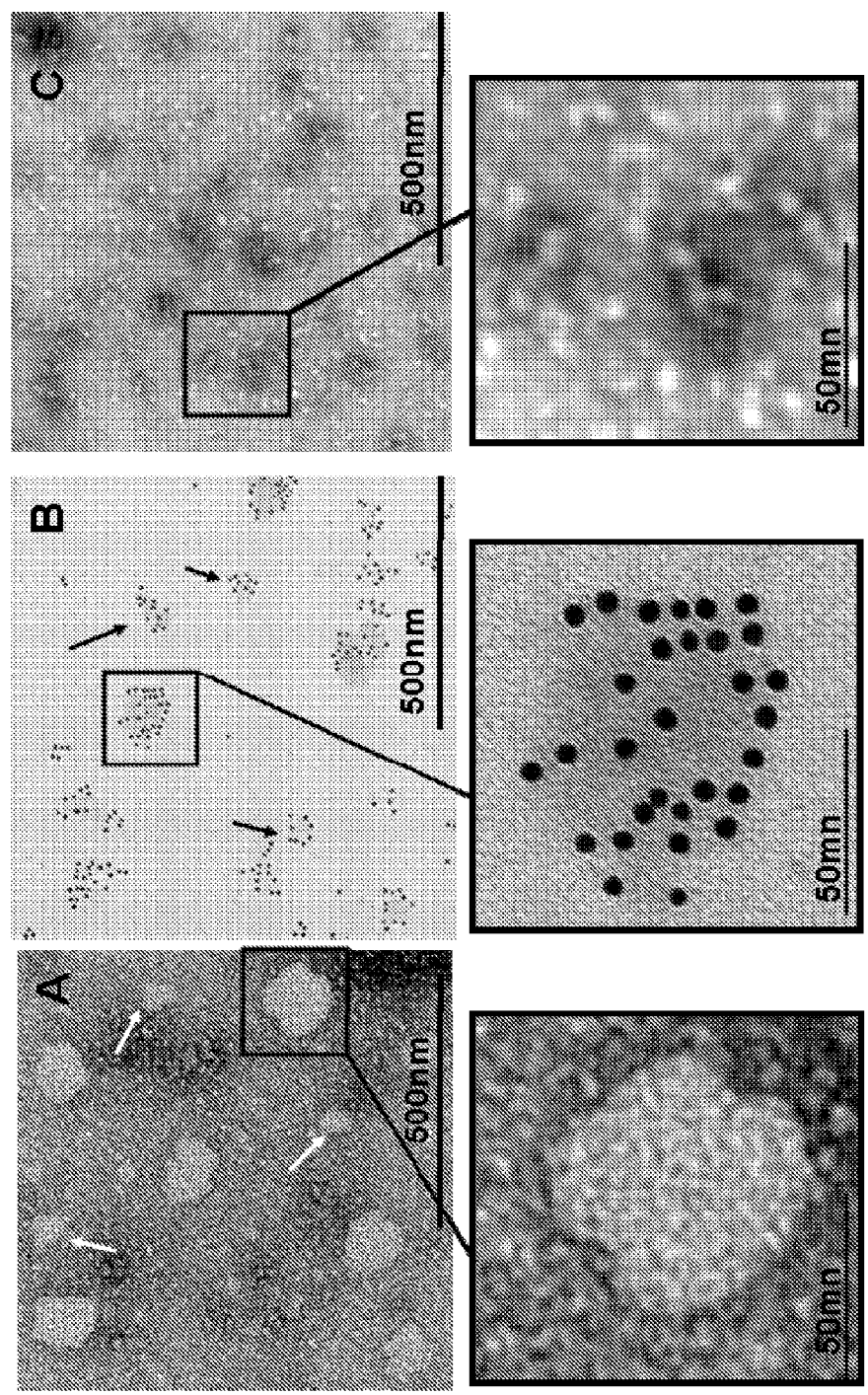

For immunogold labeling carbon-formvar coated grids containing assembled particles were incubated face down in 1% fish gelatin PBS (blocking buffer) drops for 1 hr at room temperature followed by incubation in anti-HA tag antibody solution diluted 1:1 in blocking buffer over night at 4° C. The next day the grids were washed 3×10 min each in 2× PBS and blocked for 10 min in 1% fish gelatin PBS. After blocking the grids were incubated in secondary antibody solution (anti-rabbit IgG labeled with 10 nm gold particles-Sigma) for 3 hr at room temperature and washed 3× in PBS 5 min each and 1× in H$_2$O followed by staining in 1% Uranyl Acetate for 30 sec. Assembled particles were visualized using Technai 12 transmission electron microscope, HV=100.0 kV, direct magnification ~100,000×. The results are shown in FIGS. 8b. As a control 10 µl of purified concentrated protein was put on a formvar-carbon coated grid and labeled with uranyl acetate as described above (FIG. 8C).

Figure 6:
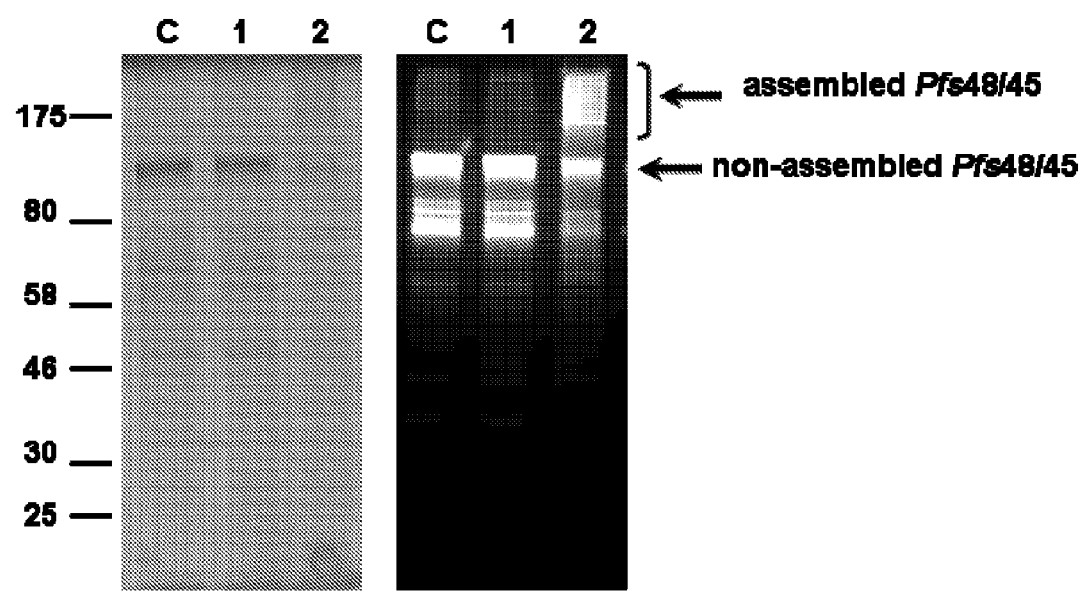
Figure 7:
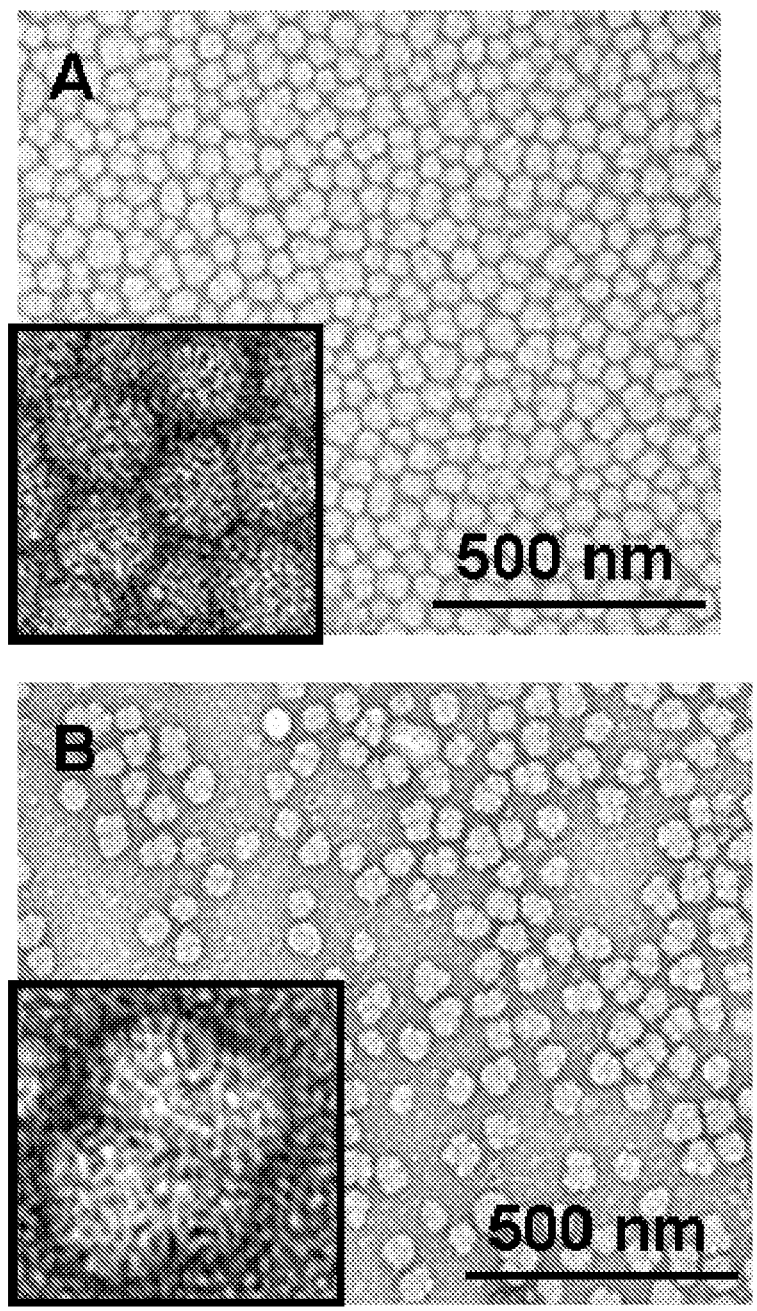

SDS-PAGE Analysis of Pfs48/45-Grl1 Particles: To visualize the differences between assembled and non-assembled Pfs48/45-Grl1 SDS page gel and Western blotting were performed. The samples were diluted in 2× SDS sample buffer supplied with reducing agent (0.7M βME). Total 2.5 ug of Pfs48/45 for each sample was loaded on a 10% SDS-page gel and subjected to electrophoresis. For staining the gel was incubated with coomassie blue stain for 1 hr, for Western blotting the proteins were transferred to a nitrocellulose membrane and probed with mouse anti-HA tag antibody (diluted 1:1000 in 5% milk PBS) for 1 hr at room temperature, followed by secondary antibody anti-mouse IgG labeled with Horseradish peroxidase (HRP)(diluted 1:3000 in 5% milk PBS) for 1 hr at room temperature. A shift in mobility of Pfs48/45-GRL1 fusion protein was observed after particle formation by both methods as shown in FIG. 6.

Example 2

Assembly of Immunogenic Particles from a Purified Source of *P. Falciparum* 48/45-Grl1 Fusion Protein Concentrated purified pfs48/45-Grl1 were obtained as in Example 1. For assembly experiments, the divalent cation concentration of 500 µl medium of concentrated purified protein was increased to 4 mM CaCl$_2$ and 5 mM MgCl$_2$ and the pH of the medium was adjusted to 5. 10 µl of sample was put on a formvar and carbon coated Ni grid and left for 2 min. Following incubation the sample was withdrawn from the grid with a filter wick. The grids were stained with 10 µl of 2% Uranyl acetate for 1 min, dried and examined with Technai 12 electron microscope. Aggregation was observed as in FIG. 5.

Example 3

Figure 9:
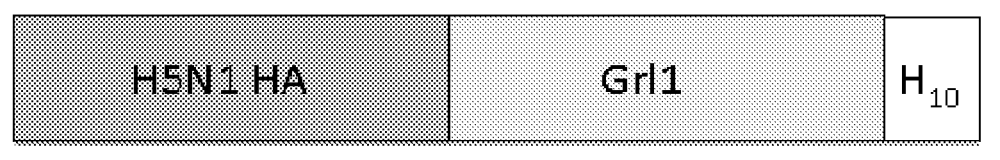

Assembly of Immunogenic Particles from a Purified Source of Influenza A/Vietnam/1194/2004-Grl1 Fusion Protein Gene Construct Design, Synthesis and Cloning: A synthetic gene was designed wherein the coding region of the hemagglutinin gene derived from A/Vietnam/1194/2004 (H5N1) lacking the C-terminal transmembrane domain was synthesized and cloned into a somatic expression vector, pTIEV5, containing the Pro-Grl1 gene lacking the pre-domain (signal peptide) and containing an engineered C-terminal 10× Histidine tag (FIG. 9). HA was cloned into the vector via BamHI and XhoI restriction sites engineered into the 5' and 3' ends of the synthetic gene, respectively, leading to an in-frame fusion with the Pro-Grl1 gene. Transcription of the transgene was under the control of a cadmium-inducible promoter from the metallothionein-5 (MTT5) gene of *T. thermophila*. The expression construct comprising MTT5 promoter, chimeric transgene, MTT1 terminator and a neomycin resistance cassette were transferred, en masse, as a NotI fragment into a high-copy rDNA vector, pD5H8 and introduced into conjugating *T. thermophila* strains by biolistic transformation. Generation of expression strains was as described in Example 1.

The complete amino acid sequence of the influenza A/Vietnam/1194/2004 H5N1 hemagglutinin protein is shown in SEQ ID NO: 12. The complete amino acid sequence of the influenza A/Vietnam/1194/2004 H5N1-Grl1 fusion protein is shown in SEQ ID NO: 13. The portion of H5N1 used in the Grl fusion is residues 1-519 of SEQ ID NO: 12, and residues 1-522 of SEQ ID NO: 13, with the insertion of a GS at positions 2-3 which is an artifact of a BamHI restriction site. The native HA signal peptide at position 1-16 of SEQ ID NO: 12 was employed at positions 1-18 of SE ID NO: 13, again with the inserted GS from the BamHI restriction site. Note that Leucine 532 and Tyrosine 554 of SEQ ID NO: 12 represent the N-terminal and C-terminal ends of a putative transmembrane domain, and therefore this portion of the HA molecule was purposefully excluded from the Grl/Ag fusion protein. However, the HA fusion point could have been chosen more C-terminal than Serine 519, and could have extended to Leucine 532 and presumably several residues into the transmembrane domain (e.g., residues 532, 533, 534, 535 or 536). Preliminary data indicates that including the entire transmembrane domain results in ER retention of the Grl fusion, preventing trafficking to the dense core granules. The LE at positions 23-24 of SEQ ID NO: 13 represents a cloning artifact from an XhoI restriction site. The Grl moiety is derived from the Grl4 protein of SEQ IDS NO: 4 and corresponds to residues 19-402 of that sequence (i.e., the Grl1 pro-protein) and residues 525-908. Finally, note the C-terminal His 10× purification tag at positions 909-918 of SEQ ID NO: 13.

Figure 10:
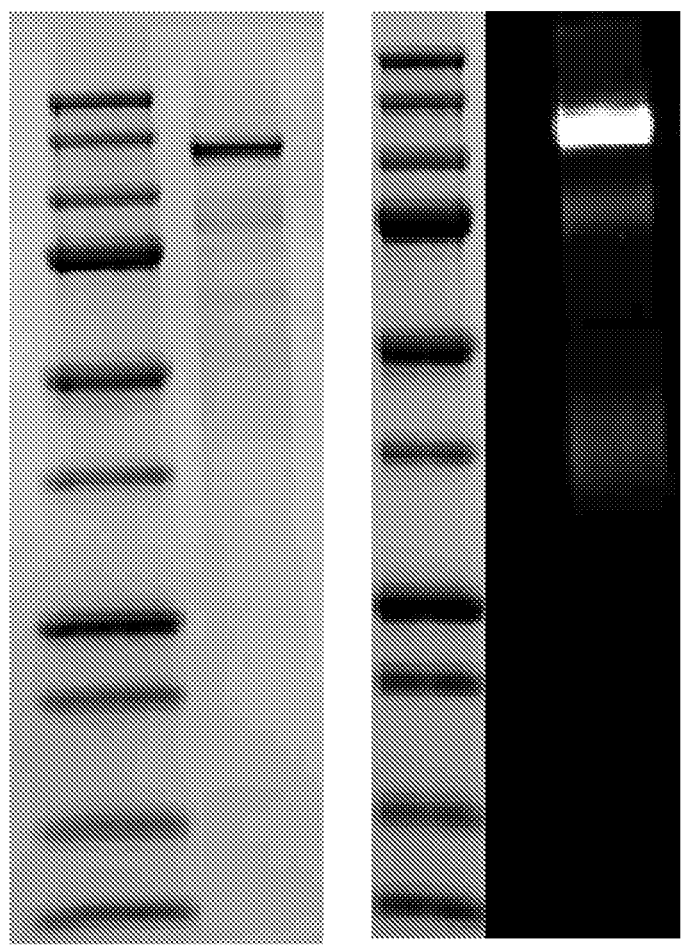

Purification of HA-Grl1: 1 ml of *Tetrahymena* stock culture transformed with HA-GRL1 fusion protein was grown in 10 ml NEFF medium in a 30° C. shaking incubator until the culture reached mid-log phase (5×10$^5$cell/ml). The next day the 10 ml culture was expanded to 500 ml and grown to stationary phase (1-1.5×10$^6$ cells/ml) at which point the cultures were diluted with fresh NEFF 1:1 and immediately induced with 1.5 ug/ml CdCl$_2$. Cells expressing recombinant HA-GRL1 were harvested by centrifugation and cell pellets were frozen in the presence of protease inhibitors. Cell pellet containing 7.5×10$^8$ cells was diluted in TGN buffer (40 mM Tris, 50 mM NaCl, 10% Glycerol) and brought up to final volume 350 ml. The lysate was incubated at 4° C. for 10-15 min after which it was centrifuged 50K×g for 30 min. Resulting pellets were kept and diluted in 500 ml final volume TGN Buffer containing 1% Tween-80 (T80). The mixture was stirred at 4° C. for 1 hr and microfluidized 3 times at 25KPSi and then filtered through a Corning 0.22 micron bottle top filter. 450 ml of post filter protein solution was loaded onto the Ni column pre-equilibrated with TGN buffer containing 1% T80. After loading the column was washed with 10 column volumes TGN 1% T80 and then 5 column volumes TGN 0.01% Tween80, 25 mM imidazole. The protein was eluted with 250 mM Imidazole. Fractions containing protein of interest were dialyzed immediately in TGN 0.01% Tween80, 5 mM EGTA. To determine if purified HA-Grl1 maintained correctly folded HA, the protein was resolved by SDS-PAGE and analyzed by Western Blot analysis using a conformation-dependant anti-H5N1 hemagglutinin antibody. FIG. 10 shows that the HA-Grl1 is recognized by the conformation-dependant antibody and therefore has a correctly folded hemagglutinin moiety.

Sucrose-density gradient analysis of assembled HA-Grl1 Particles: 1 ml of purified and concentrated HA-GRL1 protein was induced to form particles as described in Example 1 and layered on top of a step sucrose gradient composed of 1 ml each 3.5, 7, 14 and 35% sucrose from top to bottom respectively. The gradient was centrifuged at 225 k×g for 2.5 hr using a Beckman ultracentrifuge. After centrifugation 1 ml fractions were collected and analyzed by SDS page gel. As a control purified, soluble HA-Grl1 was used to layer on top of a sucrose gradient, the rest of the steps were carried out as described above. The results are shown in FIG. 11 and indicate that following particle formation fusion protein is exclusively recovered in the pellet fraction.

Electron Microscopy and Immunogold labeling analysis of HA-Grl1 particles: For immuno-gold labeling 10 μl of assembled HA-Grl1 particles (0.5 mg/ml final protein concentration) was put on formvar carbon coated grid and incubated for 30 min. The remaining sample was removed from the grid by using a filter paper wick. The grids were incubated face down in 1% fish gelatin PBS (blocking buffer) drops for 1 hr at room temperature followed by incubation in anti-hemagglutinin rabbit polyclonal antibody solution diluted 1:1 in blocking buffer over night at 4° C. The next day the grids were washed 3×10 min each in 2× PBS and blocked for 10 min in 1% fish gelatin PBS. After blocking the grids were incubated in secondary antibody solution (anti-rabbit IgG labeled with 10 nm gold particles-Sigma) for 3 hr at room temperature and washed 3× in PBS 5 min each and 1× in H$_2$O followed by staining in 1% Uranyl Acetate for 30 sec. Assembled particles were visualized using Technai 12 transmission electron microscope, HV=100.0 kV, direct magnification ~100.000×. The results are shown in FIG. 12.

Efficacy of a HA-Grl1 particle (HA-G-SOME) based vaccine in animals challenged with a virulent strain of H5N1 influenza: A HA-Grl particle based formulation was prepared as described in Example 3. The hemagglutinin moiety was derived from the influenza strain A/Vietnam/1194/2004. Six week-old BALB/c mice (n=10 per group) were immunized via intraperitoneal administration with 15 μg/200 μl dose HA-G-SOME containing 0.2% Alum and 15 μg/200 μl dose of a non-related G-SOME (negative control)+/−0.2% Alum per dose. Doses were administered twice on study days 0 and 21. Mice were challenged on Day 42 by intra-nasal administration of 75 μl of influenza A/Vietnam/1203/2004 (H5N1) consisting of approximately 5 plaque forming units (1×LD$_{90}$) of virus per mouse. Mortality of mice was monitored for 21 days post-challenge. FIG. 13 shows the percent survival for each group and indicates that mice immunized with the non-related control G-SOME with or without adjuvant did not protect animals from challenge whereas mice immunized with HA-G-SOME were protected from challenge (20 and 0% survival vs 90% survival, respectively). These results indicate that HA-G-SOME's functions effectively as an influenza vaccine.

Example 4

Production of Multi-Component Grl Based Immunogenic Particles

A synthetic gene encoding the bacterial flagellin was designed, synthesized and cloned into a somatic expression vector, pTIEV5, containing the Pro-Grl4 gene lacking the pre-domain (signal peptide) and containing an engineered C-terminal 10× Histidine tag (FIG. 14). Flagellin was cloned into the vector via BamHI and XhoI restriction sites engineered into the 5' and 3' ends of the synthetic gene, respectively, leading to an in-frame fusion with the Pro-Grl4 gene. Transcription of the transgene was under the control of a cadmium-inducible promoter from the metallothionein-5 (MTT5) gene of *T. thermophila*.

The complete amino acid sequence of the bacterial flagellin protein is shown in SEQ ID NO: 14. The complete amino acid sequence of the flagellin-Grl4 fusion protein is shown in SEQ ID NO: 15. Virtually the entire flagellin protein, residues 2-495 of SEQ ID NO: 14, is incorporated into the Grl/Ag fusion protein at residues 23-516 of SEQ ID NO: 15. Residues 1-22 of SEQ ID NO: 15 correspond to the signal peptide from the immobilization antigen variant B protein of *Ichthyophthirius multifiliis*, with the insertion of a GS at positions 2-3 which is an artifact of a BamHI restriction site. The LE at position 517-518 of SEQ ID NO: 15 represents another cloning artifact from an XhoI restriction site. The Grl moiety corresponds to residues 20-394 of SEQ ID NO: 4 (the Grl4 pro-protein), and to residues 519-893 of SEQ ID NO: 15. Finally, note the C-terminal His 10× purification tag at positions 894-903 of SEQ ID NO: 15.

The expression construct comprising MTT5 promoter, chimeric transgene, MTT 1 terminator and a neomycin resistance cassette were transferred, en masse, as a NotI fragment into a high-copy rDNA vector, pD5H8 and introduced into conjugating *T. thermophila* strains by biolistic transformation. Generation of expression strains was as described in Example 1. The flagellin-Grl4 gene was expressed and the fusion protein purified as described for HA-Grl1 in Example 3. Equal amounts of each fusion protein were mixed together and particle formation induced at 4° C. using TGN buffer supplied with 10 mM CaCl$_2$ and the pH adjusted to 5.5. 500 μl of assembled particle material was layered on top of a step sucrose gradient composed of 500 μl each 5, 10, 20,30,40, 50 and 65% sucrose from top to bottom respectively.

The gradient was centrifuged at 225 k×g for 2.5 hr using a Beckman ultracentrifuge. After centrifugation 500 μl fractions were collected and analyzed by SDS page gel. As a control a mixture containing purified soluble HA-Grl1 and Flagellin-Grl4 was used to layer on top of a sucrose gradient, the rest of the steps were carried out as described above. The results are shown in FIG. 15 and indicate that following induction of particle formation fusion protein is exclusively recovered in the highest sucrose density band suggesting that the fusion proteins have assembled into higher density particles.

Example 5

Grl1-scFv Fusion Protein

As described in Examples 3 and 7 of WO 2010/108182, a fusion construct comprised of the *Tetrahymena* Grl1 gene fused N-terminal and in-frame to the gene encoding a single chain antibody fragment (anti-anthrax PA toxin) is produced. Separating the Grl1 and scFv genes is DNA encoding, 5' to 3', a TEV protease site, a 6× His tag and a HA peptide epitope. Expression of the Grl/Ag fusion protein in *Tetrahymena* is examined by immunofluorescence and Western analysis in both whole cell lysates and harvested mucus as described herein. The analysis shows that the Grl/Ag fusion protein is targeted to cortical secretory granules (mucocysts) as evidenced by the punctate staining pattern at the cell periphery. Additionally, the Grl/Ag fusion protein is expressed and recovered in mucus following induced release of mucocyst contents.

The amino acid sequence of the Grl/Ag fusion protein is shown in SEQ ID NO: 16. The fusion protein is isolated and aggregation is induced to form granular protein particles as described herein.

Example 6

Grl4-pfs48/45 Fusion Protein

As described in Examples 3 and 8 of WO 2010/108182, a fusion construct comprised of a *Tetrahymena* Grl4-derived Grl moiety fused N-terminal and to the an Ag moiety derived from amino acids 159-426 the pfs48/45 protein is produced. Immediately downstream of the pfs48/45 sequence is a 6× His tag followed by the carboxy-terminal domain (amino acids 371-441) of the immobilization antigen variant B protein of *Ichthyophthirius multifiliis*. At the carboxy-terminus of the fusion construct is a HA epitope tag.

Expression of the Grl4-pfs48/45 fusion protein in *Tetrahymena* is examined by immunofluorescence and Western analysis in both whole cell lysates and harvested mucus as described herein. Results show that fusion protein is targeted to cortical secretory granules (mucocysts) as evidenced by the punctate staining pattern at the cell periphery. Additionally, results show that the fusion protein is expressed and is recovered in mucus following induced release of mucocyst contents. A majority of fusion protein in the mucus resolves at approximately 50 kDa indicating that the pre-pro-domain of Grl4 has been processed in vivo.

The amino acid sequence of the Grl/Ag fusion protein is shown in SEQ ID NO: 17. The fusion protein is isolated and aggregation is induced to form granular protein particles as described herein.

Example 7

Grl1-HA Fusion Protein

As described in FIG. 4 of WO 2010/108182, a fusion construct comprised of a *Tetrahymena* Grl1-derived Grl moiety fused N-terminal and to an Ag moiety derived from the H5N1 HA antigen is produced.

Expression of the Grl/Ag fusion in *Tetrahymena* is examined by immunofluorescence and Western analysis in both whole cell lysates and harvested mucus as described herein. Results show that the Grl/Ag fusion is targeted to cortical secretory granules (mucocysts) as evidenced by the punctate staining pattern at the cell periphery. Additionally, results show that the Grl/Ag fusion is expressed and is recovered in mucus following induced release of mucocyst contents.

The amino acid sequence of the Grl/Ag fusion protein is shown in SEQ ID NO: 18. The fusion protein is isolated and aggregation is induced to form granular protein particles as described herein.

```
                            SEQUENCE LISTING

SEQ ID NO: 1 (Tetrahymena Granule Lattice Protein 1 Precursor)
MNKKLLVVLF GFLALAAATN QSEEEGSYTI DQAANLLNDL LADSQQNLSD LQAAWANKEP      60
LLQGVIAGLE SDLANKQAEC ADLQGTLDAD QASLDEAEAY VAWLQDRIAA NHKQIDDLLN     120
RRCQQNGNYI EGLKNDKLAL ALLQFLEAQI QNKESFSFLQ KKNFMKKLTR FLSIYKTGNY     180
QQLALLEKEY VNADDYSVNP DYSTGDRTAD EIGSGHIDND KGDIDVADFQ EGERKGWYQV     240
KQELLDLLHN LEQTIEAKIQ QAQEDEVNSN SAAADFKSKL EHEIQVYERE LAKWQQTVAA     300
LTATVAQDHE NVNNCHSQEA AIQANLDAAN QDYANEKATF EHKQANLQEE IEIFIEVIAY     360
YDDNVQNAGE DLKERVEDYS DGNFDDAATY ENRQVPNIDF IN                        402

SEQ ID NO: 2 (Tetrahymena Granule Lattice Protein 2 Precursor)
MRLTVIVTLS LLFGCIMAAE AEAELEATYE IDNALEALTE LRDDTALSLY NLQKGWAVVK      60
DGLQDSENQL QNSINQKDAE CANLDQARNQ TQSDLDEINA YIPWLEQKIA NITDSLNSLL     120
QRRCDLNKAF LDHIQREKIA LSLLEFIKSA IQNKDSFDFV QMRKLNKNFQ QFLIAYSAHD     180
FSSILLLQKD IVDSKDYEVD VDFSTKDRTE EEIGTGHIDN NKGDLDLEDF TEGKRKNWQL     240
YKQELLDILN ELQAKIQANI KSSIDDEIAA SVTLANYKNN ALKEIQAYEK ELAKAKKQQV     300
QLQAQLDDEQ NALTQCRSQD DSLKNQLQSL QNEIQQRQAE FDKKKDDLQG QVDLFNEIIT     360
EYQDGIFSQG DDFKGRTDDY LDNQTFDDDA TYTGREVPKI DFMNNQDANG SASSGGF        417

SEQ ID NO: 3 (Tetrahymena Granule Lattice Protein 3 Precursor)
MKNLAIVLAA LCIFAQATSV FETPAFLEIK SNPFGHTVAS LVQLNLGAGQ SAGRLDAIAE      60
ALNTIEAQLE NTRDHNDAEI QRQRGWCSDQ EATIQANIDQ AESDLSNYQN EQTQRNQAVA     120
DLTQNLNNEQ QSLAENQNNL ANAQQELDDE NSSYAESSKD YADAIAACEQ ALKLLATLQT     180
NPSGFIQSKA RFGNVVTLLQ KHLANKSSNF VQPILNVLTE MASSTNEVDQ SSLAKVVSLI     240
NDLLEELRNQ SAANDQRHQQ VVDSLTSNIA NLEQLIDNSN NLISQYQGQI QENEDRLAQL     300
AGLIQQTQAI LDQANQNLSQ VQDQCAGYDQ EYASFKNEVD QQLATLQALK EYFKSKVVPA     360
VENINDSAYA DELTVDV                                                    377
```

SEQUENCE LISTING

```
SEQ ID NO: 4 (Tetrahymena Granule Lattice Protein 4 Precursor)
MRYAALFLLA LISFNAVYAV SLRKSSDAMK TSFALERLRF IGKKSPIAKQ IISAVELHLT      60
TGGLVDDVID LVKQAQEDVA NRNVALQAEY TAKRGALEDQ INTTTQQLNE ENDRLAVVND     120
AIDALNGQID SLNTQIANLV QQLQNLQARE DAINQAREVD VKTYEVRKQR DENSLAVLEQ     180
IIQRLLALQQ RGNAFLQVSK KEIERILKRI PKSNPIQALV QLSTKFDEQR LAEVISKLQT     240
IQAAIQASYI EDANGEVADK QRYDALIQEI ATIRAQTQQQ LADAQQALSD AEASLAQFVQ     300
EQGNLQQQIA VNEGILADAQ AALAHTIATY EARIQEGQEA LAAINLALDV LQQNQSDLQG     360
VEDFSNAYNA YQAGNSTDAG DDAGDDSGVE GEAF                                394

SEQ ID NO: 5 (Tetrahymena Granule Lattice Protein 5 Precursor)
MRVIAALLVI ALVCQSAMAV TSKSQAKLMM EKINSKLEKS HLGRALKGMV TIATKLGYDY      60
QDLYDAFAAL KNQLLNNLDN ENSLFETQTA SHDSAVAQFN ADISNYNGQI NDAQAQLNDL     120
NDSLNTYQQN LQDAQQALQD NTDALNAAEE ALANAEALYQ VATAEYSNAD QVIGLAVEKL     180
QEAQSHYDNA DLGSFSFVQI KNTFVSFAQK VTEATKGMNA KHQLFVKPVV QAMMQVKNNT     240
SQSSIQTAIK ALQDLQAYFQ KTFSDLTNEY VSFTQNVQST IDGLNQIIDI LQNQVIPGYE     300
AQISSLQAQI QQVEDALALA QQNLQDAQNA LDAENAQWEN VVARHQALVD RINSEYDLVT     360
QADRIVRNAQ AQVNGSD                                                   377

SEQ ID NO: 6 (Tetrahymena Granule Lattice Protein 6 Precursor)
MLLEYLNLNI LRLTPHIKRN GIVNSNSNKL QRCSLLISEN ILSQNKKFVS IIQFFLRDIY      60
LEQYLKKYQN QQLKNQIYIL LQYVFNILNQ IEKSRFGRNI LDTIQLQLSV NDQIGRLVSD     120
LQNIATDIQN DQAQDQKQTE RIQQDCSNDL SRLEDEIQDA NLKVIESTSD ITENTPILEQ     180
KKILLKQKSE SLTANQQILS DLDQNYEKKS AEYEAEREEH SKAESVIREA KEILQGTFGS     240
TKSFISIKKP SVQSFVQVSN HFSHHSKTNY KRKSWNSFFR ILSQLSQSAP IQADPGALQK     300
LFEVIDELLE KIADSLEIEA KAFEQFEQDY ENKKDDILDR IGVLQKVIGE LDGEISSLEA     360
QLQEDARVKQ VQQERSEEKQ TELNSRQAFC TDQQSQFESR TQERRCLNKN RVNTLKLFQK     420
FKQQINIDRL TNSQQTTYFK NKKERKIMEQ ISLQIQNSLE EAISILKIIS NSQEKGLILT     480
DILINDIYFI RNLILSGKEE QLNNYFQDLN IIVDKAKLIK NNLTFSCVSK YGNFIQIFQQ     540
EPIKVIFQKI NSILQNIKKQ FPKQIDSNDV YSLDSKKIEQ IFKLHSKLQT FRQYQNMNQF     600
QSYHQLTVLF KMCNDQQGER ESLLKSIASF ILPTSCLTSQ NKQIAIEQYI PLKDLKLKIC     640
NGDFEGVIQS SQSLLLEKNK LQIIGERKVS EMNYQHSVNQ IQPYCIDCIL LTPISRSLNC     680
LLVEGQEINL NYGEQIKEYS ICHDSMKLKL IINMEKETNQ KNLYALIDEN QMKQKDAQDN     720
MQNLETETNT NNTSNQQIDY FEETEDYDNK MLNLHNQYNL QDREAVSFFS KFAHTSKIER     780
LKTDKMDWIE KQRNHIHPSI QKLIQIFNQI KSNQSIHPSI HQSFHLFDYF                830

SEQ ID NO: 7 (Tetrahymena Granule Lattice Protein 7 Precursor)
MRKVFVALAL VAIIVSATML PEVRQRAKVS LQKLHKSRIG KNIVTAIQLE LSSKNRDNII      60
VNILALLNDL LNDQSTQLTK AQSDLADKQD YCGSSIESYQ NQIASKQADI ANAQASLPAL     120
HAELETDQAN LADQEAKLDR AQQNLAEAND LNDAAVAAFN TSIANHNAMI DALKQARALI     180
VQLQSSSFLQ KNNAVLIQLS NHKALALKKL EGHAKKSLFS LLMQMAQDVG IQADQTLVGN     240
VLTVIDDLLQ HEQDGIDAET QAENQRVEEY NAAVIDFNNQ ISDAQGQIAS LNQDIQTLTN     300
NINDTENNIA TWSQQVSDLQ GVLDELQNQC NADIAHFQDL IQELNGIIDI IQQVIAIFEG     360
QSIQDVKPLF DDISVDDGLG SAESA                                          385

SEQ ID NO: 8 (Tetrahymena Granule Lattice Protein 8 Precursor)
MNKALVFLAI IALGFAASTQ QVSALDPSEN AADALIDQLN QMEGAIRKEQ QAHDELAQEQ      60
DAECAQEFQF RQNEINDAQN AFDAANAAAG RCQNALTASQ ADLEKANNYV SSIQQILAGL     120
ASQRLAEHNA YEDLVNNQLQ PAIDAVQGAY PILSDFASQT VSFVQFSNHI NKMFLQMVKA     180
NKVNSFTAIL TVLLSQPDFQ HGVGRDAIDQ LQALFEQLEQ DLQAALDHAT EVENNAVQVY     240
NDTVNEYNAV LATLDATISS LNDYISSLEN CVQNENSIAS QANAKKVRNS DALAYAVDMC     300
QAFDTEYQNA TAARNDELAL LQKLENFVHE QADIFGDYGT DNVDAFDDFK QSYDAQRDTQ     360
RGNFMQMKIK QFKMNSNFKK VAKCESCSRK SFVQKKLGF                           399

SEQ ID NO: 9 (Tetrahymena Granule Lattice Protein 9 Precursor)
MRVIAALLVI ALVCQSAMAV TSKSQVKLMM EKINSKMEKS PLGRALKGMV TIATKLGYDY      60
QDLYDAFAAL KNQLLNSLDN ENSLFEEQTA CHENFIAQFN ALISNYTSQI NDTEAQLNYL     120
NDSLNTYEQN LKDAQQALQD NTDALNAAEE ALAQAEVLYQ YATAEYSNAD QVIGVAIEKL     180
QEAQSHYDNA DLGSFSFVQI KNTFVSFAQK ITEATKGMNA KHQLFVKPVV QAMMQVKNNT     240
SQTSIQTAIK ALQDLQAYFQ KTFTDLTNEY VIFTQNVQST IDGLNQLIDI LQNQTIPGYE     300
SQISQIQAQI QQFEDALSLA QQNLKQAQDY ISAEYEIFAI VQARHQALVD RINSEYDLVT     360
QADRIVRNAQ AQVNYSN                                                   377

SEQ ID NO: 10 (P. falciparum Pfs 48/45 protein)
MMLYISAKKA QVAFILYIVL VLRIISGNND FCKPSSLNSE ISGFIGYKCN FSNEGVHNLK      60
PDMRERRSIF CTIHSYFIYD KIRLIIPKKS SSPEFKILPE KCFQKVYTDY ENRVETDISE     120
LGLIEYEIEE NDTNPNYNER TITISPFSPK DIEFFCFICH TEKVISSIEG RSAMVHVRVL     180
KYPHNILFTN LTNDLFTYLP KTYNESNFVS NVLEVELNDG ELFVLACELI NKKCFQEGKE     240
KALYKSNKII YHKNLTIFKA PFYVTSKDVN TECTCKFKNN NYKIVLKPKY EKKVIHGCNF     300
SSNVSSKHTF TDSLDISLVD DSAHISCNVH LSEPKYNHLV GLNCPGDIIP DCFFQVYQPE     360
SEELEPSNIV YLDSQINIGD IEYYEDAEGD DKIKLFGIVG SIPKTTSFTC ICKKDKKSAY     420
MTVTIDSAYY GFLAKTFIFL IVAILLYI                                       448

SEQ ID NO: 11 (Pfs 48/45-Grl1 fusion protein)
MGSKFNILII LIISLFINEL RADNTEKVIS SIEGRSAMVH VRVLKYPHNI LFTNLTNDLF      60
TYLPKTYNES NFVSNVLEVE LNDGELFVLA CELINKKCFQ EGKEKALYKS NKIIYHKNLT     120
IFKAPFYVTS KDVNTECTCK FKNNNYKIVL KPKYEKKVIH GCNFSSNVSS KHTFTDSLDI     180
SLVDDSAHIS CNVHLSEPKY NHLVGLNCPG DIIPDCFFQV YQPESEELEP SNIVYLDSQI     240
```

```
                         SEQUENCE LISTING

NIGDIEYYED AEGDDDKIKLF GIVGSIPKTT SFTCICKKDK KSAYMTVTID HHHHHHCPAG    300
TVVDDGTSTN FVALASECTK CQANFYASKT SGFAAGTDTC TECSKKLTSG ATAKVYAEAT    360
QKAQCASTNQ SEEEGSYTID QAANLLNDLL ADSQQNLSDL QAAWANKEPL LQGVIAGLES    420
DLANKQAECA DLQGTLDADQ ASLDEAEAYV AWLQDRIAAN HKQIDDLLNR RCQQNGNYIE    480
GLKNDKLALA LLQFLEAQIQ NKESFSFLQK KNFMKKLTRF LSIYKTGNYQ QLALLEKEYV    540
NADDYSVNPD YSTGDRTADE IGSGHIDNDK GDIDVADFQE GERKGWYQVK QELLDLLHNL    600
EQTIEAKIQQ AQEDEVNSNS AAADPKSKLE HEIQVYEREL AKWQQTVAAL TATVAQDHEN    660
VNNCHSQEAA IQANLDAANQ DYANEKATFE HKQANLQEEI EIFIEVIAYY DDNVQNAGED    720
LKERVEDYSD GNFDDAATYE NRQVPNIDFI NHHHHHHHHH H                       761

SEQ ID NO: 12 (Influenza A/Vietnam/1194/2004 H5N1 hemagglutinin pro-
tein)
MEKIVLLFAI VSLVKSDQIC IGYHANNSTE QVDTIMEKNV TVTAQDILEK THNGKLCDLD     60
GVKPLILRDC SVAGWLLGNP MCDEFINVPE WSYIVEKANP VNDLCYPGDF NDYEELKHLL    120
SRINHFEKIQ IIPKSSWSSH EASLGVSSAC PYQGKSSFFR NVVWLIKKNS TYPTIKRSYN    180
NTNQEDLLVL WGIHHPNDAA EQTKLYQNPT TYISVGTSTL NQRLVPRIAT RSKVNGQSGR    240
MEFFWTILKP NDAINFESNG NFIAPEYAYK IVKKGDSTIM KSELEYGNCN TKCQTPMGAI    300
NSSMPFHNIH PLTIGECPKY VKSNRLVLAT GLRNSPQRER RRKKRGLFGA IAGFIEGGWQ    360
GMVDGWYGYH HSNEQGSGYA ADKESTQKAI DGVTNKVNSI IDKMNTQFEA VGREFNNLER    420
RIENLNKKME DGFLDVWTYN AELLVLMENE RTLDFHDSNV KNLYDKVRLQ LRDNAKELGN    480
GCFEFYHKCD NECMESVRNG TYDYPQYSEE ARLKREEISG VKLESIGIYQ ILSIYSTVAS    540
SLALAIMVAG LSLWMCSNGS LQCRICI                                       567

SEQ ID NO: 13 (H5N1-Gr11 fusion protein)
MGSEKIVLLF AIVSLVKSDQ ICIGYHANNS TEQVDTIMEK NVTVTHAQDI LEKTHNGKLC     60
DLDGVKPLIL RDCSVAGWLL GNPMCDEFIN VPEWSYIVEK ANPVNDLCYP GDFNDYEELK    120
HLLSRINHFE KIQIIPKSSW SSHEASLGVS SACPYQGKSS FFRNVVWLIK KNSTYPTIKR    180
SYNNTNQEDL LVLWGIHHPN DAAEQTKLYQ NPTTYISVGT STLNQRLVPR IATRSKVNGQ    240
SGRMEFFWTI LKPNDAINFE SNGNPIAPEY AYKIVKKGDS TIMKSELEYG NCNTKCQTPM    300
GAINSSMPFH NIHPLTIGEC PKYVKSNRLV LATGLRNSPQ RERRRKKRGL FGAIAGFIEG    360
GWQGMVDGWY GYHHSNEQGS GYAADKESTQ KAIDGVTNKV NSIIDKMNTQ FEAVGREFNN    420
LERRIENLNK KMEDGFLDVW TYNAELLVLM ENERTLDFHD SNVKNLYDKV RLQLRDNAKE    480
LGNGCFEFYH KCDNECMESV RNGTYDYPQY SEEARLKREE ISLETNQSEE EGSYTIDQAA    540
NLLNDLLADS QQNLSDLQAA WANKEPLLQG VIAGLESDLA NKQAECADLQ GTLDADQASL    600
DEAEAYVAWL QDRIAANHKQ IDDLLNRRCQ QNGNYIEGLK NDKLALALLQ FLEAQIQNKE    660
SFSFLQKNF MKKLTRFLSI YKTGNYQQLA LLEKEYVNAD DYSVNPDYST GDRTADEIGS    720
GHIDNDKGDI DVADFQEGER KGWYQVKQEL LDLLHNLEQT IEAKIQQAQE DEVNSNSAAA    780
DFKSKLEHEI QVYERELAKW QQTVAALTAT VAQDHENVNN CHSQEAAIQA NLDAANQDYA    840
NEKATFEHKQ ANLQEEIEIF IEVIAYYDDN VQNAGEDLKE RVEDYSDGNF DDAATYENRQ    900
VPNIDFINHH HHHHHHH                                                  918

SEQ ID NO: 14 (Bacterial flagellin protein)
MAQVINTNSL SLLTQNNLNK SQSALGTAIE RLSSGLRINS AKDDAAGQAI ANRFTANIKG     60
LTQASRNAND GISIAQTTEG ALNEINNNLQ RVRELAVQSA NSTNSQSDLD SIQAEITQRL    120
NEIDRVSGQT QFNGVKVLAQ DNTLTIQVGA NDGETIDIDL KQINSQTLGL DTLNVQQKYK    180
VSDTAATVTG YADTTIALDN STFKASATGL GGTDQKIDGD LKFDDTTGKY YAKVTVTGGT    240
GKDGYYEVSV DKTNGEVTLA GGATSPLTGG LPATATEDVK NVQVANADLT EAKAALTAAG    300
VTGTASVVKM SYTDNNGKTI DGGLAVKVGD DYYSATQNKD GSISINTTKY TADDGTSKTA    360
LNKLGGADGK TEVVSIGGKT YAASKAEGHN FKAQPDLAEA AATTTENPLQ KIDAALAQVD    420
TLRSDLGAVQ NRFNSAITNL GNTVNNLTSA RSRIEDSDYA TEVSNMSRAQ ILQQAGTSVL    480
AQANQVPQNV LSLLR                                                    495

SEQ ID NO: 15 (Flagellin-Gr14 fusion protein)
MGSKFNILII LIISLFINEL RAAQVINTNS LSLLTQNNLN KSQSALGTAI ERLSSGLRIN     60
SAKDDAAGQA IANRFTANIK GLTQASRNAN DGISIAQTTE GALNEINNNL QRVRELAVQS    120
ANSTNSQSDL DSIQAEITQR LNEIDRVSGQ TQFNGVKVLA QDNTLTIQVG ANDGETIDID    180
LKQINSQTLG LDTLNVQQKY KVSDTAATVT GYADTTIALD NSTFKASATG LGGTDQKIDG    240
DLKFDDTTGK YYAKVTVTGG TGKDGYYEVS VDKTNGEVTL AGGATSPLTG GLPATATEDV    300
KNVQVANADL TEAKAALTAA GVTGTASVVK MSYTDNNGKT IDGGLAVKVG DDYYSATQNK    360
DGSISINTTK YTADDGTSKT ALNKLGGADG KTEVVSIGGK TYAASKAEGH NFKAQPDLAE    420
AAATTTENPL QKIDAALAQV DTLRSDLGAV QNRFNSAITN LGNTVNNLTS ARSRIEDSDY    480
ATEVSNMSRA QILQQAGTSV LAQANQVPQN VLSLLRLEVS LRKSSDAMKT SFALERLRFI    540
GKKSPIAKQI ISAVELHLTT GGLVDDVIDL VKQAQEDVAN RNVALQAEYT AKRGALEDQI    600
NTTTQQLNEE NDRLAVVNDA IDALNGQIDS LNTQIANLVQ QLNLQARED AINQAREVDV    660
KTYEVRKQRD ENSLAVEQI IQRLLALQQR GNAFLQVKIP KSNPIQALVQ                720
LSTKFDEQRL AEVISKLQTI QAAIQASYIE DANGEVADKQ RYDALIQEIA TIRAQTQQQL    780
ADAQQALSDA EASLAQFVQE QGNLQQQIAV NEGILADAQA ALAHTIATYE ARIQEGQEAL    840
AAINLALDVL QQNQSDLQGV EDFSNAYNAY QAGNSTDAGD DAGDDSGVEG EAFHHHHHHH    900
HHH                                                                 903

SEQ ID NO: 16 (Gr11-scFv fusion protein)
MGSNKLLVVL FGFLALAAAT NQSEEEGSYT IDQAANLLND LLADSQQNLS DLQAAWANKE     60
PLLQGVIAGL ESDLANKQAE CADLQGTLDA DQASLDEAEA YVAWLQDRIA ANHKQIDDLL    120
NRRCQQNGNY IEGLKNDKLA LALLQFLEAQ IQNKESFSFL QKKNFMKKLT RFLSIYKTGN    180
YQQLALLEKE YVNADDYSVN PDYSTGDRTA DEIGSGHIDN DKGDIDVADF QEGERKGWYQ    240
VKQELLDLLH NLEQTIEAKI QQAQEDEVNS NSAAADFKSK LEHEIQVYER ELAKWQQTVA    300
ALTATVAQDH ENVNNCHSQE AAIQANLDAA NQDYANEKAT FEHKQANLQE EIEIFIEVIA    360
YYDDNVQNAG EDLKERVEDY SDGNFDDAAT YENRQVPNID FINENLYFQG HHHHHCYPY    420
```

| SEQUENCE LISTING | | | | | |
|---|---|---|---|---|---|
| DVPDYASLDI | QMTQSPSSLS | ASVGDRVTIT | CRASQDIRNY | LNWYQQKPGK | APKLLIYYTS 480 |
| RLLPGVPSRF | SGSGSGTDYT | LTISSQEQED | IATYYCQQGN | TLPWTFGQGT | KVEIKRTGGG 540 |
| GSGGGGSGGG | GSGGGGSEVQ | LVESGGGLVQ | PGGSLRLSCA | DSGYAFSSSW | MNWVRQAPGK 600 |
| GLEWVGRIYP | GDGDTNYNGK | FKGRATISAD | KSSSTAYLQM | NSLRAEDTAV | YYCARSGLLR 660 |
| YAMDYWGQGT | LVTVSS | | | | 676 |

SEQ ID NO: 17 (Gr14-pfs 48/45 fusion protein)
| | | | | | |
|---|---|---|---|---|---|
| MGSRYAALFL | LALISFNAVY | AVSLRKSSDA | MKTSFALERL | RFIGKKSPIA | KQIISAVELH 60 |
| LTTGGLVDDV | IDLVKQAQED | VANRNVALQA | EYTAKRGALE | DQINTTTQQL | NEENDRLAVV 120 |
| NDAIDALNGQ | IDSLNTQIAN | LVQQLQNLQA | REDAINQARE | VDVKTYEVRK | QRDENSLAVL 180 |
| EQIIQRLLAL | QQRGNAFLQV | SKKEIERILK | RIPKSNPIQA | LVQLSTKFDE | QRLAEVISKL 240 |
| QTIQAAIQAS | YIEDANGEVA | DKQRYDALIQ | EIATIRAQTQ | QQLADAQQAL | SDAEASLAQF 300 |
| VQEQGNLQQQ | IAVNEGILAD | AQAALAHTIA | TYEARIQEGQ | EALAAINLAL | DVLQQNQSDL 360 |
| QGVEDFSNAY | NAYQAGNSTD | AGDDAGDDSG | VEGEAFDNTE | KVISSIEGRS | AMVHVRVLKY 420 |
| PHNILFTNLT | NDLFTYLPKT | YNESNFVSNV | LEVELNDGEL | FVLACELINK | KCFQEGKEKA 480 |
| LYKSNKIIYH | KNLTIFKAPF | YVTSKDVNTE | CTCKFKNNNY | KIVLKPKYEK | KVIHGCNFSS 540 |
| NVSSKHTFTD | SLDISLVDDS | AHISCNVHLS | EPKYNHLVGL | NCPGDIIPDC | FFQVYQPESE 600 |
| ELEPSNIVYL | DSQINIGDIE | YYEDAEGDDK | IKLFGIVGSI | PKTTSFTCIC | KKDKKSAYMT 660 |
| VTIDHHHHHH | CPAGTVVDDG | TSTNFVALAS | ECTKCQANFY | ASKTSGFAAG | TDTCTECSKK 720 |
| LTSGATAKVY | AEATQKAQCA | SYPYDVPDYA | | | 750 |

SEQ ID NO: 18 (Gr11-HA fusion protein)
| | | | | | |
|---|---|---|---|---|---|
| MGSKLLVVLF | GFLALAAATN | QSEEEGSYTI | DQAANLLNDL | LADSQQNLSD | LQAAWANKEP 60 |
| LLQGVIAGLE | SDLANKQAEC | ADLQGTLDAD | QASLDEAEAY | VAWLQDRIAA | NHKQIDDLLN 120 |
| RRCQQNGNYI | EGLKNDKLAL | ALLQFLEAQI | QNKESFSFLQ | KKNFMKKLTR | FLSIYKTGNY 180 |
| QQLALLEKEY | VNADDYSVNP | DYSTGDRTAD | EIGSGHIDND | KGDIDVADFQ | EGERKGWYQV 240 |
| KQELLDLLHN | LEQTIEAKIQ | QAQEDEVNSN | SAAADFKSKL | EHEIQVYERE | LAKWQQTVAA 300 |
| LTATVAQDHE | NVNNCHSQEA | AIQANLDAAN | QDYANEKATF | EHKQANLQEE | IEIFIEVIAY 360 |
| YDDNVQNAGE | DLKERVEDYS | DGNFDDAATY | ENRQVPNIDF | INDQICIGYH | ANNSTEQVDT 420 |
| IMEKNVTVTH | AQDILEKTHN | GKLCDLDGVK | PLILRDCSVA | GWLLGNPMCD | EFINVPEWSY 480 |
| IVEKANPVND | LCYPGDFNDY | EELKHLLSRI | NHFEKIQIIP | KSSWSSHEAS | LGVSSACPYQ 540 |
| GKSSFFRNVV | WLIKKNSTYP | TIKRSYNNTN | QEDLLVLWGI | HHPNDAAEQT | KLYQNPTTYI 600 |
| SVGTSTLNQR | LVPRIATRSK | VNGQSGRMEF | FWTILKPNDA | INFESNGNFI | APEYAYKIVK 660 |
| KGDSTIMKSE | LEYGNCNTKC | QTPMGAINSS | MPFHNIHPLT | IGECPKYVKS | NRLVLATGLR 720 |
| NSPQRERRRK | KRGLFGAIAG | FIEGGWQGMV | DGWYGYHHSN | EQGSGYAADK | ESTQKAIDGV 780 |
| TNKVNSIIDK | MNTQFEAVGR | EFNNLERRIE | NLNKKMEDGF | LDVWTYNAEL | LVLMENERTL 840 |
| DFHDSNVKNL | YDKVRLQLRD | NAKELGNGCF | EFYHKCDNEC | MESVRNGTYD | YPQYSEEARL 900 |
| KREEIS | | | | | 906 |

---

What is claimed is:

1. An immunogenic composition comprising self-assembled granular particles of a fusion polypeptide comprising
   a) a Granule lattice protein (Grl) comprising a Grl moiety:
      i) wherein the Grl moiety is selected from the group consisting of Grl 1-9; or
      ii) wherein the Grl moiety has at least about 95% amino acid sequence identity to SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, or SEQ ID NO: 9; and
   b) an antigen (Ag) moiety, wherein the particles self assembled into granules in a medium comprising a divalent cation, when said divalent cation was present in the medium at a concentration of at least about 0.01 mM.

2. The immunogenic composition of claim 1, wherein the composition comprises two or more different Grl/Ag fusion polypeptides.

3. The immunogenic composition of claim 2, wherein at least one of the two or more different Grl/Ag fusion polypeptides comprises a different Grl moiety from another Grl/Ag fusion polypeptide.

4. The immunogenic composition of claim 2, wherein at least one of the two or more different Grl/Ag fusion polypeptides comprises a different Ag moiety from another Grl/Ag fusion polypeptide.

5. The immunogenic composition of claim 1, wherein the particles have a mean diameter of less than about 1 μm.

6. The immunogenic composition of claim 1, wherein the particles have a mean diameter from about 20 nm to about 200 nm.

7. The immunogenic composition of claim 1, wherein the particles consist essentially of the Grl/Ag fusion polypeptide.

8. The immunogenic composition of claim 1, wherein the particles consist of at least about 10% to about 90% Grl/Ag fusion polypeptide by weight of the particle.

9. The immunogenic composition of claim 1, wherein the composition further comprises one or more ciliate secretory granule proteins.

10. The immunogenic composition of claim 1, wherein the particles self assembled in a medium comprising a divalent cation when said divalent cation is present in the medium at a concentration of at least about 0.5 mM.

11. The immunogenic composition of claim 1, wherein the particles self assembled in a medium comprising a divalent cation when said divalent cation is present in the medium at a concentration of at least about 2.0 mM.

12. The immunogenic composition of claim 10, wherein the divalent cation is $Ca^{2+}$.

13. The immunogenic composition of claim 10, wherein the divalent cation is $Mg^{2+}$.

14. The immunogenic composition of claim 10, wherein the divalent cation is $Mn^{2+}$, $CO^{2+}$, $Cd^{2+}$, $Zn^{2+}$, $Cu^{2+}$, $Cd^{2+}$, $Sr^{2+}$, $Ba^{2+}$, $Ni^{2+}$, $Fe^{2+}$, $Hg^{2+}$, $Pb^{2+}$, or $Cr^{2+}$.

15. The immunogenic composition of claim 1, wherein the particles self assembled in a medium having a pH of about 5.0 or lower.

16. The immunogenic composition of claim 1, wherein the Ag moiety is selected from the group consisting of a pathogen polypeptide, a bacterial polypeptide, a viral polypeptide, a protozoan polypeptide and a worm polypeptide.

17. The immunogenic composition of claim 1, wherein the Ag moiety is selected from the group consisting of a fungal polypeptide, a plant polypeptide, a yeast polypeptide, an insect polypeptide, and a vertebrate polypeptide.

18. The immunogenic composition of claim 1, wherein the Ag moiety is selected from the group consisting of a cytokine, an inflammatory molecule, a growth factor, a growth factor receptor, and an oncogene.

19. A method for producing an immunological response in an animal, the method comprising administering the immunogenic composition of claim 1 to the animal.

* * * * *

SEQUENCE LISTING

<160> NUMBER OF SEQ ID NOS: 20

<210> SEQ ID NO 1
<211> LENGTH: 402
<212> TYPE: PRT
<213> ORGANISM: Tetrahymena thermophila

<400> SEQUENCE: 1

```
Met Asn Lys Lys Leu Leu Val Val Leu Phe Gly Phe Leu Ala Leu Ala
1               5                   10                  15

Ala Ala Thr Asn Gln Ser Glu Glu Glu Gly Ser Tyr Thr Ile Asp Gln
            20                  25                  30

Ala Ala Asn Leu Leu Asn Asp Leu Leu Ala Asp Ser Gln Gln Asn Leu
        35                  40                  45

Ser Asp Leu Gln Ala Ala Trp Ala Asn Lys Glu Pro Leu Leu Gln Gly
    50                  55                  60

Val Ile Ala Gly Leu Glu Ser Asp Leu Ala Asn Lys Gln Ala Glu Cys
65                  70                  75                  80

Ala Asp Leu Gln Gly Thr Leu Asp Ala Asp Gln Ala Ser Leu Asp Glu
                85                  90                  95

Ala Glu Ala Tyr Val Ala Trp Leu Gln Asp Arg Ile Ala Ala Asn His
            100                 105                 110

Lys Gln Ile Asp Asp Leu Leu Asn Arg Arg Cys Gln Gln Asn Gly Asn
        115                 120                 125
```

```
Tyr Ile Glu Gly Leu Lys Asn Asp Lys Leu Ala Leu Ala Leu Leu Gln
            130                 135                 140

Phe Leu Glu Ala Gln Ile Gln Asn Lys Glu Ser Phe Ser Phe Leu Gln
145                 150                 155                 160

Lys Lys Asn Phe Met Lys Lys Leu Thr Arg Phe Leu Ser Ile Tyr Lys
                165                 170                 175

Thr Gly Asn Tyr Gln Gln Leu Ala Leu Leu Glu Lys Glu Tyr Val Asn
            180                 185                 190

Ala Asp Asp Tyr Ser Val Asn Pro Asp Tyr Ser Thr Gly Asp Arg Thr
        195                 200                 205

Ala Asp Glu Ile Gly Ser Gly His Ile Asp Asn Asp Lys Gly Asp Ile
    210                 215                 220

Asp Val Ala Asp Phe Gln Glu Gly Glu Arg Lys Gly Trp Tyr Gln Val
225                 230                 235                 240

Lys Gln Glu Leu Leu Asp Leu Leu His Asn Leu Glu Gln Thr Ile Glu
                245                 250                 255

Ala Lys Ile Gln Gln Ala Gln Glu Asp Glu Val Asn Ser Asn Ser Ala
            260                 265                 270

Ala Ala Asp Phe Lys Ser Lys Leu Glu His Glu Ile Gln Val Tyr Glu
        275                 280                 285

Arg Glu Leu Ala Lys Trp Gln Gln Thr Val Ala Ala Leu Thr Ala Thr
    290                 295                 300

Val Ala Gln Asp His Glu Asn Val Asn Asn Cys His Ser Gln Glu Ala
305                 310                 315                 320

Ala Ile Gln Ala Asn Leu Asp Ala Ala Asn Gln Asp Tyr Ala Asn Glu
                325                 330                 335

Lys Ala Thr Phe Glu His Lys Gln Ala Asn Leu Gln Glu Glu Ile Glu
            340                 345                 350

Ile Phe Ile Glu Val Ile Ala Tyr Tyr Asp Asp Asn Val Gln Asn Ala
        355                 360                 365

Gly Glu Asp Leu Lys Glu Arg Val Glu Asp Tyr Ser Asp Gly Asn Phe
    370                 375                 380

Asp Asp Ala Ala Thr Tyr Glu Asn Arg Gln Val Pro Asn Ile Asp Phe
385                 390                 395                 400

Ile Asn

<210> SEQ ID NO 2
<211> LENGTH: 417
<212> TYPE: PRT
<213> ORGANISM: Tetrahymena thermophila

<400> SEQUENCE: 2

Met Arg Leu Thr Val Ile Val Thr Leu Ser Leu Leu Phe Gly Cys Ile
1               5                   10                  15

Met Ala Ala Glu Ala Glu Ala Glu Leu Glu Ala Thr Tyr Glu Ile Asp
            20                  25                  30

Asn Ala Leu Glu Ala Leu Thr Glu Leu Arg Asp Asp Thr Ala Leu Ser
        35                  40                  45

Leu Tyr Asn Leu Gln Lys Gly Trp Ala Val Val Lys Asp Gly Leu Gln
    50                  55                  60

Asp Ser Glu Asn Gln Leu Gln Asn Ser Ile Asn Gln Lys Asp Ala Glu
65                  70                  75                  80

Cys Ala Asn Leu Asp Gln Ala Arg Asn Gln Thr Gln Ser Asp Leu Asp
                85                  90                  95
```

-continued

```
Glu Ile Asn Ala Tyr Ile Pro Trp Leu Glu Gln Lys Ile Ala Asn Ile
                100                 105                 110

Thr Asp Ser Leu Asn Ser Leu Leu Gln Arg Arg Cys Asp Leu Asn Lys
            115                 120                 125

Ala Phe Leu Asp His Ile Gln Arg Glu Lys Ile Ala Leu Ser Leu Leu
        130                 135                 140

Glu Phe Ile Lys Ser Ala Ile Gln Asn Lys Asp Ser Phe Asp Phe Val
145                 150                 155                 160

Gln Met Arg Lys Leu Asn Lys Asn Phe Gln Gln Phe Leu Ile Ala Tyr
                165                 170                 175

Ser Ala His Asp Phe Ser Ser Ile Leu Leu Gln Lys Asp Ile Val
            180                 185                 190

Asp Ser Lys Asp Tyr Glu Val Asp Val Asp Phe Ser Thr Lys Asp Arg
        195                 200                 205

Thr Glu Glu Glu Ile Gly Thr Gly His Ile Asp Asn Asn Lys Gly Asp
210                 215                 220

Leu Asp Leu Glu Asp Phe Thr Glu Gly Lys Arg Lys Asn Trp Gln Leu
225                 230                 235                 240

Tyr Lys Gln Glu Leu Leu Asp Ile Leu Asn Glu Leu Gln Ala Lys Ile
                245                 250                 255

Gln Ala Asn Ile Lys Ser Ser Ile Asp Asp Glu Ile Ala Ala Ser Val
            260                 265                 270

Thr Leu Ala Asn Tyr Lys Asn Asn Ala Leu Lys Glu Ile Gln Ala Tyr
        275                 280                 285

Glu Lys Glu Leu Ala Lys Ala Lys Lys Gln Val Gln Leu Gln Ala
290                 295                 300

Gln Leu Asp Asp Glu Gln Asn Ala Leu Thr Gln Cys Arg Ser Gln Asp
305                 310                 315                 320

Asp Ser Leu Lys Asn Gln Leu Gln Ser Leu Gln Asn Glu Ile Gln Gln
                325                 330                 335

Arg Gln Ala Glu Phe Asp Lys Lys Asp Asp Leu Gln Gly Gln Val
            340                 345                 350

Asp Leu Phe Asn Glu Ile Ile Thr Glu Tyr Gln Asp Gly Ile Phe Ser
        355                 360                 365

Gln Gly Asp Asp Phe Lys Gly Arg Thr Asp Asp Tyr Leu Asp Asn Gln
370                 375                 380

Thr Phe Asp Asp Asp Ala Thr Tyr Thr Gly Arg Glu Val Pro Lys Ile
385                 390                 395                 400

Asp Phe Met Asn Asn Gln Asp Ala Asn Gly Ser Ala Ser Ser Gly Gly
                405                 410                 415

Phe
```

<210> SEQ ID NO 3
<211> LENGTH: 377
<212> TYPE: PRT
<213> ORGANISM: Tetrahymena thermophila

<400> SEQUENCE: 3

```
Met Lys Asn Leu Ala Ile Val Leu Ala Ala Leu Cys Ile Phe Ala Gln
1               5                   10                  15

Ala Thr Ser Val Phe Glu Thr Pro Ala Phe Leu Glu Ile Lys Ser Asn
            20                  25                  30

Pro Phe Gly His Thr Val Ala Ser Leu Val Gln Leu Asn Leu Gly Ala
        35                  40                  45
```

```
Gly Gln Ser Ala Gly Arg Leu Asp Ala Ile Ala Glu Ala Leu Asn Thr
 50                  55                  60

Ile Glu Ala Gln Leu Glu Asn Thr Arg Asp His Asn Asp Ala Glu Ile
 65                  70                  75                  80

Gln Arg Gln Arg Gly Trp Cys Ser Asp Gln Glu Ala Thr Ile Gln Ala
                 85                  90                  95

Asn Ile Asp Gln Ala Glu Ser Asp Leu Ser Asn Tyr Gln Asn Glu Gln
            100                 105                 110

Thr Gln Arg Asn Gln Ala Val Ala Asp Leu Thr Gln Asn Leu Asn Asn
        115                 120                 125

Glu Gln Gln Ser Leu Ala Glu Asn Gln Asn Asn Leu Ala Asn Ala Gln
130                 135                 140

Gln Glu Leu Asp Asp Glu Asn Ser Ser Tyr Ala Glu Ser Ser Lys Asp
145                 150                 155                 160

Tyr Ala Asp Ala Ile Ala Ala Cys Glu Gln Ala Leu Lys Leu Leu Ala
                165                 170                 175

Thr Leu Gln Thr Asn Pro Ser Gly Phe Ile Gln Ser Lys Ala Arg Phe
            180                 185                 190

Gly Asn Val Val Thr Leu Leu Gln Lys His Leu Ala Asn Lys Ser Ser
        195                 200                 205

Asn Phe Val Gln Pro Ile Leu Asn Val Leu Thr Glu Met Ala Ser Ser
210                 215                 220

Thr Asn Glu Val Asp Gln Ser Ser Leu Ala Lys Val Val Ser Leu Ile
225                 230                 235                 240

Asn Asp Leu Leu Glu Glu Leu Arg Asn Gln Ser Ala Ala Asn Asp Gln
                245                 250                 255

Arg His Gln Gln Val Val Asp Ser Leu Thr Ser Asn Ile Ala Asn Leu
            260                 265                 270

Glu Gln Leu Ile Asp Asn Ser Asn Asn Leu Ile Ser Gln Tyr Gln Gly
        275                 280                 285

Gln Ile Gln Glu Asn Glu Asp Arg Leu Ala Gln Leu Ala Gly Leu Ile
290                 295                 300

Gln Gln Thr Gln Ala Ile Leu Asp Gln Ala Asn Gln Asn Leu Ser Gln
305                 310                 315                 320

Val Gln Asp Gln Cys Ala Gly Tyr Asp Gln Glu Tyr Ala Ser Phe Lys
                325                 330                 335

Asn Glu Val Asp Gln Gln Leu Ala Thr Leu Gln Ala Leu Lys Glu Tyr
            340                 345                 350

Phe Lys Ser Lys Val Val Pro Ala Val Glu Asn Ile Asn Asp Ser Ala
        355                 360                 365

Tyr Ala Asp Glu Leu Thr Val Asp Val
    370                 375

<210> SEQ ID NO 4
<211> LENGTH: 394
<212> TYPE: PRT
<213> ORGANISM: Tetrahymena thermophila

<400> SEQUENCE: 4

Met Arg Tyr Ala Ala Leu Phe Leu Leu Ala Leu Ile Ser Phe Asn Ala
 1               5                  10                  15

Val Tyr Ala Val Ser Leu Arg Lys Ser Ser Asp Ala Met Lys Thr Ser
             20                  25                  30

Phe Ala Leu Glu Arg Leu Arg Phe Ile Gly Lys Lys Ser Pro Ile Ala
         35                  40                  45
```

Lys Gln Ile Ile Ser Ala Val Glu Leu His Leu Thr Thr Gly Gly Leu
    50                  55                  60

Val Asp Asp Val Ile Asp Leu Val Lys Gln Ala Gln Glu Asp Val Ala
65                  70                  75                  80

Asn Arg Asn Val Ala Leu Gln Ala Glu Tyr Thr Ala Lys Arg Gly Ala
                85                  90                  95

Leu Glu Asp Gln Ile Asn Thr Thr Thr Gln Leu Asn Glu Glu Asn
            100                 105                 110

Asp Arg Leu Ala Val Val Asn Asp Ala Ile Asp Ala Leu Asn Gly Gln
            115                 120                 125

Ile Asp Ser Leu Asn Thr Gln Ile Ala Asn Leu Val Gln Gln Leu Gln
            130                 135                 140

Asn Leu Gln Ala Arg Glu Asp Ala Ile Asn Gln Ala Arg Glu Val Asp
145                 150                 155                 160

Val Lys Thr Tyr Glu Val Arg Lys Gln Arg Asp Glu Asn Ser Leu Ala
                165                 170                 175

Val Leu Glu Gln Ile Ile Gln Arg Leu Leu Ala Leu Gln Gln Arg Gly
            180                 185                 190

Asn Ala Phe Leu Gln Val Ser Lys Lys Glu Ile Glu Arg Ile Leu Lys
            195                 200                 205

Arg Ile Pro Lys Ser Asn Pro Ile Gln Ala Leu Val Gln Leu Ser Thr
210                 215                 220

Lys Phe Asp Glu Gln Arg Leu Ala Glu Val Ile Ser Lys Leu Gln Thr
225                 230                 235                 240

Ile Gln Ala Ala Ile Gln Ala Ser Tyr Ile Glu Asp Ala Asn Gly Glu
            245                 250                 255

Val Ala Asp Lys Gln Arg Tyr Asp Ala Leu Ile Gln Glu Ile Ala Thr
            260                 265                 270

Ile Arg Ala Gln Thr Gln Gln Leu Ala Asp Ala Gln Gln Ala Leu
            275                 280                 285

Ser Asp Ala Glu Ala Ser Leu Ala Gln Phe Val Gln Glu Gln Gly Asn
            290                 295                 300

Leu Gln Gln Gln Ile Ala Val Asn Glu Gly Ile Leu Ala Asp Ala Gln
305                 310                 315                 320

Ala Ala Leu Ala His Thr Ile Ala Thr Tyr Glu Ala Arg Ile Gln Glu
                325                 330                 335

Gly Gln Glu Ala Leu Ala Ala Ile Asn Leu Ala Leu Asp Val Leu Gln
            340                 345                 350

Gln Asn Gln Ser Asp Leu Gln Gly Val Glu Asp Phe Ser Asn Ala Tyr
            355                 360                 365

Asn Ala Tyr Gln Ala Gly Asn Ser Thr Asp Ala Gly Asp Ala Gly
            370                 375                 380

Asp Asp Ser Gly Val Glu Gly Glu Ala Phe
385                 390

<210> SEQ ID NO 5
<211> LENGTH: 377
<212> TYPE: PRT
<213> ORGANISM: Tetrahymena thermophila

<400> SEQUENCE: 5

Met Arg Val Ile Ala Ala Leu Leu Val Ile Ala Leu Val Cys Gln Ser
1               5                   10                  15

Ala Met Ala Val Thr Ser Lys Ser Gln Ala Lys Leu Met Met Glu Lys

```
                    20                  25                  30
Ile Asn Ser Lys Leu Glu Lys Ser His Leu Gly Arg Ala Leu Lys Gly
            35                  40                  45

Met Val Thr Ile Ala Thr Lys Leu Gly Tyr Asp Tyr Gln Asp Leu Tyr
    50                  55                  60

Asp Ala Phe Ala Ala Leu Lys Asn Gln Leu Leu Asn Asn Leu Asp Asn
65                  70                  75                  80

Glu Asn Ser Leu Phe Glu Thr Gln Thr Ala Ser His Asp Ser Ala Val
                85                  90                  95

Ala Gln Phe Asn Ala Asp Ile Ser Asn Tyr Asn Gly Gln Ile Asn Asp
            100                 105                 110

Ala Gln Ala Gln Leu Asn Asp Leu Asn Asp Ser Leu Asn Thr Tyr Gln
        115                 120                 125

Gln Asn Leu Gln Asp Ala Gln Gln Ala Leu Gln Asp Asn Thr Asp Ala
    130                 135                 140

Leu Asn Ala Ala Glu Glu Ala Leu Ala Asn Ala Glu Ala Leu Tyr Gln
145                 150                 155                 160

Val Ala Thr Ala Glu Tyr Ser Asn Ala Asp Gln Val Ile Gly Leu Ala
                165                 170                 175

Val Glu Lys Leu Gln Glu Ala Gln Ser His Tyr Asp Asn Ala Asp Leu
            180                 185                 190

Gly Ser Phe Ser Phe Val Gln Ile Lys Asn Thr Phe Val Ser Phe Ala
        195                 200                 205

Gln Lys Val Thr Glu Ala Thr Lys Gly Met Asn Ala Lys His Gln Leu
    210                 215                 220

Phe Val Lys Pro Val Val Gln Ala Met Met Gln Val Lys Asn Asn Thr
225                 230                 235                 240

Ser Gln Ser Ser Ile Gln Thr Ala Ile Lys Ala Leu Gln Asp Leu Gln
                245                 250                 255

Ala Tyr Phe Gln Lys Thr Phe Ser Asp Leu Thr Asn Glu Tyr Val Ser
            260                 265                 270

Phe Thr Gln Asn Val Gln Ser Thr Ile Asp Gly Leu Asn Gln Ile Ile
        275                 280                 285

Asp Ile Leu Gln Asn Gln Val Ile Pro Gly Tyr Glu Ala Gln Ile Ser
    290                 295                 300

Ser Leu Gln Ala Gln Ile Gln Gln Val Glu Asp Ala Leu Ala Leu Ala
305                 310                 315                 320

Gln Gln Asn Leu Gln Asp Ala Gln Asn Ala Leu Asp Ala Glu Asn Ala
                325                 330                 335

Gln Trp Glu Asn Val Val Ala Arg His Gln Ala Leu Val Asp Arg Ile
            340                 345                 350

Asn Ser Glu Tyr Asp Leu Val Thr Gln Ala Asp Arg Ile Val Arg Asn
        355                 360                 365

Ala Gln Ala Gln Val Asn Gly Ser Asp
    370                 375

<210> SEQ ID NO 6
<211> LENGTH: 890
<212> TYPE: PRT
<213> ORGANISM: Tetrahymena thermophila

<400> SEQUENCE: 6

Met Leu Leu Glu Tyr Leu Asn Leu Asn Ile Leu Arg Leu Thr Pro His
1               5                   10                  15
```

```
Ile Lys Arg Asn Gly Ile Val Asn Ser Asn Ser Asn Lys Leu Gln Arg
         20                  25                  30

Cys Ser Leu Leu Ile Ser Glu Asn Ile Leu Ser Gln Asn Lys Lys Phe
             35                  40                  45

Val Ser Ile Ile Gln Phe Phe Leu Arg Asp Ile Tyr Leu Glu Gln Tyr
 50                  55                  60

Leu Lys Lys Tyr Gln Asn Gln Gln Leu Lys Asn Gln Ile Tyr Ile Leu
 65                  70                  75                  80

Leu Gln Tyr Val Phe Asn Ile Leu Asn Gln Ile Glu Lys Ser Arg Phe
                 85                  90                  95

Gly Arg Asn Ile Leu Asp Thr Ile Gln Leu Gln Leu Ser Val Asn Asp
             100                 105                 110

Gln Ile Gly Arg Leu Val Ser Asp Leu Gln Asn Ile Ala Thr Asp Ile
         115                 120                 125

Gln Asn Asp Gln Ala Gln Asp Gln Lys Gln Thr Glu Arg Ile Gln Gln
130                 135                 140

Asp Cys Ser Asn Asp Leu Ser Arg Leu Glu Asp Glu Ile Gln Asp Ala
145                 150                 155                 160

Asn Leu Lys Val Ile Glu Ser Thr Ser Asp Ile Thr Glu Asn Thr Pro
                165                 170                 175

Ile Leu Glu Gln Lys Lys Ile Leu Leu Lys Gln Lys Ser Glu Ser Leu
            180                 185                 190

Thr Ala Asn Gln Gln Ile Leu Ser Asp Leu Asp Gln Asn Tyr Glu Lys
        195                 200                 205

Lys Ser Ala Glu Tyr Glu Ala Glu Arg Glu Glu His Ser Lys Ala Glu
210                 215                 220

Ser Val Ile Arg Glu Ala Lys Glu Ile Leu Gln Gly Thr Phe Gly Ser
225                 230                 235                 240

Thr Lys Ser Phe Ile Ser Ile Lys Lys Pro Ser Val Gln Ser Phe Val
                245                 250                 255

Gln Val Ser Asn His Phe Ser His His Ser Lys Thr Asn Tyr Lys Arg
            260                 265                 270

Lys Ser Trp Asn Ser Phe Phe Arg Ile Leu Ser Gln Leu Ser Gln Ser
        275                 280                 285

Ala Pro Ile Gln Ala Asp Pro Gly Ala Leu Gln Lys Leu Phe Glu Val
290                 295                 300

Ile Asp Glu Leu Leu Glu Lys Ile Ala Asp Ser Leu Glu Ile Glu Ala
305                 310                 315                 320

Lys Ala Phe Glu Gln Phe Glu Gln Asp Tyr Glu Asn Lys Lys Asp Asp
                325                 330                 335

Ile Leu Asp Arg Ile Gly Val Leu Gln Lys Val Ile Gly Glu Leu Asp
            340                 345                 350

Gly Glu Ile Ser Ser Leu Glu Ala Gln Leu Gln Glu Asp Ala Arg Val
        355                 360                 365

Lys Gln Val Gln Gln Glu Arg Ser Glu Lys Gln Thr Glu Leu Asn
370                 375                 380

Ser Arg Gln Ala Phe Cys Thr Asp Gln Ser Gln Phe Glu Ser Arg
385                 390                 395                 400

Thr Gln Glu Arg Arg Cys Leu Asn Lys Asn Arg Val Asn Thr Leu Lys
                405                 410                 415

Leu Phe Gln Lys Phe Lys Gln Gln Ile Asn Ile Asp Arg Leu Thr Asn
            420                 425                 430

Ser Gln Gln Thr Thr Tyr Phe Lys Asn Lys Lys Glu Arg Lys Ile Met
```

-continued

```
            435                 440                 445
Glu Gln Ile Ser Leu Gln Ile Gln Asn Ser Leu Glu Glu Ala Ile Ser
450                 455                 460
Ile Leu Lys Ile Ile Ser Asn Ser Gln Glu Lys Gly Leu Ile Leu Thr
465                 470                 475                 480
Asp Ile Leu Ile Asn Asp Ile Tyr Phe Ile Arg Asn Leu Ile Leu Ser
                485                 490                 495
Gly Lys Glu Glu Gln Leu Asn Asn Tyr Phe Gln Asp Leu Asn Ile Ile
            500                 505                 510
Val Asp Lys Ala Lys Leu Ile Lys Asn Asn Leu Thr Phe Ser Cys Val
515                 520                 525
Ser Lys Tyr Gly Asn Phe Ile Gln Ile Phe Gln Gln Glu Pro Ile Lys
530                 535                 540
Val Ile Phe Gln Lys Ile Asn Ser Ile Leu Gln Asn Ile Lys Lys Gln
545                 550                 555                 560
Phe Pro Lys Gln Ile Asp Ser Asn Asp Val Tyr Ser Leu Asp Ser Lys
                565                 570                 575
Lys Ile Glu Gln Ile Phe Lys Leu His Ser Lys Leu Gln Thr Phe Arg
            580                 585                 590
Gln Tyr Gln Asn Met Asn Gln Phe Gln Ser Tyr His Gln Leu Thr Val
            595                 600                 605
Leu Phe Lys Met Cys Asn Asp Gln Gln Gly Glu Arg Glu Ser Leu Leu
610                 615                 620
Lys Ser Ile Ala Ser Phe Ile Leu Pro Thr Ser Cys Leu Thr Ser Gln
625                 630                 635                 640
Asn Lys Gln Ile Ala Ile Glu Gln Tyr Ile Pro Leu Lys Asp Leu Lys
                645                 650                 655
Leu Lys Ile Cys Asn Gly Asp Phe Glu Gly Val Ile Gln Ser Ser Gln
            660                 665                 670
Ser Leu Leu Leu Glu Lys Asn Lys Leu Gln Ile Ile Gly Glu Arg Lys
            675                 680                 685
Val Ser Glu Met Asn Tyr Gln His Ser Val Asn Gln Ile Gln Pro Tyr
690                 695                 700
Cys Ile Asp Cys Ile Leu Leu Thr Pro Ile Ser Arg Ser Leu Asn Cys
705                 710                 715                 720
Leu Leu Val Glu Gly Gln Glu Ile Asn Leu Asn Tyr Gly Glu Gln Ile
                725                 730                 735
Lys Glu Tyr Ser Ile Cys His Asp Ser Met Lys Leu Lys Leu Ile Ile
            740                 745                 750
Asn Met Glu Lys Glu Thr Met Gln Lys Asn Leu Tyr Ala Leu Ile Asp
            755                 760                 765
Glu Asn Gln Met Lys Gln Lys Asp Ala Gln Asp Asn Met Gln Asn Leu
770                 775                 780
Glu Thr Glu Thr Asn Thr Asn Asn Thr Ser Asn Gln Gln Ile Asp Tyr
785                 790                 795                 800
Phe Glu Glu Thr Glu Asp Tyr Asp Asn Lys Met Leu Asn Leu His Asn
                805                 810                 815
Gln Tyr Asn Leu Gln Asp Arg Glu Ala Val Ser Phe Phe Ser Lys Phe
            820                 825                 830
Ala His Thr Ser Lys Ile Glu Arg Leu Lys Thr Asp Lys Met Asp Trp
            835                 840                 845
Ile Glu Lys Gln Arg Asn His Ile His Pro Ser Ile Gln Lys Leu Ile
            850                 855                 860
```

```
Gln Ile Phe Asn Gln Ile Lys Ser Asn Gln Ser Ile His Pro Ser Ile
865                 870                 875                 880

His Gln Ser Phe His Leu Phe Asp Tyr Phe
                885                 890

<210> SEQ ID NO 7
<211> LENGTH: 385
<212> TYPE: PRT
<213> ORGANISM: Tetrahymena thermophila

<400> SEQUENCE: 7

Met Arg Lys Val Phe Val Ala Leu Ala Leu Val Ala Ile Ile Val Ser
1               5                   10                  15

Ala Thr Met Leu Pro Glu Val Arg Gln Arg Ala Lys Val Ser Leu Gln
                20                  25                  30

Lys Leu His Lys Ser Arg Ile Gly Lys Asn Ile Val Thr Ala Ile Gln
                35                  40                  45

Leu Glu Leu Ser Ser Lys Asn Arg Asp Asn Ile Ile Val Asn Ile Leu
            50                  55                  60

Ala Leu Leu Asn Asp Leu Leu Asn Asp Gln Ser Thr Gln Leu Thr Lys
65                  70                  75                  80

Ala Gln Ser Asp Leu Ala Asp Lys Gln Asp Tyr Cys Gly Ser Ser Ile
                85                  90                  95

Glu Ser Tyr Gln Asn Gln Ile Ala Ser Lys Gln Ala Asp Ile Ala Asn
                100                 105                 110

Ala Gln Ala Ser Leu Pro Ala Leu His Ala Glu Leu Glu Thr Asp Gln
                115                 120                 125

Ala Asn Leu Ala Asp Gln Glu Ala Lys Leu Asp Arg Ala Gln Gln Asn
            130                 135                 140

Leu Ala Glu Ala Asn Asp Leu Asn Asp Ala Ala Val Ala Ala Phe Asn
145                 150                 155                 160

Thr Ser Ile Ala Asn His Asn Ala Met Ile Asp Ala Leu Lys Gln Ala
                165                 170                 175

Arg Ala Leu Ile Val Gln Leu Gln Ser Ser Ser Phe Leu Gln Lys Asn
                180                 185                 190

Asn Ala Val Leu Ile Gln Leu Ser Asn His Lys Ala Leu Ala Leu Lys
                195                 200                 205

Lys Leu Glu Gly His Ala Lys Lys Ser Leu Phe Ser Leu Leu Met Gln
            210                 215                 220

Met Ala Gln Asp Val Gly Ile Gln Ala Asp Gln Thr Leu Val Gly Asn
225                 230                 235                 240

Val Leu Thr Val Ile Asp Asp Leu Leu Gln His Glu Gln Asp Gly Ile
                245                 250                 255

Asp Ala Glu Thr Gln Ala Glu Asn Gln Arg Val Glu Glu Tyr Asn Ala
                260                 265                 270

Ala Val Ile Asp Phe Asn Asn Gln Ile Ser Asp Ala Gln Gly Gln Ile
                275                 280                 285

Ala Ser Leu Asn Gln Asp Ile Gln Thr Leu Thr Asn Asn Ile Asn Asp
            290                 295                 300

Thr Glu Asn Asn Ile Ala Thr Trp Ser Gln Val Ser Asp Leu Gln
305                 310                 315                 320

Gly Val Leu Asp Glu Leu Gln Asn Gln Cys Asn Ala Asp Ile Ala His
                325                 330                 335

Phe Gln Asp Leu Ile Gln Glu Leu Asn Gly Ile Ile Asp Ile Ile Gln
```

```
                    340                 345                 350
Gln Val Ile Ala Ile Phe Glu Gly Gln Ser Ile Gln Asp Val Lys Pro
            355                 360                 365

Leu Phe Asp Asp Ile Ser Val Asp Asp Gly Leu Gly Ser Ala Glu Ser
    370                 375                 380

Ala
385

<210> SEQ ID NO 8
<211> LENGTH: 399
<212> TYPE: PRT
<213> ORGANISM: Tetrahymena thermophila

<400> SEQUENCE: 8

Met Asn Lys Ala Leu Val Phe Leu Ala Ile Ile Ala Leu Gly Phe Ala
1               5                   10                  15

Ala Ser Thr Gln Gln Val Ser Ala Leu Asp Pro Ser Glu Asn Ala Ala
            20                  25                  30

Asp Ala Leu Ile Asp Gln Leu Asn Gln Met Glu Gly Ala Ile Arg Lys
        35                  40                  45

Glu Gln Gln Ala His Asp Glu Leu Ala Gln Gln Asp Ala Glu Cys
    50                  55                  60

Ala Gln Glu Phe Gln Phe Arg Gln Asn Glu Ile Asn Asp Ala Gln Asn
65                  70                  75                  80

Ala Phe Asp Ala Ala Asn Ala Ala Gly Arg Cys Gln Asn Ala Leu
                85                  90                  95

Thr Ala Ser Gln Ala Asp Leu Glu Lys Ala Asn Asn Tyr Val Ser Ser
            100                 105                 110

Ile Gln Gln Ile Leu Ala Gly Leu Ala Ser Gln Arg Leu Ala Glu His
        115                 120                 125

Asn Ala Tyr Glu Asp Leu Val Asn Asn Gln Leu Gln Pro Ala Ile Asp
    130                 135                 140

Ala Val Gln Gly Ala Tyr Pro Ile Leu Ser Asp Phe Ala Ser Gln Thr
145                 150                 155                 160

Val Ser Phe Val Gln Phe Ser Asn His Ile Asn Lys Met Phe Leu Gln
                165                 170                 175

Met Val Lys Ala Asn Lys Val Asn Ser Phe Thr Ala Ile Leu Thr Val
            180                 185                 190

Leu Leu Ser Gln Pro Asp Phe Gln His Gly Val Gly Arg Asp Ala Ile
        195                 200                 205

Asp Gln Leu Gln Ala Leu Phe Glu Gln Leu Glu Gln Asp Leu Gln Ala
    210                 215                 220

Ala Leu Asp His Ala Thr Glu Val Glu Asn Asn Ala Val Gln Val Tyr
225                 230                 235                 240

Asn Asp Thr Val Asn Glu Tyr Asn Ala Val Leu Ala Thr Leu Asp Ala
                245                 250                 255

Thr Ile Ser Ser Leu Asn Asp Tyr Ile Ser Ser Leu Glu Asn Cys Val
            260                 265                 270

Gln Asn Glu Asn Ser Ile Ala Ser Gln Ala Asn Ala Lys Lys Val Arg
        275                 280                 285

Asn Ser Asp Ala Leu Ala Tyr Ala Val Asp Met Cys Gln Ala Phe Asp
    290                 295                 300

Thr Glu Tyr Gln Asn Ala Thr Ala Ala Arg Asn Asp Glu Leu Ala Leu
305                 310                 315                 320
```

```
Leu Gln Lys Leu Glu Asn Phe Val His Glu Gln Ala Asp Ile Phe Gly
                325                 330                 335

Asp Tyr Gly Thr Asp Asn Val Asp Ala Phe Asp Phe Lys Gln Ser
            340                 345                 350

Tyr Asp Ala Gln Arg Asp Thr Gln Arg Gly Asn Phe Met Gln Met Lys
            355                 360                 365

Ile Lys Gln Phe Lys Met Asn Ser Asn Phe Lys Val Ala Lys Cys
370                 375                 380

Glu Ser Cys Ser Arg Lys Ser Phe Val Gln Lys Lys Leu Gly Phe
385                 390                 395
```

<210> SEQ ID NO 9
<211> LENGTH: 377
<212> TYPE: PRT
<213> ORGANISM: Tetrahymena thermophila

<400> SEQUENCE: 9

```
Met Arg Val Ile Ala Ala Leu Leu Val Ile Ala Leu Val Cys Gln Ser
1               5                   10                  15

Ala Met Ala Val Thr Ser Lys Ser Gln Val Lys Leu Met Met Glu Lys
                20                  25                  30

Ile Asn Ser Lys Met Glu Lys Ser Pro Leu Gly Arg Ala Leu Lys Gly
            35                  40                  45

Met Val Thr Ile Ala Thr Lys Leu Gly Tyr Asp Tyr Gln Asp Leu Tyr
50                  55                  60

Asp Ala Phe Ala Ala Leu Lys Asn Gln Leu Leu Asn Ser Leu Asp Asn
65                  70                  75                  80

Glu Asn Ser Leu Phe Glu Glu Gln Thr Ala Cys His Glu Asn Phe Ile
                85                  90                  95

Ala Gln Phe Asn Ala Leu Ile Ser Asn Tyr Thr Ser Gln Ile Asn Asp
            100                 105                 110

Thr Glu Ala Gln Leu Asn Tyr Leu Asn Asp Ser Leu Asn Thr Tyr Glu
        115                 120                 125

Gln Asn Leu Lys Asp Ala Gln Gln Ala Leu Gln Asp Asn Thr Asp Ala
    130                 135                 140

Leu Asn Ala Ala Glu Glu Ala Leu Ala Gln Ala Glu Val Leu Tyr His
145                 150                 155                 160

Tyr Ala Thr Ala Glu Tyr Ser Asn Ala Asp Gln Val Ile Gly Val Ala
                165                 170                 175

Ile Glu Lys Leu Gln Glu Ala Gln Ser His Tyr Asp Asn Ala Asp Leu
            180                 185                 190

Gly Ser Phe Ser Phe Val Gln Ile Lys Asn Thr Phe Val Ser Phe Ala
        195                 200                 205

Gln Lys Ile Thr Glu Ala Thr Lys Gly Met Asn Ala Lys His Gln Leu
    210                 215                 220

Phe Val Lys Pro Val Val Gln Ala Met Met Gln Val Lys Asn Asn Thr
225                 230                 235                 240

Ser Gln Thr Ser Ile Gln Thr Ala Ile Lys Ala Leu Gln Asp Leu Gln
                245                 250                 255

Ala Tyr Phe Gln Lys Thr Phe Thr Asp Leu Thr Asn Glu Tyr Val Ile
            260                 265                 270

Phe Thr Gln Asn Val Gln Ser Thr Ile Asp Gly Leu Asn Gln Leu Ile
        275                 280                 285

Asp Ile Leu Gln Asn Gln Thr Ile Pro Gly Tyr Glu Ser Gln Ile Ser
    290                 295                 300
```

```
Gln Ile Gln Ala Gln Ile Gln Phe Glu Asp Ala Leu Ser Leu Ala
305                 310                 315                 320

Gln Gln Asn Leu Lys Gln Ala Gln Asp Tyr Ile Ser Ala Glu Tyr Glu
            325                 330                 335

Ile Phe Ala Ile Val Gln Ala Arg His Gln Ala Leu Val Asp Arg Ile
            340                 345                 350

Asn Ser Glu Tyr Asp Leu Val Thr Gln Ala Asp Arg Ile Val Arg Asn
            355                 360                 365

Ala Gln Ala Gln Val Asn Tyr Ser Asn
            370                 375

<210> SEQ ID NO 10
<211> LENGTH: 448
<212> TYPE: PRT
<213> ORGANISM: Plasmodium falciparum

<400> SEQUENCE: 10

Met Met Leu Tyr Ile Ser Ala Lys Lys Ala Gln Val Ala Phe Ile Leu
1               5                   10                  15

Tyr Ile Val Leu Val Leu Arg Ile Ile Ser Gly Asn Asn Asp Phe Cys
            20                  25                  30

Lys Pro Ser Ser Leu Asn Ser Glu Ile Ser Gly Phe Ile Gly Tyr Lys
            35                  40                  45

Cys Asn Phe Ser Asn Glu Gly Val His Asn Leu Lys Pro Asp Met Arg
        50                  55                  60

Glu Arg Arg Ser Ile Phe Cys Thr Ile His Ser Tyr Phe Ile Tyr Asp
65                  70                  75                  80

Lys Ile Arg Leu Ile Ile Pro Lys Lys Ser Ser Pro Glu Phe Lys
                85                  90                  95

Ile Leu Pro Glu Lys Cys Phe Gln Lys Val Tyr Thr Asp Tyr Glu Asn
            100                 105                 110

Arg Val Glu Thr Asp Ile Ser Glu Leu Gly Leu Ile Glu Tyr Glu Ile
            115                 120                 125

Glu Glu Asn Asp Thr Asn Pro Asn Tyr Asn Glu Arg Thr Ile Thr Ile
130                 135                 140

Ser Pro Phe Ser Pro Lys Asp Ile Glu Phe Phe Cys Phe Cys Asp Asn
145                 150                 155                 160

Thr Glu Lys Val Ile Ser Ser Ile Glu Gly Arg Ser Ala Met Val His
                165                 170                 175

Val Arg Val Leu Lys Tyr Pro His Asn Ile Leu Phe Thr Asn Leu Thr
            180                 185                 190

Asn Asp Leu Phe Thr Tyr Leu Pro Lys Thr Tyr Asn Glu Ser Asn Phe
            195                 200                 205

Val Ser Asn Val Leu Glu Val Glu Leu Asn Asp Gly Glu Leu Phe Val
210                 215                 220

Leu Ala Cys Glu Leu Ile Asn Lys Lys Cys Phe Gln Glu Gly Lys Glu
225                 230                 235                 240

Lys Ala Leu Tyr Lys Ser Asn Lys Ile Ile Tyr His Lys Asn Leu Thr
            245                 250                 255

Ile Phe Lys Ala Pro Phe Tyr Val Thr Ser Lys Asp Val Asn Thr Glu
            260                 265                 270

Cys Thr Cys Lys Phe Lys Asn Asn Tyr Lys Ile Val Leu Lys Pro
            275                 280                 285

Lys Tyr Glu Lys Lys Val Ile His Gly Cys Asn Phe Ser Ser Asn Val
```

```
                290                 295                 300
Ser Ser Lys His Thr Phe Thr Asp Ser Leu Asp Ile Ser Leu Val Asp
305                 310                 315                 320

Asp Ser Ala His Ile Ser Cys Asn Val His Leu Ser Glu Pro Lys Tyr
                325                 330                 335

Asn His Leu Val Gly Leu Asn Cys Pro Gly Asp Ile Ile Pro Asp Cys
            340                 345                 350

Phe Phe Gln Val Tyr Gln Pro Glu Ser Glu Leu Glu Pro Ser Asn
        355                 360                 365

Ile Val Tyr Leu Asp Ser Gln Ile Asn Ile Gly Asp Ile Glu Tyr Tyr
        370                 375                 380

Glu Asp Ala Glu Gly Asp Lys Ile Lys Leu Phe Gly Ile Val Gly
385                 390                 395                 400

Ser Ile Pro Lys Thr Thr Ser Phe Thr Cys Ile Cys Lys Lys Asp Lys
                405                 410                 415

Lys Ser Ala Tyr Met Thr Val Thr Ile Asp Ser Ala Tyr Tyr Gly Phe
                420                 425                 430

Leu Ala Lys Thr Phe Ile Phe Leu Ile Val Ala Ile Leu Leu Tyr Ile
            435                 440                 445

<210> SEQ ID NO 11
<211> LENGTH: 761
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Ser Lys Phe Asn Ile Leu Ile Ile Leu Ile Ile Ser Leu Phe
1               5                   10                  15

Ile Asn Glu Leu Arg Ala Asp Asn Thr Glu Lys Val Ile Ser Ser Ile
            20                  25                  30

Glu Gly Arg Ser Ala Met Val His Val Arg Val Leu Lys Tyr Pro His
        35                  40                  45

Asn Ile Leu Phe Thr Asn Leu Thr Asn Asp Leu Phe Thr Tyr Leu Pro
    50                  55                  60

Lys Thr Tyr Asn Glu Ser Asn Phe Val Ser Asn Val Leu Glu Val Glu
65                  70                  75                  80

Leu Asn Asp Gly Glu Leu Phe Val Leu Ala Cys Glu Leu Ile Asn Lys
                85                  90                  95

Lys Cys Phe Gln Glu Gly Lys Glu Lys Ala Leu Tyr Lys Ser Asn Lys
            100                 105                 110

Ile Ile Tyr His Lys Asn Leu Thr Ile Phe Lys Ala Pro Phe Tyr Val
        115                 120                 125

Thr Ser Lys Asp Val Asn Thr Glu Cys Thr Cys Lys Phe Lys Asn Asn
130                 135                 140

Asn Tyr Lys Ile Val Leu Lys Pro Lys Tyr Glu Lys Lys Val Ile His
145                 150                 155                 160

Gly Cys Asn Phe Ser Ser Asn Val Ser Ser Lys His Thr Phe Thr Asp
                165                 170                 175

Ser Leu Asp Ile Ser Leu Val Asp Asp Ser Ala His Ile Ser Cys Asn
            180                 185                 190

Val His Leu Ser Glu Pro Lys Tyr Asn His Leu Val Gly Leu Asn Cys
        195                 200                 205
```

Pro Gly Asp Ile Ile Pro Asp Cys Phe Phe Gln Val Tyr Gln Pro Glu
210                 215                 220

Ser Glu Glu Leu Glu Pro Ser Asn Ile Val Tyr Leu Asp Ser Gln Ile
225                 230                 235                 240

Asn Ile Gly Asp Ile Glu Tyr Tyr Glu Asp Ala Glu Gly Asp Asp Lys
                245                 250                 255

Ile Lys Leu Phe Gly Ile Val Gly Ser Ile Pro Lys Thr Thr Ser Phe
            260                 265                 270

Thr Cys Ile Cys Lys Lys Asp Lys Ser Ala Tyr Met Thr Val Thr
        275                 280                 285

Ile Asp His His His His His His Cys Pro Ala Gly Thr Val Val Asp
    290                 295                 300

Asp Gly Thr Ser Thr Asn Phe Val Ala Leu Ala Ser Glu Cys Thr Lys
305                 310                 315                 320

Cys Gln Ala Asn Phe Tyr Ala Ser Lys Thr Ser Gly Phe Ala Ala Gly
                325                 330                 335

Thr Asp Thr Cys Thr Glu Cys Ser Lys Lys Leu Thr Ser Gly Ala Thr
            340                 345                 350

Ala Lys Val Tyr Ala Glu Ala Thr Gln Lys Ala Gln Cys Ala Ser Thr
        355                 360                 365

Asn Gln Ser Glu Glu Glu Gly Ser Tyr Thr Ile Asp Gln Ala Ala Asn
370                 375                 380

Leu Leu Asn Asp Leu Leu Ala Asp Ser Gln Gln Asn Leu Ser Asp Leu
385                 390                 395                 400

Gln Ala Ala Trp Ala Asn Lys Glu Pro Leu Leu Gln Gly Val Ile Ala
                405                 410                 415

Gly Leu Glu Ser Asp Leu Ala Asn Lys Gln Ala Glu Cys Ala Asp Leu
            420                 425                 430

Gln Gly Thr Leu Asp Ala Asp Gln Ala Ser Leu Asp Glu Ala Glu Ala
        435                 440                 445

Tyr Val Ala Trp Leu Gln Asp Arg Ile Ala Ala Asn His Lys Gln Ile
450                 455                 460

Asp Asp Leu Leu Asn Arg Arg Cys Gln Gln Asn Gly Asn Tyr Ile Glu
465                 470                 475                 480

Gly Leu Lys Asn Asp Lys Leu Ala Leu Ala Leu Leu Gln Phe Leu Glu
                485                 490                 495

Ala Gln Ile Gln Asn Lys Glu Ser Phe Ser Phe Leu Gln Lys Lys Asn
            500                 505                 510

Phe Met Lys Lys Leu Thr Arg Phe Leu Ser Ile Tyr Lys Thr Gly Asn
        515                 520                 525

Tyr Gln Gln Leu Ala Leu Leu Glu Lys Glu Tyr Val Asn Ala Asp Asp
530                 535                 540

Tyr Ser Val Asn Pro Asp Tyr Ser Thr Gly Asp Arg Thr Ala Asp Glu
545                 550                 555                 560

Ile Gly Ser Gly His Ile Asp Asn Asp Lys Gly Asp Ile Asp Val Ala
                565                 570                 575

Asp Phe Gln Glu Gly Glu Arg Lys Gly Trp Tyr Gln Val Lys Gln Glu
            580                 585                 590

Leu Leu Asp Leu His Asn Leu Glu Gln Thr Ile Glu Ala Lys Ile
        595                 600                 605

Gln Gln Ala Gln Glu Asp Glu Val Asn Ser Asn Ser Ala Ala Ala Asp
610                 615                 620

Phe Lys Ser Lys Leu Glu His Glu Ile Gln Val Tyr Glu Arg Glu Leu

```
            625                 630                 635                 640
Ala Lys Trp Gln Gln Thr Val Ala Ala Leu Thr Ala Thr Val Ala Gln
                    645                 650                 655

Asp His Glu Asn Val Asn Asn Cys His Ser Gln Glu Ala Ala Ile Gln
                    660                 665                 670

Ala Asn Leu Asp Ala Ala Asn Gln Asp Tyr Ala Asn Glu Lys Ala Thr
                    675                 680                 685

Phe Glu His Lys Gln Ala Asn Leu Gln Glu Ile Glu Ile Phe Ile
                    690                 695                 700

Glu Val Ile Ala Tyr Tyr Asp Asp Asn Val Gln Asn Ala Gly Glu Asp
705                 710                 715                 720

Leu Lys Glu Arg Val Glu Asp Tyr Ser Asp Gly Asn Phe Asp Asp Ala
                    725                 730                 735

Ala Thr Tyr Glu Asn Arg Gln Val Pro Asn Ile Asp Phe Ile Asn His
                    740                 745                 750

His His His His His His His
                    755                 760

<210> SEQ ID NO 12
<211> LENGTH: 567
<212> TYPE: PRT
<213> ORGANISM: Influenza A virus

<400> SEQUENCE: 12

Met Glu Lys Ile Val Leu Leu Phe Ala Ile Val Ser Leu Val Lys Ser
1                   5                   10                  15

Asp Gln Ile Cys Ile Gly Tyr His Ala Asn Asn Ser Thr Glu Gln Val
                    20                  25                  30

Asp Thr Ile Met Glu Lys Asn Val Thr Val Thr Ala Gln Asp Ile Leu
                    35                  40                  45

Glu Lys Thr His Asn Gly Lys Leu Cys Asp Leu Asp Gly Val Lys Pro
                    50                  55                  60

Leu Ile Leu Arg Asp Cys Ser Val Ala Gly Trp Leu Leu Gly Asn Pro
65                  70                  75                  80

Met Cys Asp Glu Phe Ile Asn Val Pro Glu Trp Ser Tyr Ile Val Glu
                    85                  90                  95

Lys Ala Asn Pro Val Asn Asp Leu Cys Tyr Pro Gly Asp Phe Asn Asp
                    100                 105                 110

Tyr Glu Glu Leu Lys His Leu Leu Ser Arg Ile Asn His Phe Glu Lys
                    115                 120                 125

Ile Gln Ile Ile Pro Lys Ser Ser Trp Ser Ser His Glu Ala Ser Leu
                    130                 135                 140

Gly Val Ser Ser Ala Cys Pro Tyr Gln Gly Lys Ser Ser Phe Phe Arg
145                 150                 155                 160

Asn Val Val Trp Leu Ile Lys Lys Asn Ser Thr Tyr Pro Thr Ile Lys
                    165                 170                 175

Arg Ser Tyr Asn Asn Thr Asn Gln Glu Asp Leu Leu Val Leu Trp Gly
                    180                 185                 190

Ile His His Pro Asn Asp Ala Ala Glu Gln Thr Lys Leu Tyr Gln Asn
                    195                 200                 205

Pro Thr Thr Tyr Ile Ser Val Gly Thr Ser Thr Leu Asn Gln Arg Leu
                    210                 215                 220

Val Pro Arg Ile Ala Thr Arg Ser Lys Val Asn Gly Gln Ser Gly Arg
225                 230                 235                 240
```

```
Met Glu Phe Phe Trp Thr Ile Leu Lys Pro Asn Asp Ala Ile Asn Phe
                245                 250                 255

Glu Ser Asn Gly Asn Phe Ile Ala Pro Glu Tyr Ala Tyr Lys Ile Val
            260                 265                 270

Lys Lys Gly Asp Ser Thr Ile Met Lys Ser Glu Leu Glu Tyr Gly Asn
        275                 280                 285

Cys Asn Thr Lys Cys Gln Thr Pro Met Gly Ala Ile Asn Ser Ser Met
    290                 295                 300

Pro Phe His Asn Ile His Pro Leu Thr Ile Gly Glu Cys Pro Lys Tyr
305                 310                 315                 320

Val Lys Ser Asn Arg Leu Val Leu Ala Thr Gly Leu Arg Asn Ser Pro
                325                 330                 335

Gln Arg Glu Arg Arg Arg Lys Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Ile
        515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 13
<211> LENGTH: 918
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gly Ser Glu Lys Ile Val Leu Leu Phe Ala Ile Val Ser Leu Val
1               5                   10                  15

Lys Ser Asp Gln Ile Cys Ile Gly Tyr His Ala Asn Asn Ser Thr Glu
            20                  25                  30
```

```
Gln Val Asp Thr Ile Met Glu Lys Asn Val Thr Val Thr His Ala Gln
             35                  40                  45

Asp Ile Leu Glu Lys Thr His Asn Gly Lys Leu Cys Asp Leu Asp Gly
 50                  55                  60

Val Lys Pro Leu Ile Leu Arg Asp Cys Ser Val Ala Gly Trp Leu Leu
 65                  70                  75                  80

Gly Asn Pro Met Cys Asp Glu Phe Ile Asn Val Pro Glu Trp Ser Tyr
                 85                  90                  95

Ile Val Glu Lys Ala Asn Pro Val Asn Asp Leu Cys Tyr Pro Gly Asp
                100                 105                 110

Phe Asn Asp Tyr Glu Glu Leu Lys His Leu Leu Ser Arg Ile Asn His
                115                 120                 125

Phe Glu Lys Ile Gln Ile Ile Pro Lys Ser Ser Trp Ser Ser His Glu
                130                 135                 140

Ala Ser Leu Gly Val Ser Ser Ala Cys Pro Tyr Gln Gly Lys Ser Ser
145                 150                 155                 160

Phe Phe Arg Asn Val Val Trp Leu Ile Lys Lys Asn Ser Thr Tyr Pro
                165                 170                 175

Thr Ile Lys Arg Ser Tyr Asn Asn Thr Asn Gln Glu Asp Leu Leu Val
                180                 185                 190

Leu Trp Gly Ile His His Pro Asn Asp Ala Ala Glu Gln Thr Lys Leu
                195                 200                 205

Tyr Gln Asn Pro Thr Thr Tyr Ile Ser Val Gly Thr Ser Thr Leu Asn
                210                 215                 220

Gln Arg Leu Val Pro Arg Ile Ala Thr Arg Ser Lys Val Asn Gly Gln
225                 230                 235                 240

Ser Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
                260                 265                 270

Lys Ile Val Lys Lys Gly Asp Ser Thr Ile Met Lys Ser Glu Leu Glu
                275                 280                 285

Tyr Gly Asn Cys Asn Thr Lys Cys Gln Thr Pro Met Gly Ala Ile Asn
                290                 295                 300

Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Arg Arg Lys Lys Arg Gly Leu Phe Gly
                340                 345                 350

Ala Ile Ala Gly Phe Ile Glu Gly Gly Trp Gln Gly Met Val Asp Gly
                355                 360                 365

Trp Tyr Gly Tyr His His Ser Asn Glu Gln Gly Ser Gly Tyr Ala Ala
                370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
                420                 425                 430

Glu Asp Gly Phe Leu Asp Val Trp Thr Tyr Asn Ala Glu Leu Leu Val
                435                 440                 445
```

```
Leu Met Glu Asn Glu Arg Thr Leu Asp Phe His Asp Ser Asn Val Lys
450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
                485                 490                 495

Met Glu Ser Val Arg Asn Gly Thr Tyr Asp Tyr Pro Gln Tyr Ser Glu
        500                 505                 510

Glu Ala Arg Leu Lys Arg Glu Ile Ser Leu Glu Thr Asn Gln Ser
            515                 520                 525

Glu Glu Glu Gly Ser Tyr Thr Ile Asp Gln Ala Ala Asn Leu Leu Asn
530                 535                 540

Asp Leu Leu Ala Asp Ser Gln Gln Asn Leu Ser Asp Leu Gln Ala Ala
545                 550                 555                 560

Trp Ala Asn Lys Glu Pro Leu Leu Gln Gly Val Ile Ala Gly Leu Glu
                565                 570                 575

Ser Asp Leu Ala Asn Lys Gln Ala Glu Cys Ala Asp Leu Gln Gly Thr
            580                 585                 590

Leu Asp Ala Asp Gln Ala Ser Leu Asp Glu Ala Glu Ala Tyr Val Ala
        595                 600                 605

Trp Leu Gln Asp Arg Ile Ala Ala Asn His Lys Gln Ile Asp Asp Leu
610                 615                 620

Leu Asn Arg Arg Cys Gln Gln Asn Gly Asn Tyr Ile Glu Gly Leu Lys
625                 630                 635                 640

Asn Asp Lys Leu Ala Leu Ala Leu Leu Gln Phe Leu Glu Ala Gln Ile
                645                 650                 655

Gln Asn Lys Glu Ser Phe Ser Phe Leu Gln Lys Lys Asn Phe Met Lys
            660                 665                 670

Lys Leu Thr Arg Phe Leu Ser Ile Tyr Lys Thr Gly Asn Tyr Gln Gln
        675                 680                 685

Leu Ala Leu Leu Glu Lys Glu Tyr Val Asn Ala Asp Asp Tyr Ser Val
690                 695                 700

Asn Pro Asp Tyr Ser Thr Gly Asp Arg Thr Ala Asp Glu Ile Gly Ser
705                 710                 715                 720

Gly His Ile Asp Asn Asp Lys Gly Asp Ile Asp Val Ala Asp Phe Gln
                725                 730                 735

Glu Gly Glu Arg Lys Gly Trp Tyr Gln Val Lys Gln Glu Leu Leu Asp
            740                 745                 750

Leu Leu His Asn Leu Glu Gln Thr Ile Glu Ala Lys Ile Gln Gln Ala
        755                 760                 765

Gln Glu Asp Glu Val Asn Ser Asn Ser Ala Ala Asp Phe Lys Ser
770                 775                 780

Lys Leu Glu His Glu Ile Gln Val Tyr Glu Arg Glu Leu Ala Lys Trp
785                 790                 795                 800

Gln Gln Thr Val Ala Ala Leu Thr Ala Thr Val Ala Gln Asp His Glu
                805                 810                 815

Asn Val Asn Asn Cys His Ser Gln Glu Ala Ala Ile Gln Ala Asn Leu
            820                 825                 830

Asp Ala Ala Asn Gln Asp Tyr Ala Asn Glu Lys Ala Thr Phe Glu His
        835                 840                 845

Lys Gln Ala Asn Leu Gln Glu Glu Ile Glu Ile Phe Ile Glu Val Ile
850                 855                 860

Ala Tyr Tyr Asp Asp Asn Val Gln Asn Ala Gly Glu Asp Leu Lys Glu
```

```
                865                 870                 875                 880
Arg Val Glu Asp Tyr Ser Asp Gly Asn Phe Asp Asp Ala Ala Thr Tyr
                        885                 890                 895

Glu Asn Arg Gln Val Pro Asn Ile Asp Phe Ile Asn His His His His
                900                 905                 910

His His His His His His
            915

<210> SEQ ID NO 14
<211> LENGTH: 495
<212> TYPE: PRT
<213> ORGANISM: Unknown
<220> FEATURE:
<223> OTHER INFORMATION: Description of Unknown: Bacterial
      flagellin polypeptide

<400> SEQUENCE: 14

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300
```

```
Ala Ser Val Val Lys Met Ser Tyr Thr Asp Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
            355                 360                 365

Gly Lys Thr Glu Val Val Ser Ile Gly Gly Lys Thr Tyr Ala Ala Ser
370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
            435                 440                 445

Ser Ala Arg Ser Arg Ile Glu Asp Ser Asp Tyr Ala Thr Glu Val Ser
450                 455                 460

Asn Met Ser Arg Ala Gln Ile Leu Gln Ala Gly Thr Ser Val Leu
465                 470                 475                 480

Ala Gln Ala Asn Gln Val Pro Gln Asn Val Leu Ser Leu Leu Arg
                485                 490                 495

<210> SEQ ID NO 15
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Ser Lys Phe Asn Ile Leu Ile Ile Leu Ile Ile Ser Leu Phe
1               5                   10                  15

Ile Asn Glu Leu Arg Ala Ala Gln Val Ile Asn Thr Asn Ser Leu Ser
                20                  25                  30

Leu Leu Thr Gln Asn Asn Leu Asn Lys Ser Gln Ser Ala Leu Gly Thr
            35                  40                  45

Ala Ile Glu Arg Leu Ser Ser Gly Leu Arg Ile Asn Ser Ala Lys Asp
50                  55                  60

Asp Ala Ala Gly Gln Ala Ile Ala Asn Arg Phe Thr Ala Asn Ile Lys
65                  70                  75                  80

Gly Leu Thr Gln Ala Ser Arg Asn Ala Asn Asp Gly Ile Ser Ile Ala
                85                  90                  95

Gln Thr Thr Glu Gly Ala Leu Asn Glu Ile Asn Asn Asn Leu Gln Arg
            100                 105                 110

Val Arg Glu Leu Ala Val Gln Ser Ala Asn Ser Thr Asn Ser Gln Ser
        115                 120                 125

Asp Leu Asp Ser Ile Gln Ala Glu Ile Thr Gln Arg Leu Asn Glu Ile
    130                 135                 140

Asp Arg Val Ser Gly Gln Thr Gln Phe Asn Gly Val Lys Val Leu Ala
145                 150                 155                 160

Gln Asp Asn Thr Leu Thr Ile Gln Val Gly Ala Asn Asp Gly Glu Thr
                165                 170                 175
```

-continued

```
Ile Asp Ile Asp Leu Lys Gln Ile Asn Ser Gln Thr Leu Gly Leu Asp
        180                 185                 190

Thr Leu Asn Val Gln Gln Lys Tyr Lys Val Ser Asp Thr Ala Ala Thr
        195                 200                 205

Val Thr Gly Tyr Ala Asp Thr Thr Ile Ala Leu Asp Asn Ser Thr Phe
210                 215                 220

Lys Ala Ser Ala Thr Gly Leu Gly Thr Asp Gln Lys Ile Asp Gly
225                 230                 235                 240

Asp Leu Lys Phe Asp Asp Thr Thr Gly Lys Tyr Tyr Ala Lys Val Thr
                245                 250                 255

Val Thr Gly Gly Thr Gly Lys Asp Gly Tyr Tyr Glu Val Ser Val Asp
                260                 265                 270

Lys Thr Asn Gly Glu Val Thr Leu Ala Gly Gly Ala Thr Ser Pro Leu
                275                 280                 285

Thr Gly Gly Leu Pro Ala Thr Ala Thr Glu Asp Val Lys Asn Val Gln
        290                 295                 300

Val Ala Asn Ala Asp Leu Thr Glu Ala Lys Ala Ala Leu Thr Ala Ala
305                 310                 315                 320

Gly Val Thr Gly Thr Ala Ser Val Val Lys Met Ser Tyr Thr Asp Asn
                325                 330                 335

Asn Gly Lys Thr Ile Asp Gly Gly Leu Ala Val Lys Val Gly Asp Asp
                340                 345                 350

Tyr Tyr Ser Ala Thr Gln Asn Lys Asp Gly Ser Ile Ser Ile Asn Thr
                355                 360                 365

Thr Lys Tyr Thr Ala Asp Asp Gly Thr Ser Lys Thr Ala Leu Asn Lys
        370                 375                 380

Leu Gly Gly Ala Asp Gly Lys Thr Glu Val Val Ser Ile Gly Gly Lys
385                 390                 395                 400

Thr Tyr Ala Ala Ser Lys Ala Glu Gly His Asn Phe Lys Ala Gln Pro
                405                 410                 415

Asp Leu Ala Glu Ala Ala Ala Thr Thr Thr Glu Asn Pro Leu Gln Lys
                420                 425                 430

Ile Asp Ala Ala Leu Ala Gln Val Asp Thr Leu Arg Ser Asp Leu Gly
        435                 440                 445

Ala Val Gln Asn Arg Phe Asn Ser Ala Ile Thr Asn Leu Gly Asn Thr
450                 455                 460

Val Asn Asn Leu Thr Ser Ala Arg Ser Arg Ile Glu Asp Ser Asp Tyr
465                 470                 475                 480

Ala Thr Glu Val Ser Asn Met Ser Arg Ala Gln Ile Leu Gln Gln Ala
                485                 490                 495

Gly Thr Ser Val Leu Ala Gln Ala Asn Gln Val Pro Gln Asn Val Leu
                500                 505                 510

Ser Leu Leu Arg Leu Glu Val Ser Leu Arg Lys Ser Ser Asp Ala Met
        515                 520                 525

Lys Thr Ser Phe Ala Leu Glu Arg Leu Arg Phe Ile Gly Lys Lys Ser
        530                 535                 540

Pro Ile Ala Lys Gln Ile Ile Ser Ala Val Glu Leu His Leu Thr Thr
545                 550                 555                 560

Gly Gly Leu Val Asp Asp Val Ile Asp Leu Val Lys Gln Ala Gln Glu
                565                 570                 575

Asp Val Ala Asn Arg Asn Val Ala Leu Gln Ala Glu Tyr Thr Ala Lys
                580                 585                 590
```

```
Arg Gly Ala Leu Glu Asp Gln Ile Asn Thr Thr Thr Gln Gln Leu Asn
            595                 600                 605

Glu Glu Asn Asp Arg Leu Ala Val Val Asn Asp Ala Ile Asp Ala Leu
610                 615                 620

Asn Gly Gln Ile Asp Ser Leu Asn Thr Gln Ile Ala Asn Leu Val Gln
625                 630                 635                 640

Gln Leu Gln Asn Leu Gln Ala Arg Glu Asp Ala Ile Asn Gln Ala Arg
            645                 650                 655

Glu Val Asp Val Lys Thr Tyr Glu Val Arg Lys Gln Arg Asp Glu Asn
            660                 665                 670

Ser Leu Ala Val Leu Glu Gln Ile Ile Gln Arg Leu Leu Ala Leu Gln
            675                 680                 685

Gln Arg Gly Asn Ala Phe Leu Gln Val Ser Lys Lys Glu Ile Glu Arg
            690                 695                 700

Ile Leu Lys Arg Ile Pro Lys Ser Asn Pro Ile Gln Ala Leu Val Gln
705                 710                 715                 720

Leu Ser Thr Lys Phe Asp Glu Gln Arg Leu Ala Glu Val Ile Ser Lys
            725                 730                 735

Leu Gln Thr Ile Gln Ala Ala Ile Gln Ala Ser Tyr Ile Glu Asp Ala
            740                 745                 750

Asn Gly Glu Val Ala Asp Lys Gln Arg Tyr Asp Ala Leu Ile Gln Glu
            755                 760                 765

Ile Ala Thr Ile Arg Ala Gln Thr Gln Gln Leu Ala Asp Ala Gln
            770                 775                 780

Gln Ala Leu Ser Asp Ala Glu Ala Ser Leu Ala Gln Phe Val Gln Glu
785                 790                 795                 800

Gln Gly Asn Leu Gln Gln Ile Ala Val Asn Glu Gly Ile Leu Ala
            805                 810                 815

Asp Ala Gln Ala Ala Leu Ala His Thr Ile Ala Thr Tyr Glu Ala Arg
            820                 825                 830

Ile Gln Glu Gly Gln Glu Ala Leu Ala Ala Ile Asn Leu Ala Leu Asp
            835                 840                 845

Val Leu Gln Gln Asn Gln Ser Asp Leu Gln Gly Val Glu Asp Phe Ser
850                 855                 860

Asn Ala Tyr Asn Ala Tyr Gln Ala Gly Asn Ser Thr Asp Ala Gly Asp
865                 870                 875                 880

Asp Ala Gly Asp Asp Ser Gly Val Glu Gly Glu Ala Phe His His His
            885                 890                 895

His His His His His His
            900

<210> SEQ ID NO 16
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Ser Asn Lys Leu Leu Val Val Leu Phe Gly Phe Leu Ala Leu
1               5                   10                  15

Ala Ala Ala Thr Asn Gln Ser Glu Glu Glu Gly Ser Tyr Thr Ile Asp
            20                  25                  30

Gln Ala Ala Asn Leu Leu Asn Asp Leu Leu Ala Asp Ser Gln Gln Asn
            35                  40                  45
```

```
Leu Ser Asp Leu Gln Ala Ala Trp Ala Asn Lys Glu Pro Leu Leu Gln
     50                  55                  60

Gly Val Ile Ala Gly Leu Glu Ser Asp Leu Ala Asn Lys Gln Ala Glu
 65                  70                  75                  80

Cys Ala Asp Leu Gln Gly Thr Leu Asp Ala Asp Gln Ala Ser Leu Asp
                     85                  90                  95

Glu Ala Glu Ala Tyr Val Ala Trp Leu Gln Asp Arg Ile Ala Ala Asn
            100                 105                 110

His Lys Gln Ile Asp Asp Leu Leu Asn Arg Arg Cys Gln Gln Asn Gly
            115                 120                 125

Asn Tyr Ile Glu Gly Leu Lys Asn Asp Lys Leu Ala Leu Ala Leu Leu
        130                 135                 140

Gln Phe Leu Glu Ala Gln Ile Gln Asn Lys Glu Ser Phe Ser Phe Leu
145                 150                 155                 160

Gln Lys Lys Asn Phe Met Lys Lys Leu Thr Arg Phe Leu Ser Ile Tyr
                    165                 170                 175

Lys Thr Gly Asn Tyr Gln Gln Leu Ala Leu Leu Glu Lys Glu Tyr Val
            180                 185                 190

Asn Ala Asp Asp Tyr Ser Val Asn Pro Asp Tyr Ser Thr Gly Asp Arg
        195                 200                 205

Thr Ala Asp Glu Ile Gly Ser Gly His Ile Asp Asn Asp Lys Gly Asp
210                 215                 220

Ile Asp Val Ala Asp Phe Gln Glu Gly Glu Arg Lys Gly Trp Tyr Gln
225                 230                 235                 240

Val Lys Gln Glu Leu Leu Asp Leu Leu His Asn Leu Glu Gln Thr Ile
                    245                 250                 255

Glu Ala Lys Ile Gln Gln Ala Gln Glu Asp Glu Val Asn Ser Asn Ser
            260                 265                 270

Ala Ala Ala Asp Phe Lys Ser Lys Leu Glu His Glu Ile Gln Val Tyr
        275                 280                 285

Glu Arg Glu Leu Ala Lys Trp Gln Gln Thr Val Ala Ala Leu Thr Ala
290                 295                 300

Thr Val Ala Gln Asp His Glu Asn Val Asn Asn Cys His Ser Gln Glu
305                 310                 315                 320

Ala Ala Ile Gln Ala Asn Leu Asp Ala Ala Asn Gln Asp Tyr Ala Asn
                    325                 330                 335

Glu Lys Ala Thr Phe Glu His Lys Gln Ala Asn Leu Gln Glu Glu Ile
            340                 345                 350

Glu Ile Phe Ile Glu Val Ile Ala Tyr Tyr Asp Asp Asn Val Gln Asn
        355                 360                 365

Ala Gly Glu Asp Leu Lys Glu Arg Val Glu Asp Tyr Ser Asp Gly Asn
370                 375                 380

Phe Asp Asp Ala Ala Thr Tyr Glu Asn Arg Gln Val Pro Asn Ile Asp
385                 390                 395                 400

Phe Ile Asn Glu Asn Leu Tyr Phe Gln Gly His His His His His His
                    405                 410                 415

Cys Tyr Pro Tyr Asp Val Pro Asp Tyr Ala Ser Leu Asp Ile Gln Met
            420                 425                 430

Thr Gln Ser Pro Ser Ser Leu Ser Ala Ser Val Gly Asp Arg Val Thr
        435                 440                 445

Ile Thr Cys Arg Ala Ser Gln Asp Ile Arg Asn Tyr Leu Asn Trp Tyr
450                 455                 460
```

```
Gln Gln Lys Pro Gly Lys Ala Pro Lys Leu Leu Ile Tyr Tyr Thr Ser
465                 470                 475                 480

Arg Leu Leu Pro Gly Val Pro Ser Arg Phe Ser Gly Ser Gly Ser Gly
            485                 490                 495

Thr Asp Tyr Thr Leu Thr Ile Ser Ser Gln Glu Gln Glu Asp Ile Ala
        500                 505                 510

Thr Tyr Tyr Cys Gln Gln Gly Asn Thr Leu Pro Trp Thr Phe Gly Gln
    515                 520                 525

Gly Thr Lys Val Glu Ile Lys Arg Thr Gly Gly Gly Ser Gly Gly
    530                 535                 540

Gly Gly Ser Gly Gly Gly Ser Gly Gly Gly Ser Glu Val Gln
545                 550                 555                 560

Leu Val Glu Ser Gly Gly Gly Leu Val Gln Pro Gly Gly Ser Leu Arg
            565                 570                 575

Leu Ser Cys Ala Asp Ser Gly Tyr Ala Phe Ser Ser Ser Trp Met Asn
        580                 585                 590

Trp Val Arg Gln Ala Pro Gly Lys Gly Leu Glu Trp Val Gly Arg Ile
    595                 600                 605

Tyr Pro Gly Asp Gly Asp Thr Asn Tyr Asn Gly Lys Phe Lys Gly Arg
610                 615                 620

Ala Thr Ile Ser Ala Asp Lys Ser Ser Ser Thr Ala Tyr Leu Gln Met
625                 630                 635                 640

Asn Ser Leu Arg Ala Glu Asp Thr Ala Val Tyr Tyr Cys Ala Arg Ser
            645                 650                 655

Gly Leu Leu Arg Tyr Ala Met Asp Tyr Trp Gly Gln Gly Thr Leu Val
        660                 665                 670

Thr Val Ser Ser
        675

<210> SEQ ID NO 17
<211> LENGTH: 750
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Ser Arg Tyr Ala Ala Leu Phe Leu Leu Ala Leu Ile Ser Phe
1               5                   10                  15

Asn Ala Val Tyr Ala Val Ser Leu Arg Lys Ser Ser Asp Ala Met Lys
            20                  25                  30

Thr Ser Phe Ala Leu Glu Arg Leu Arg Phe Ile Gly Lys Lys Ser Pro
        35                  40                  45

Ile Ala Lys Gln Ile Ile Ser Ala Val Glu Leu His Leu Thr Thr Gly
    50                  55                  60

Gly Leu Val Asp Asp Val Ile Asp Leu Val Lys Gln Ala Gln Glu Asp
65                  70                  75                  80

Val Ala Asn Arg Asn Val Ala Leu Gln Ala Glu Tyr Thr Ala Lys Arg
                85                  90                  95

Gly Ala Leu Glu Asp Gln Ile Asn Thr Thr Gln Gln Leu Asn Glu
            100                 105                 110

Glu Asn Asp Arg Leu Ala Val Val Asn Asp Ala Ile Asp Ala Leu Asn
        115                 120                 125

Gly Gln Ile Asp Ser Leu Asn Thr Gln Ile Ala Asn Leu Val Gln Gln
    130                 135                 140
```

-continued

```
Leu Gln Asn Leu Gln Ala Arg Glu Asp Ala Ile Asn Gln Ala Arg Glu
145                 150                 155                 160

Val Asp Val Lys Thr Tyr Glu Val Arg Lys Gln Arg Asp Glu Asn Ser
                165                 170                 175

Leu Ala Val Leu Glu Gln Ile Ile Gln Arg Leu Leu Ala Leu Gln Gln
            180                 185                 190

Arg Gly Asn Ala Phe Leu Gln Val Ser Lys Lys Glu Ile Glu Arg Ile
        195                 200                 205

Leu Lys Arg Ile Pro Lys Ser Asn Pro Ile Gln Ala Leu Val Gln Leu
210                 215                 220

Ser Thr Lys Phe Asp Glu Gln Arg Leu Ala Glu Val Ile Ser Lys Leu
225                 230                 235                 240

Gln Thr Ile Gln Ala Ala Ile Gln Ala Ser Tyr Ile Glu Asp Ala Asn
                245                 250                 255

Gly Glu Val Ala Asp Lys Gln Arg Tyr Asp Ala Leu Ile Gln Glu Ile
            260                 265                 270

Ala Thr Ile Arg Ala Gln Thr Gln Gln Leu Ala Asp Ala Gln Gln
        275                 280                 285

Ala Leu Ser Asp Ala Glu Ala Ser Leu Ala Gln Phe Val Gln Glu Gln
290                 295                 300

Gly Asn Leu Gln Gln Gln Ile Ala Val Asn Glu Gly Ile Leu Ala Asp
305                 310                 315                 320

Ala Gln Ala Ala Leu Ala His Thr Ile Ala Thr Tyr Glu Ala Arg Ile
                325                 330                 335

Gln Glu Gly Gln Glu Ala Leu Ala Ala Ile Asn Leu Ala Leu Asp Val
            340                 345                 350

Leu Gln Gln Asn Gln Ser Asp Leu Gln Gly Val Glu Asp Phe Ser Asn
        355                 360                 365

Ala Tyr Asn Ala Tyr Gln Ala Gly Asn Ser Thr Asp Ala Gly Asp Asp
370                 375                 380

Ala Gly Asp Asp Ser Gly Val Glu Gly Glu Ala Phe Asp Asn Thr Glu
385                 390                 395                 400

Lys Val Ile Ser Ser Ile Glu Gly Arg Ser Ala Met Val His Val Arg
                405                 410                 415

Val Leu Lys Tyr Pro His Asn Ile Leu Phe Thr Asn Leu Thr Asn Asp
            420                 425                 430

Leu Phe Thr Tyr Leu Pro Lys Thr Tyr Asn Glu Ser Asn Phe Val Ser
        435                 440                 445

Asn Val Leu Glu Val Glu Leu Asn Asp Gly Glu Leu Phe Val Leu Ala
        450                 455                 460

Cys Glu Leu Ile Asn Lys Lys Cys Phe Gln Glu Gly Lys Glu Lys Ala
465                 470                 475                 480

Leu Tyr Lys Ser Asn Lys Ile Ile Tyr His Lys Asn Leu Thr Ile Phe
                485                 490                 495

Lys Ala Pro Phe Tyr Val Thr Ser Lys Asp Val Asn Thr Glu Cys Thr
            500                 505                 510

Cys Lys Phe Lys Asn Asn Tyr Lys Ile Val Leu Lys Pro Lys Tyr
        515                 520                 525

Glu Lys Lys Val Ile His Gly Cys Asn Phe Ser Ser Asn Val Ser Ser
        530                 535                 540

Lys His Thr Phe Thr Asp Ser Leu Asp Ile Ser Leu Val Asp Asp Ser
545                 550                 555                 560
```

```
Ala His Ile Ser Cys Asn Val His Leu Ser Glu Pro Lys Tyr Asn His
            565                 570                 575

Leu Val Gly Leu Asn Cys Pro Gly Asp Ile Ile Pro Asp Cys Phe Phe
        580                 585                 590

Gln Val Tyr Gln Pro Glu Ser Glu Glu Leu Glu Pro Ser Asn Ile Val
            595                 600                 605

Tyr Leu Asp Ser Gln Ile Asn Ile Gly Asp Ile Glu Tyr Tyr Glu Asp
        610                 615                 620

Ala Glu Gly Asp Asp Lys Ile Lys Leu Phe Gly Ile Val Gly Ser Ile
625                 630                 635                 640

Pro Lys Thr Thr Ser Phe Thr Cys Ile Cys Lys Lys Asp Lys Lys Ser
                645                 650                 655

Ala Tyr Met Thr Val Thr Ile Asp His His His His His His Cys Pro
            660                 665                 670

Ala Gly Thr Val Val Asp Asp Gly Thr Ser Thr Asn Phe Val Ala Leu
        675                 680                 685

Ala Ser Glu Cys Thr Lys Cys Gln Ala Asn Phe Tyr Ala Ser Lys Thr
    690                 695                 700

Ser Gly Phe Ala Ala Gly Thr Asp Thr Cys Thr Glu Cys Ser Lys Lys
705                 710                 715                 720

Leu Thr Ser Gly Ala Thr Ala Lys Val Tyr Ala Glu Ala Thr Gln Lys
                725                 730                 735

Ala Gln Cys Ala Ser Tyr Pro Tyr Asp Val Pro Asp Tyr Ala
            740                 745                 750

<210> SEQ ID NO 18
<211> LENGTH: 906
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Ser Lys Leu Leu Val Val Leu Phe Gly Phe Leu Ala Leu Ala
1               5                   10                  15

Ala Ala Thr Asn Gln Ser Glu Glu Glu Gly Ser Tyr Thr Ile Asp Gln
            20                  25                  30

Ala Ala Asn Leu Leu Asn Asp Leu Leu Ala Asp Ser Gln Gln Asn Leu
        35                  40                  45

Ser Asp Leu Gln Ala Ala Trp Ala Asn Lys Glu Pro Leu Leu Gln Gly
    50                  55                  60

Val Ile Ala Gly Leu Glu Ser Asp Leu Ala Asn Lys Gln Ala Glu Cys
65                  70                  75                  80

Ala Asp Leu Gln Gly Thr Leu Asp Ala Asp Gln Ala Ser Leu Asp Glu
                85                  90                  95

Ala Glu Ala Tyr Val Ala Trp Leu Gln Asp Arg Ile Ala Ala Asn His
            100                 105                 110

Lys Gln Ile Asp Asp Leu Leu Asn Arg Arg Cys Gln Gln Asn Gly Asn
        115                 120                 125

Tyr Ile Glu Gly Leu Lys Asn Asp Lys Leu Ala Leu Ala Leu Leu Gln
    130                 135                 140

Phe Leu Glu Ala Gln Ile Gln Asn Lys Glu Ser Phe Ser Phe Leu Gln
145                 150                 155                 160

Lys Lys Asn Phe Met Lys Lys Leu Thr Arg Phe Leu Ser Ile Tyr Lys
                165                 170                 175
```

```
Thr Gly Asn Tyr Gln Gln Leu Ala Leu Leu Glu Lys Glu Tyr Val Asn
            180                 185                 190

Ala Asp Asp Tyr Ser Val Asn Pro Asp Tyr Ser Thr Gly Asp Arg Thr
        195                 200                 205

Ala Asp Glu Ile Gly Ser Gly His Ile Asp Asn Asp Lys Gly Asp Ile
210                 215                 220

Asp Val Ala Asp Phe Gln Glu Gly Arg Lys Gly Trp Tyr Gln Val
225                 230                 235                 240

Lys Gln Glu Leu Leu Asp Leu His Asn Leu Glu Gln Thr Ile Glu
                245                 250                 255

Ala Lys Ile Gln Gln Ala Gln Glu Asp Glu Val Asn Ser Asn Ser Ala
            260                 265                 270

Ala Ala Asp Phe Lys Ser Lys Leu Glu His Glu Ile Gln Val Tyr Glu
        275                 280                 285

Arg Glu Leu Ala Lys Trp Gln Gln Thr Val Ala Ala Leu Thr Ala Thr
290                 295                 300

Val Ala Gln Asp His Glu Asn Val Asn Asn Cys His Ser Gln Glu Ala
305                 310                 315                 320

Ala Ile Gln Ala Asn Leu Asp Ala Ala Asn Gln Asp Tyr Ala Asn Glu
            325                 330                 335

Lys Ala Thr Phe Glu His Lys Gln Ala Asn Leu Gln Glu Glu Ile Glu
        340                 345                 350

Ile Phe Ile Glu Val Ile Ala Tyr Tyr Asp Asp Asn Val Gln Asn Ala
            355                 360                 365

Gly Glu Asp Leu Lys Glu Arg Val Glu Asp Tyr Ser Asp Gly Asn Phe
    370                 375                 380

Asp Asp Ala Ala Thr Tyr Glu Asn Arg Gln Val Pro Asn Ile Asp Phe
385                 390                 395                 400

Ile Asn Asp Gln Ile Cys Ile Gly Tyr His Ala Asn Asn Ser Thr Glu
            405                 410                 415

Gln Val Asp Thr Ile Met Glu Lys Asn Val Thr Val Thr His Ala Gln
        420                 425                 430

Asp Ile Leu Glu Lys Thr His Asn Gly Lys Leu Cys Asp Leu Asp Gly
    435                 440                 445

Val Lys Pro Leu Ile Leu Arg Asp Cys Ser Val Ala Gly Trp Leu Leu
450                 455                 460

Gly Asn Pro Met Cys Asp Glu Phe Ile Asn Val Pro Glu Trp Ser Tyr
465                 470                 475                 480

Ile Val Glu Lys Ala Asn Pro Val Asn Asp Leu Cys Tyr Pro Gly Asp
            485                 490                 495

Phe Asn Asp Tyr Glu Glu Leu Lys His Leu Leu Ser Arg Ile Asn His
        500                 505                 510

Phe Glu Lys Ile Gln Ile Ile Pro Lys Ser Ser Trp Ser Ser His Glu
    515                 520                 525

Ala Ser Leu Gly Val Ser Ser Ala Cys Pro Tyr Gln Gly Lys Ser Ser
            530                 535                 540

Phe Phe Arg Asn Val Val Trp Leu Ile Lys Lys Asn Ser Thr Tyr Pro
545                 550                 555                 560

Thr Ile Lys Arg Ser Tyr Asn Asn Thr Asn Gln Glu Asp Leu Leu Val
            565                 570                 575

Leu Trp Gly Ile His His Pro Asn Asp Ala Ala Glu Gln Thr Lys Leu
        580                 585                 590
```

```
Tyr Gln Asn Pro Thr Thr Tyr Ile Ser Val Gly Thr Ser Thr Leu Asn
            595                 600                 605

Gln Arg Leu Val Pro Arg Ile Ala Thr Arg Ser Lys Val Asn Gly Gln
610                 615                 620

Ser Gly Arg Met Glu Phe Phe Trp Thr Ile Leu Lys Pro Asn Asp Ala
625                 630                 635                 640

Ile Asn Phe Glu Ser Asn Gly Asn Phe Ile Ala Pro Glu Tyr Ala Tyr
                645                 650                 655

Lys Ile Val Lys Lys Gly Asp Ser Thr Ile Met Lys Ser Glu Leu Glu
            660                 665                 670

Tyr Gly Asn Cys Asn Thr Lys Cys Gln Thr Pro Met Gly Ala Ile Asn
        675                 680                 685

Ser Ser Met Pro Phe His Asn Ile His Pro Leu Thr Ile Gly Glu Cys
690                 695                 700

Pro Lys Tyr Val Lys Ser Asn Arg Leu Val Leu Ala Thr Gly Leu Arg
705                 710                 715                 720

Asn Ser Pro Gln Arg Glu Arg Arg Lys Arg Gly Leu Phe Gly
                725                 730                 735

Ala Ile Ala Gly Phe Ile Glu Gly Gly Trp Gln Gly Met Val Asp Gly
            740                 745                 750

Trp Tyr Gly Tyr His His Ser Asn Glu Gln Gly Ser Gly Tyr Ala Ala
        755                 760                 765

Asp Lys Glu Ser Thr Gln Lys Ala Ile Asp Gly Val Thr Asn Lys Val
        770                 775                 780

Asn Ser Ile Ile Asp Lys Met Asn Thr Gln Phe Glu Ala Val Gly Arg
785                 790                 795                 800

Glu Phe Asn Asn Leu Glu Arg Arg Ile Glu Asn Leu Asn Lys Lys Met
                805                 810                 815

Glu Asp Gly Phe Leu Asp Val Trp Thr Tyr Asn Ala Glu Leu Leu Val
            820                 825                 830

Leu Met Glu Asn Glu Arg Thr Leu Asp Phe His Asp Ser Asn Val Lys
        835                 840                 845

Asn Leu Tyr Asp Lys Val Arg Leu Gln Leu Arg Asp Asn Ala Lys Glu
850                 855                 860

Leu Gly Asn Gly Cys Phe Glu Phe Tyr His Lys Cys Asp Asn Glu Cys
865                 870                 875                 880

Met Glu Ser Val Arg Asn Gly Thr Tyr Asp Tyr Pro Gln Tyr Ser Glu
                885                 890                 895

Glu Ala Arg Leu Lys Arg Glu Glu Ile Ser
            900                 905

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 19

His His His His His His His His His His
1               5                   10

<210> SEQ ID NO 20
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      6xHis tag

<400> SEQUENCE: 20

His His His His His His
1               5
```